United States Patent
Lazar et al.

(10) Patent No.: US 9,574,006 B2
(45) Date of Patent: *Feb. 21, 2017

(54) OPTIMIZED ANTI-CD30 ANTIBODIES

(75) Inventors: Gregory Alan Lazar, Arcadia, CA (US); John R. Desjarlais, Pasadena, CA (US); Philip W. Hammond, Sierra Madre, CA (US); David F. Carmichael, Monrovia, CA (US); Bao-lu Chen, San Ramon, CA (US); Seung Y. Chu, Upland, CA (US); Sher Bahadur Karki, Pasadena, CA (US); Lori Kunkel, San Francisco, CA (US)

(73) Assignee: Xencor, Inc., Monrovia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/163,465

(22) Filed: Jun. 17, 2011

(65) Prior Publication Data
US 2012/0014943 A1   Jan. 19, 2012

Related U.S. Application Data

(62) Division of application No. 12/089,384, filed as application No. PCT/US2006/039306 on Oct. 6, 2006, now Pat. No. 7,973,136.

(60) Provisional application No. 60/776,598, filed on Feb. 24, 2006, provisional application No. 60/737,998, filed on Nov. 18, 2005, provisional application No. 60/724,624, filed on Oct. 6, 2005, provisional application No. 60/750,697, filed on Dec. 15, 2005, provisional application No. 60/745,536, filed on Apr. 25, 2006.

(51) Int. Cl.
*A61K 39/395*  (2006.01)
*C07K 16/28*  (2006.01)

(52) U.S. Cl.
CPC ....... *C07K 16/2878* (2013.01); *C07K 2317/24* (2013.01); *C07K 2317/72* (2013.01); *C07K 2317/732* (2013.01)

(58) Field of Classification Search
None
See application file for complete search history.

(56) References Cited

U.S. PATENT DOCUMENTS

| | | |
|---|---|---|
| 4,816,397 A | 3/1989 | Boss et al. |
| 5,225,348 A | 7/1993 | Nagata et al. |
| 5,266,491 A | 11/1993 | Nagata et al. |
| 5,328,987 A | 7/1994 | Maliszewski |
| 5,541,087 A | 7/1996 | Lo et al. |
| 5,576,184 A | 11/1996 | Better et al. |
| 5,623,053 A | 4/1997 | Gastinel et al. |
| 5,624,821 A | 4/1997 | Winter et al. |
| 5,633,162 A | 5/1997 | Keen et al. |
| 5,648,237 A | 7/1997 | Carter |
| 5,648,260 A | 7/1997 | Winter et al. |
| 5,821,337 A | 10/1998 | Carter et al. |
| 5,834,597 A | 11/1998 | Tso et al. |
| 5,885,573 A | 3/1999 | Bluestone et al. |
| 6,030,613 A | 2/2000 | Blumberg et al. |
| 6,033,876 A | 3/2000 | Lemke et al. |
| 6,086,875 A | 7/2000 | Blumberg et al. |
| 6,121,022 A | 9/2000 | Presta et al. |
| 6,165,745 A | 12/2000 | Ward et al. |
| 6,188,965 B1 | 2/2001 | Mayo et al. |
| 6,194,551 B1 | 2/2001 | Idusogie et al. |
| 6,242,195 B1 | 6/2001 | Idusogie et al. |
| 6,269,312 B1 | 7/2001 | Mayo et al. |
| 6,277,375 B1 | 8/2001 | Ward |
| 6,331,415 B1 | 12/2001 | Cabilly et al. |
| 6,358,733 B1 | 3/2002 | Motwani et al. |
| 6,365,161 B1 | 4/2002 | Deo et al. |
| 6,403,312 B1 | 6/2002 | Dahiyat et al. |
| 6,444,789 B1 | 9/2002 | Luo |
| 6,485,726 B1 | 11/2002 | Blumberg et al. |
| 6,528,624 B1 | 3/2003 | Idusogie et al. |
| 6,538,124 B1 | 3/2003 | Idusogie et al. |
| 6,632,927 B2 | 10/2003 | Adair et al. |
| 6,649,165 B2 | 11/2003 | Schubert |
| 6,708,120 B1 | 3/2004 | Mayo et al. |
| 6,719,971 B1 | 4/2004 | Carter et al. |
| 6,737,056 B1 | 5/2004 | Presta |
| 6,792,356 B2 | 9/2004 | Mayo et al. |
| 6,797,492 B2 | 9/2004 | Daugherty et al. |
| 6,801,861 B2 | 10/2004 | Mayo et al. |
| 6,804,611 B2 | 10/2004 | Mayo et al. |
| 6,821,505 B2 | 11/2004 | Ward |
| 6,933,368 B2 | 8/2005 | Co et al. |
| 6,946,292 B2 | 9/2005 | Kanda et al. |
| 6,950,754 B2 | 9/2005 | Mayo et al. |
| 6,982,321 B2 | 1/2006 | Winter |
| 6,992,234 B2 | 1/2006 | Roopenian |
| 7,090,843 B1 | 8/2006 | Francisco et al. |
| 7,317,091 B2 | 1/2008 | Lazar et al. |
| 7,662,925 B2 | 2/2010 | Lazar et al. |
| 7,973,136 B2 | 7/2011 | Lazar et al. |
| 8,388,955 B2 * | 3/2013 | Lazar et al. ............... 424/130.1 |
| 2001/0036459 A1 | 11/2001 | Ravetch |
| 2002/0004587 A1 | 1/2002 | Miller et al. |
| 2002/0048772 A1 | 4/2002 | Dahiyat et al. |

(Continued)

FOREIGN PATENT DOCUMENTS

| | | |
|---|---|---|
| EP | 0 268 636 B1 | 8/1997 |
| EP | 1 176 195 A1 | 1/2002 |

(Continued)

OTHER PUBLICATIONS

Li et al .Engineering therapeutic monoclonal antibodies. Immunological Reviews 2008, vol. 222: 9-27.*

(Continued)

*Primary Examiner* — Maher Haddad
(74) *Attorney, Agent, or Firm* — Polsinelli PC

(57) ABSTRACT

An antibody that targets CD30, wherein the antibody comprises at least one modification relative to a parent antibody and the antibody binds with altered affinity to an FcγR or alters effector function as compared to the parent antibody. Also disclosed are methods of using the anti-CD30 antibody.

9 Claims, 30 Drawing Sheets

(56) References Cited

U.S. PATENT DOCUMENTS

| | | |
|---|---|---|
| 2002/0062010 A1 | 5/2002 | Arathoon et al. |
| 2002/0090648 A1 | 7/2002 | Dahiyat et al. |
| 2002/0106368 A1 | 8/2002 | Bot et al. |
| 2002/0142374 A1 | 10/2002 | Gallo et al. |
| 2002/0155537 A1 | 10/2002 | Carter et al. |
| 2002/0164328 A1 | 11/2002 | Shinkawa et al. |
| 2002/0192222 A1 | 12/2002 | Blumberg et al. |
| 2003/0012789 A1 | 1/2003 | Blumberg et al. |
| 2003/0049654 A1 | 3/2003 | Dahiyat et al. |
| 2003/0073164 A1 | 4/2003 | Simmons et al. |
| 2003/0078385 A1 | 4/2003 | Arathoon et al. |
| 2003/0105294 A1 | 6/2003 | Gillies et al. |
| 2003/0108548 A1 | 6/2003 | Bluestone et al. |
| 2003/0118592 A1 | 6/2003 | Ledbetter et al. |
| 2003/0130827 A1 | 7/2003 | Bentzien et al. |
| 2003/0133939 A1 | 7/2003 | Ledbetter et al. |
| 2003/0138417 A1 | 7/2003 | Kaisheva et al. |
| 2003/0143682 A1 | 7/2003 | Nicolaides et al. |
| 2003/0157108 A1 | 8/2003 | Presta |
| 2003/0158289 A1 | 8/2003 | Rusin et al. |
| 2003/0158389 A1 | 8/2003 | Idusogie et al. |
| 2003/0166868 A1 | 9/2003 | Presta et al. |
| 2003/0175884 A1 | 9/2003 | Umana et al. |
| 2003/0190311 A1 | 10/2003 | Dall'Acqua et al. |
| 2003/0208054 A1 | 11/2003 | Olsen et al. |
| 2003/0224397 A1 | 12/2003 | Lowman et al. |
| 2003/0229208 A1 | 12/2003 | Queen et al. |
| 2003/0235536 A1 | 12/2003 | Blumberg et al. |
| 2004/0002587 A1 | 1/2004 | Watkins et al. |
| 2004/0018194 A1 | 1/2004 | Francisco et al. |
| 2004/0043429 A1 | 3/2004 | Dahiyat et al. |
| 2004/0043430 A1 | 3/2004 | Dahiyat et al. |
| 2004/0062763 A1 | 4/2004 | Mosser et al. |
| 2004/0185045 A1 | 9/2004 | Koenig et al. |
| 2004/0191244 A1 | 9/2004 | Presta |
| 2004/0191256 A1 | 9/2004 | Raju |
| 2004/0192897 A2 | 9/2004 | Winter |
| 2004/0228856 A1 | 11/2004 | Presta |
| 2004/0258677 A1 | 12/2004 | Waldmann et al. |
| 2004/0258682 A1 | 12/2004 | Leung et al. |
| 2004/0259150 A1 | 12/2004 | Nakamura et al. |
| 2005/0014934 A1 | 1/2005 | Hinton et al. |
| 2005/0031626 A1 | 2/2005 | Stevenson |
| 2005/0032114 A1 | 2/2005 | Hinton et al. |
| 2005/0033029 A1 | 2/2005 | Lu |
| 2005/0037000 A1 | 2/2005 | Stavenhagen et al. |
| 2005/0037002 A1 | 2/2005 | Velardi et al. |
| 2005/0038610 A1 | 2/2005 | Mayo et al. |
| 2005/0054046 A1 | 3/2005 | Presta et al. |
| 2005/0064514 A1 | 3/2005 | Stavenhagen et al. |
| 2005/0118174 A1 | 6/2005 | Presta |
| 2005/0152894 A1 | 7/2005 | Krummen et al. |
| 2005/0175614 A1 | 8/2005 | Ledbetter et al. |
| 2005/0202023 A1 | 9/2005 | Ledbetter et al. |
| 2005/0202028 A1 | 9/2005 | Ledbetter et al. |
| 2005/0202534 A1 | 9/2005 | Ledbetter et al. |
| 2005/0215767 A1 | 9/2005 | Koenig et al. |
| 2005/0226864 A1 | 10/2005 | Hinton et al. |
| 2005/0233382 A1 | 10/2005 | Presta |
| 2005/0272128 A1 | 12/2005 | Umana et al. |
| 2005/0276799 A1 | 12/2005 | Hinton et al. |
| 2006/0008883 A1 | 1/2006 | Lazar et al. |
| 2006/0019316 A1 | 1/2006 | Mayo et al. |
| 2006/0134105 A1* | 6/2006 | Lazar et al. ............... 424/133.1 |
| 2007/0148171 A1* | 6/2007 | Lazar ............... A61K 39/39591 424/144.1 |
| 2007/0166309 A1 | 7/2007 | Lazar et al. |
| 2007/0258987 A1 | 11/2007 | Francisco et al. |
| 2007/0275460 A1* | 11/2007 | Desjarlais et al. ............ 435/325 |

FOREIGN PATENT DOCUMENTS

| | | |
|---|---|---|
| EP | 1 229 125 A1 | 8/2002 |
| EP | 1 255 209 A2 | 11/2002 |
| EP | 0 753 065 B1 | 5/2003 |
| EP | 0 805 628 B1 | 5/2003 |
| EP | 1 323 346 A2 | 11/2003 |
| EP | 1 323 346 A3 | 11/2003 |
| EP | 0 888 125 B1 | 5/2004 |
| EP | 0 904 107 B1 | 10/2004 |
| EP | 0 383 799 B2 | 2/2005 |
| EP | 1 255 826 B1 | 9/2005 |
| WO | WO 87/07277 A1 | 3/1987 |
| WO | WO 88/07089 A1 | 9/1988 |
| WO | WO 91/06305 A1 | 5/1991 |
| WO | WO 91/19515 A1 | 12/1991 |
| WO | WO 92/04053 A1 | 3/1992 |
| WO | WO 92/16562 A1 | 10/1992 |
| WO | WO 92/22324 A1 | 12/1992 |
| WO | WO 94/29351 A2 | 12/1994 |
| WO | WO 94/29351 A3 | 12/1994 |
| WO | WO 95/05468 A1 | 2/1995 |
| WO | WO 96/22024 A1 | 7/1996 |
| WO | WO 97/28267 A1 | 8/1997 |
| WO | WO 97/34631 A1 | 9/1997 |
| WO | WO 98/02462 A1 | 1/1998 |
| WO | WO 98/05787 A1 | 2/1998 |
| WO | WO 98/23289 A1 | 6/1998 |
| WO | WO 98/47089 A1 | 10/1998 |
| WO | WO 99/04813 A1 | 2/1999 |
| WO | WO 99/51642 A1 | 10/1999 |
| WO | WO 99/54342 A1 | 10/1999 |
| WO | WO 99/58572 A1 | 11/1999 |
| WO | WO 00/09560 A2 | 2/2000 |
| WO | WO 00/09560 A3 | 2/2000 |
| WO | WO 00/23564 A2 | 4/2000 |
| WO | WO 00/23564 A3 | 4/2000 |
| WO | WO 00/24782 A2 | 5/2000 |
| WO | WO 00/24782 A3 | 5/2000 |
| WO | WO 00/42072 A2 | 7/2000 |
| WO | WO 00/42072 A3 | 7/2000 |
| WO | WO 00/61739 A1 | 10/2000 |
| WO | WO 01/29246 A1 | 4/2001 |
| WO | WO 01/38490 A2 | 5/2001 |
| WO | WO 01/57088 A1 | 8/2001 |
| WO | WO 01/59066 A2 | 8/2001 |
| WO | WO 01/59066 A3 | 8/2001 |
| WO | WO 02/30954 A1 | 4/2002 |
| WO | WO 02/31140 A1 | 4/2002 |
| WO | WO 02/44215 A2 | 6/2002 |
| WO | WO 0243661 A2 | 6/2002 |
| WO | WO 02/060919 A2 | 8/2002 |
| WO | WO 02/060919 A3 | 8/2002 |
| WO | WO 02/061090 A3 | 8/2002 |
| WO | WO 02/061093 A1 | 8/2002 |
| WO | WO 03/014325 A2 | 2/2003 |
| WO | WO 03/014325 A3 | 2/2003 |
| WO | WO 03/016470 A2 | 2/2003 |
| WO | WO 03/035835 A2 | 5/2003 |
| WO | WO 03/035835 A3 | 5/2003 |
| WO | WO 03/054213 A2 | 7/2003 |
| WO | WO 03/059282 A | 7/2003 |
| WO | WO 03/074679 | 9/2003 |
| WO | WO 03/089624 A2 | 10/2003 |
| WO | WO 2004/004662 A2 | 1/2004 |
| WO | WO 2004/004798 A2 | 1/2004 |
| WO | WO 2004/004798 A3 | 1/2004 |
| WO | WO 2004/016750 A2 | 2/2004 |
| WO | WO 2004/016750 A3 | 2/2004 |
| WO | WO 2004/022717 A2 | 3/2004 |
| WO | WO 2004/022717 A3 | 3/2004 |
| WO | WO 2004/024871 A2 | 3/2004 |
| WO | WO 2004/024889 A2 | 3/2004 |
| WO | WO 2004/029207 A | 4/2004 |
| WO | WO 2004/035752 A2 | 4/2004 |
| WO | WO 2004/056312 A2 | 7/2004 |
| WO | WO 2004/063351 A2 | 7/2004 |
| WO | WO 2004/063351 A3 | 7/2004 |
| WO | WO 2004/074455 A2 | 9/2004 |
| WO | WO 2004/074455 A3 | 9/2004 |
| WO | WO 2004/092219 A2 | 10/2004 |
| WO | WO 2004/103404 A1 | 12/2004 |
| WO | WO 2004/110472 A2 | 12/2004 |

(56) References Cited

FOREIGN PATENT DOCUMENTS

| | | |
|---|---|---|
| WO | WO 2005/000899 A2 | 1/2005 |
| WO | WO 2005/001025 A2 | 1/2005 |
| WO | WO 2005/007809 A2 | 1/2005 |
| WO | WO 2005/011376 A2 | 2/2005 |
| WO | WO 2005/012877 A2 | 2/2005 |
| WO | WO 2005/013090 A2 | 2/2005 |
| WO | WO 2005/018572 A2 | 3/2005 |
| WO | WO 2005/023866 A2 | 3/2005 |
| WO | WO 2005/027966 A2 | 3/2005 |
| WO | WO 2005/037867 A1 | 4/2005 |
| WO | WO 2005/040217 A2 | 5/2005 |
| WO | WO 2005/047327 A2 | 5/2005 |
| WO | WO 2005/056606 A | 6/2005 |
| WO | WO 2005/056759 A | 6/2005 |
| WO | WO 2005/060642 A2 | 7/2005 |
| WO | WO 2005/060642 A3 | 7/2005 |
| WO | WO 2005/063815 A2 | 7/2005 |
| WO | WO 2005/070963 A1 | 8/2005 |
| WO | WO 2005/116078 A1 | 12/2005 |
| WO | WO 2005/123780 A2 | 12/2005 |
| WO | WO 2006/012500 A2 | 2/2006 |

OTHER PUBLICATIONS

Wahl et al. The anti-CD30 monoclonal antibody SGN-30 promotes growth arrest and DNA fragmentation in vitro and affects antitumor activity in models of Hodgkin's disease. Cancer Res. Jul. 1, 2002;62(13):3736-42.*
Hammond et al. A Humanized Anti-CD30 Monoclonal Antibody, XmAbTM2513, with Enhanced In Vitro Potency Against CD30-Positive Lymphomas Mediated by High Affinity Fc-Receptor Binding. (Blood (ASH) Annual Meeting, Nov. 2005; 106: 1470).*
Zhukovsky et al.: "XmAB 5574: an FC engineered anti CD-19 monoclonal antibody with in vitro and in vivo efficacy against Lymphoma and Leukemia" Internet, [Online] Apr. 2008 (Apr. 2008), Retrieved from the Internet: URL:http://www.xencor.com/downloads/aarc-sandiego-april-12-16-2008.pdf.*
Notice of Allowance issued in U.S. Appl. No. 12/089,384, dated Feb. 2, 2011, 11 pages.
Request for Continued Examination and Amendment and Response to Final Office Action filed in U.S. Appl. No. 12/089,384, dated Dec. 27, 2010, 10 pages.
Final Office Action issued in U.S. Appl. No. 12/089,384, dated Sep. 27, 2010, 8 pages.
Amendment and Response to Office Action filed in U.S. Appl. No. 12/089,384, dated Jul. 29, 2010, 13 pages.
Non-Final Office Action issued in U.S. Appl. No. 12/089,384, dated Apr. 29, 2010, 15 pages.
Amendment and Response to Office Action filed in U.S. Appl. No. 12/089,384, dated Feb. 18, 2010, 25 pages.
Non-Final Office Action issued in U.S. Appl. No. 12/089,384, dated Aug. 18, 2009, 85 pages.
Amendment and Response to Restriction Requirement filed in U.S. Appl. No. 12/089,384, dated Jun. 4, 2009, 8 pages.
Restriction Requirement issued in U.S. Appl. No. 12/089,384, dated May 4, 2009, 14 pages.
Aase, A., et al., "The extended hinge region of IgG3 is not required for high phogocytic capacity mediated by Fcγ receptors, but the heavy chains must be disulfide bonded," Eur J Immunol., 23:1546-1551 (1993).
Abadeh, S., et al., "Remodelling the oligosaccharide of human IgG antibodies: effects on biological activities," Biochem Soc Trans., 25(4):S661 (1997).
Akewanlop, C., et al., "Phagocytosis of Breast Cancer Cells Mediated by Anti-MUC-1 Monoclonal antibody, DF3, and Its Bispecific Antibody" Cancer Research, 61:4061-4065 (May 15, 2001).
Alegre, M., et al., "Effect of a Single Amino Acid Mutation on the Activating and Immunosuppressive Properties of a "Humanised" OKT3 Monoclonal Antibody," J. Immunology, 148:3461-3468 (Jun. 1, 1992).

Alegre, M., et al., "A non-activating "humanized" anti-CD3 monoclonal antibody retains immunosuppressive properties in vivo," Transplantation, 57:1537-1543 (Jun. 1994).
Amigorena, S., et al., "Fc receptors for IgG and antigen presentation on MHC class I and class II molecules" Immunology, 11:385-390 (1999).
Amigorena, S., et al., "Fc receptor signaling and trafficking: a connection for antigen processing" Immunological Reviews, 172:279-284 (1999).
Andreakos, E., et al., "Monoclonal antibodies in immune and inflammatory diseases," Curr. Opin. Biotech., 13:615-620 (2002).
Armour, K. L., et al., "Recombinant human IgG molecules lacking Fcγ receptor binding and monocyte triggering activities," Eur. J Immunol., 29:2613-2624 (1999).
Armour, K. L., et al., "Differential binding to human FcγRIIa and FcγRIIb receptors by human IgG wildtype and mutant antibodies," Molecular Immunology, 40:585-593 (2003).
Ashkenazi, A., et al., "Mapping the CD4 binding site for human immunodeficiency virus by alanine-scanning mutagenesis," PNAS USA, 87:7150-7154 (Sep. 1990).
Ashkenazi, et al., "Immunoadhesins as research tools and therapeutic agents," Curr Opin Immunol, 9:195-200 (1997).
Bolland, S., "A Newly Discovered Fc Receptor that Explains IgG-Isotype Disparities in Effector Responses," J. Immunity, 23:2-4 (Jul. 2005).
Boruchov, A. M., et al., "Activating and inhibitory IgG Fc receptors on human DCs mediate opposing functions" J. Clin. Invest. doi:10.1172/JCI24772 (Sep. 16, 2005).
Bowles, J. A., et al., "CD16 polymorphisms and NK activation induced by monoclonal antibody-coated target cells," Journal of Immunological Methods, pp. 1-12 (2005).
Brekke, O. H., et al., "Human IgG isotype-specific amino acid residues affecting complement-mediated cell lysis and phogocytosis," Eur J. Immunl, 24(10):2542-5247 (Oct. 1994).
Brekke, O. H., et al., "Human IgG3 can adopt the disulfide bond pattern characteristic for IgG1 without resembling it in complement mediated cell lysis," Mol. Immunol. 30(16):1419-1425 (Nov. 1993).
Bruggemann, M., et al., "Comparison of the Effector Functions of Human Immunoglobulins Using a Matched Set of Chimeric Antibodies," J. Exp. Med., 166:1351-1361 (Nov. 1987).
Bruggemann, M., et al., "A matched set of rat/mouse chimeric antibodies. Identification and biological properties of rat H chain constant regions μ, γ1, γ2a, γ2b, γ2c, ε, and $α^1$," J. Immunol, 142(9):3145-3150 (May 1989).
Burmeister, W. P., et al., "Crystal structure of the complex of rat neonatal Fc receptor with Fc" Nature, 372:379-383 (Nov. 24, 1994).
Canfield, S. M., et al., "The Binding Affinity of Human IgG for its High Affinity Fc Receptor is Determined by Multiple Amino Acids in the $C_H2$ Domain and is Modulated by the Hinge Region," J. Exp. Med., 173:1483-1491 (Jun. 1991).
Caron, P. C., et al., "Engineered Humanized Dimeric Forms of IgG are More Effective Antibodies," J. Exp. Med., 176:1191-1195 (Oct. 1992).
Caron, P. C., et al., "Murine and humanized constructs of monoclonal antibody M195 (anti-CD33) for the therapy of acute myelogenous leukemia," Cancer, 73(3 Supp):1049-1056 (Feb. 1, 1994).
Carpenter, P. A., et al., "Non-Fc Receptor-Binding Humanized Anti-CD3 Antibodies Induce Apoptosis of Activated Human T Cells," Journal of Immunology, 165:6205-6213 (2000).
Carter, P., "Improving the Efficacy of Antibody-Based Cancer Therapies," Nature Reviews, 1:118-129 (2001).
Carter, P., et al., "Humanization of an anti-p185$^{HER2}$ antibody for human cancer therapy" PNAS, 89:4285-4289 (May 1992).
Cartron, G. et al., "Therapeutic activity of humanized anti-Cd20 monoclonal antibody and polymorphism in IgG Fc receptor FcγRIIIa gene," Blood, 99(3):754-758 (Feb. 1, 2002).
Chadd, H., et al., "Therapeutic antibody expression technology," Curr. Opin. Biotech., 12:188-194 (2001).
Chamow, et al., "Immunoadhesins: principles and applications," Trends Biotechnol, 14:52-60 (Feb. 1996).

(56) References Cited

OTHER PUBLICATIONS

Chapman, P. B., "T-Cell Chauvinists Versus Antibody Advocates—Can't We All Just Get Along?" *J. Clin. Oncology*, 22(22):4446-4448 (Nov. 15, 2004).
Chappel, M. S., et al., "Identification of a Secondary FcγRI Binding Site within a Genetically Engineered Human IgG Actibody," *J. Biol. Chem.*, 268(33):25124-25131 (Nov. 1993).
Chintalacharuvu, K. R., et al., "Hybrid IgA2/IgG1 Antibodies with Tailor-Made Effector Functions," *Clinical Immunology*, 101(1):21-31—(Oct. 2001).
Clark, M., "Antibody humanization: a case of the 'Emperor's new clothes?'" *Immunol. Today*, 21(8):397-402 (2000).
Clynes, R. A., et al., "Inhibitory Fc receptors modulate in vivo cytoxicity against tumor targets," *Nature Medicine*, 6(4):443-446 (Apr. 2000).
Clynes, R., et al., "Modulation of Immune complex-induced Inflammation In Vivo by the Coordinate Expression of Activation and Inhibitory Fc Receptors," *J. Exp, Med.*, 189(1):179-185 (Jan. 4, 1999).
Clynes, R., "Immune complexes as therapy for autoimmunity" *J. Clin. Invest.*, 115(1):25-27 (Jan. 2005).
Clynes, R., et al., "Fc receptors are required in passive and active immunity to melanoma," *PNAS USA*, 95:652-656 (Jan. 1998).
Cohen-Sodal, J. FG., et al., "Review: Fcγ receptors" *Immunology Letts*, 92:199-205 (2004).
Cole, M. S., et al., "Human IgG2 variants of chimeric anti-CD3 are nonmitogenic to T cells," *J. Immunol.*, 159:3613-3621 (1997).
Coloma, M. J., et al., "The hinge as a spacer contributes to covalent assembly and is required for function of IgG," *J. Immunol.*, 158:733-740 (1997).
Cragg, M., et al., "Signaling antibodies in cancer therapy," *Curr. Opin. Immunol.*, 11:541-547 (1999).
D'Uscio, C. H., et al., "Cellular cytotoxicity mediated by isotype-switch variants of a monoclonal antibody to human neuroblastoma," *Br. J. Cancer*, 64:445-450 (1991).
Da Silveira, S. A., et al., Complement Activation Selectively Potentiates the Pathogenicity of the IgG2 b and IgG3 Isotypes of a High Affinity Anti-Erythrocyte Autoantibody, *J. Exp. Med.*, 195(6):665-672 (Mar. 18, 2002).
Dall'Acqua, D. F., et al., "Increasing the Affinity of a Human IgG1 for the Neonatal Fc Receptor: Biological Consequences," *Journal of Immunology*, 169:5171-5180 (2002).
Dall'Acqua, W., et al., "Antibody Engineering," *Curr. Opin Structural Biol.*, 8:443-450 (1998).
Davies, J., et al., "Expression of GnTIII in a recombinant anti-CD20 CHO production cell line: Expression of antibodies with altered glycoforms leads to an increase in ADCC through higher affinity for FCγRIII," *Biotechnol Bioeng*, 74:288-294 (Feb. 18, 2001).
Davis, R. S., et al., "Fc receptor homologs: newest members of a remarkably diverse Fc receptor gene family," *Imm. Revs*, 190:123-136 (2002).
Delano, W. L., et al., "Convergent Solutions to Binding at a Protein-Protein Interface" *Science*, 287:1279-1283 (Feb. 18, 2000).
Dhodapkar, K. M., et al.,."Antitumor Monoclonal Antibodies Enhance Cross-Presentation of Cellular Antigens and the Generation of Myeloma-specific Killer T-Cells by Dendritic Cells" *J. Exp Med.*, 195(1):125-133 (Jan. 7, 2002).
Dhodapkar, K. M., et al., "Recruiting dendritic cells to improve antibody therapy of cancer" *PNAS*, 102(18):6243-6244 (May 3, 2005).
Dhodapkar, K. M., et al., "Selective blockade of inhibitory Fcγ receptor enables human dendritic cell maturation with IL-12p70 production and immunity to antibody-coated tumor cells" *PNAS*, 102(8):2910-2915 (Feb. 22, 2005).
Dhodapkar, M. V., et al., "T cells from the tumor microenvironment of patients with progressive myeloma can generate strong, tumor-specific cytolytic responses to autologous, tumor-loaded dendritic cells" *PNAS*, 99:(20)13009-13013 (Oct. 1, 2002).
Duncan, A. R., et al., "Localization of the binding site for the human high-affinity Fc receptor on IgG," *Nature*, 332:563-564 (Apr. 7, 1988).
Duncan, A. R., et al., "The binding site for C1q on IgG," *Nature* 332(6166):738-740 (Apr. 21, 1988).
Edelman, G. M., et al., "The Covalent Structure of an Entire γG Immunoglobulin Molecule," *PNAS*, 63:78-85 (1969).
Ehrhardt, G. R. A., et al., "The inhibitory potential of Fc receptor homolog 4 on memory B cells," *PNAS, USA*, 100(23):13489-13494 (Nov. 11, 2003).
Ellison, J. W., et al., "The nucleotide sequence of a human immunoglobulin $c\gamma_1$ gene" *Nucleic Acids Research*, 10(13):4071-4079 (1982).
Ernst, L. K., et al., "Molecular characterization of six variant Fcγ receptor class I (CD64) transcripts," *Molecular Immunology*, 35:943-954 (1998).
Facchetti, F., et al., "An unusual Fc receptor-related protein expressed in human centroblasts," *PNAS, USA*, 99(6):3776-3781 (Mar. 19, 2002).
Gaboriaud, C., et al., "The Crystal Structure of the Globular Head of Complement Protein C1q Provides a Basis for Its Versatile Recognition Properties," *J. Biol. Chem.*, 278(47):46974-46982 (2003).
Garman, S. C., et al., "Structure of the Fc fragment of human IgE bound to its high-affinity receptor FcεRIα," *Nature*, 406:259-266 (Jul. 20, 2000).
Getahun, A., et al., "IgG2a-Mediated Enhancement of Antibody and T Cell Responses and Its Relation to Inhibitory and Activating Fcγ Receptors," *J. of Immunology*, 172:5269-5276 (2004).
Ghazizadeh, S., et al., "Physical and Functional Association of Src-related Protein Tyrosine Kinases with FcγRII in Monocytic THP-1 Cells," *J. Biol. Chem.*, 269(12):8878-8884 (1994).
Ghetie, V., et al., "FcRn: the MHC class I-related receptor that is more than an IgG transporter" *Immunology Today*, 18(12):592-598 (Dec. 1997).
Ghetie, V., et al., "Multiple Roles for the Major Histocompatibility Complex Class I-Related Receptor FcRn," *Annu. Rev. Immunol.* 18:739-766 (2000).
Glennie, M., et al., "Clinical trials of antibody therapy," *Immun. Today*, 21(8):403-410 (Aug. 2000).
Glennie, M., et al., "Renaissance of cancer therapeutic antibodies," *Drug Discovery Today*, 8(11):503-510 (Jun. 2003).
Gonzales, N. R., et al., "SDR grafting of a murine antibody using multiple human germline templates to minimize its immunogenicity," *Molecular Immunology*, 41:863-872 (2004).
Greenwood, J., "Molecular Recognition in the Structure and Assembly of Filamentous Bacteriophages," Dissertation submitted to the University of Cambridge (Oct. 1989).
Greenwood, J., et al., "Structural motifs involved in human IgG antibody effector functions," *Eur. J. Immunol.*, 23:1098-1104 (1993).
Greenwood, J., et al., "Dual Importance of Positive Charge in the C-Terminal Region of Filamentous Bacteriophage Coat Protein for Membrane Insertion and DNA-Protein Interaction in Virus Assembly," *Virology*, 171:444-452 (1989).
Greenwood, J., et al., "Effector functions" of matched sets of recombinant human IgG subclass antibodies," Dissertation submitted to Cambridge University, Cambridge, UK (Feb. 1993).
Greenwood, J., et al., "Engineering multiple-domain forms of the therapeutic antibody CAMPATH-1H: effects on complement lysis," *Ther Immunol.*, 1:247-255 (1994).
Groh, V., et al., "Efficient cross-priming of tumor antigen-specific T cells by dendritic cells sensitized with diverse anti-MICA opsonized tumor cells" PNAS, 102(18):6461-6466 (May 3, 2005).
Harrison, P. T., et al., "Domain swap chimeras to study the binding of IgG by FcγRI, the high affinity receptor for IgG," *Biochem Soc Trans.*, 24:144S (1996).
Hayhurst, A., et al., "High-throughput antibody isolation," *Curr. Opin. Chem. Biol.*, 5:683-689 (2001).
Hazenbos, W. L., et al., "Murine IgG1 complexes Trigger Immune Effector Functions Predominately via FcγRIII (CD16)," *J. of Immunology*, 161:3026-3032 (1998).

(56) References Cited

OTHER PUBLICATIONS

Henry, A. J., et al., "Participation of the N-Terminal of Cε3 in the Binding of Human IgE to Its High-Affinity Receptor FcεRI," *Biochemistry*, 36:15568-15578 (1997).
Hezareh, M., et al., "Effector Function Activities of a Panel of Mutants of a Broadly Neutralizing Antibody against Human Immunodeficiency Virus Type I," *Journal of Virology*, 75(24):12161-12168 (Dec. 2001).
Hinton, P. R., et al., "Engineered human IgG Antibodies with Longer Serum Half-Lives in Primates," *J. Biol Chem.*, 279(8):6213-6216 (Feb. 20, 2004).
Hogarth, P., "Fc receptors are major mediators of antibody based inflammation in autoimmunity," *Curr. Opin. Immun.*, 14:798-802 (2002).
Holliger, P., et al., "Antibodies come back from the brink," *Nature Biotechnology*, 16:1015-1016 (Nov. 1998).
Hudson, P., "Recombinant antibody constructs in cancer therapy," *Curr. Opin. Immunology*, 11:548-557 (1999).
Hudson, P., "Recombinant antibody fragments," *Curr. Opin in Biotechnology*, 9:395-402 (1998).
Hutchins, et al., "Improved biodistribution, tumor targeting, and reduced immunogenicity in mice with a γ4 variant of Campath-1H," *PNAS USA*, 92:11980-11984 (Dec. 1995).
Idusogie, E. E., et al., "Engineered Antibodies with Increased Activity to Recruit Complement," *J. of Immunology*, 166:2571-2575 (2001).
Idusogie, E. E., et al., "Mapping of the C1q Binding Site on Rituxan, a Chimeric Antibody with a Human IgG1 Fc," *J. of Immunology*, 164:4178-4184 (2000).
Isaacs, J. D., "From bench to bedside: discovering rules for antibody design, and improving serotherapy with monoclonal antibodies," *Rheumatology*, 40:724-738 (2001).
Isaacs, J. D., "Improving Serotherapy with Monoclonal Antibodies" dissertation submitted to the University of Cambridge (Mar. 1991).
Issacs, J. D., et al., "Therapy with Monoclonal Antibodies, II. The contribution of Fcγ Receptor binding and the Influenece of $C_H1$ and $C_H3$ Domains on In Vivo Effector Function," *J. of Immunology*, 161:3862-3869 (1998).
Issacs, J. D., et al., "Therapy with Monoclonal Antibodies: an in vivo model for the assessment of therapeutic potential," *J. Immunol.*, 148(10):3062-3071 (May 15, 1992).
Jefferis, R., et al., "Modulation of FcγR and human complement activation by IgG3-Core oligosaccharide interactions," *Immunol Lett*, 54:101-104 (1996).
Jefferis, R., et al., "Recognition sites on human IgG for Fcγ receptors: the role of glycosylation," *Immunol Letters*, 44:111-117 (1995).
Jefferis, R., et al., "Interaction sites on human IgG-Fc for FcγR: current models," *Immunology Letts.*, 82:57-65 (2002).
Jefferis, R., et al., "Modulation of FcγR and human complement activation by IgG3-core oligosaccharide interactions," *Immunology Letters*, 54:101-104 (1996) and erratum at *Immunology Letters*, 58:67 (1997).
Jefferis, R., et al., "Molecular definition of interaction sites on human IgG for Fc receptors (huFcγ R)," *Mol Immunol.*, 27(12):1237-1240 (1990).
Jendeberg, L., et al., "Engineering of $Fc_1$ and $Fc_3$ from human immunoglobulin G to analyse subclass specificity for staphylococcal protein A, " *Journal of Immunological Methods*, 201:25-34 (1997).
Johnson, G., et al., "Kabat Database and its applications: 30 years after the first variability plot," *Nucleic Acids Research*, 28(1):214-218 (2000).
Johnson, G., et al., "Kabat Database and its applications: future directions," *Nucleic Acids Research*, 29(1):205-206 (2001).
Junghans, R. P., et al., "The protection receptor for IgG catabolism is the $β_2$-microglobulin-containing neonatal intestinal transport receptor," *PNAS*, 93:5512-5516 (May 1996).

Kalergis, A.M., et al., "Inducing Tumor Immunity through the Selective Engagement of Activating Fcγ Receptors on Dendritic Cells" *J. Exp. Med.* 195(12):1653-1659 (Jun. 17, 2002).
Kan, K. S., et al., "Thioether-Bonded Constructs of Fab'γ and Fcγ Modules Utilizing Differential Reduction of Interchain Disulfide Bonds," *Journal of Immunology*, 166:1320-1326 (2001).
Karassa, F. B., et al., "The role of FcγRIIA and IIIA polymorphisms in autoimmune diseases," *Biomedicine & Pharmacotherapy*, 58:286-291 (2004).
Kim, J., et al., "Mapping the site on human IgG for binding of the MHC class I-related receptor, FcRn" *Eur. J. Immunol.*, 29:2819-2825 (1999).
Kim, J. K., et al., "Identifying amino acid residues that influence plasma clearance of murine IgG1 fragments by site-directed mutagenesis," *Eur J. Immunol.*, 24:542-548 (1994).
Kim, J. K., et al., "Localization of the site of the murine IgG1 molecule that is involved in binding to the murine intestinal Fc receptor," *Eur J Immunol*, 24:2429-2439 (1994).
Kim, T. D., et al., "Analysis of FcγRIII and IgG Fc Polymorphism Reveals Functional and Evolutionary Implications of Protein-Protein Interaction," *J. Mol. Evol.*, 53:1-9 (2001).
Krapp, S., et al., "Structural analysis of human IgG-Fc glycoforms reveals a correlation between glycosylation and structural integrity," *J Mol Biol*, 325:979-989 (2003).
Kurucz, I., et al., "Bacterially expressed human FcγRIIb is soluble and functionally active after in vitro refolding" *Immunology Letts.*, 75:33-40 (2000).
Lehrnbecher, T., et al., "Variant Genotypes of the Low-Affinity Fcγ Receptors in Two Control Populations and a Review of Low-Affinity Fcγ Receptor Polymorphisms in Control and Disease Populations," *Blood*, 94:4220-4232 (Dec. 15, 1999).
Lund, J., et al., "Human FcγRI and FcγRII interact with distinct but overlapping sites on human IgG," *J Immunol*, 147:2657-2662 (Oct. 15, 1991).
Lund, J., et al., "Multiple binding sites on the CH2 domain of IgG for mouse FcγRII," *Mol Immunol*, 29 53-59 (1992).
Lund, J., et al., "Multiple interactions of IgG with its core oligosaccharide can modulate recognition by complement and human Fcγ receptor I and influence the synthesis of its oligosaccharide chains," *J Immunol*, 154:4963-4969 (1996).
Lund, J., et al., "Oligosaccharide-protein interactions in IgG can modulate recognition by Fcγ receptors," *Faseb J*, 9:115-119 (Jan. 1995).
Lund, J., et al., "A protein structural change in aglycosylated IgG3 correlates with loss of huFcγR1 and huFcγR111 binding and/or activation," *Mol. Immunol.*, 27(11):1145-1153 (1990).
Lund, J., et al., "Control of IgG/Fc glycosylation: a comparision of oligosaccharides from chimeric human/mouse and mouse subclass immunoglobulin Gs," *Mol Immunol.*, 30(8):741-748 (1993).
Maenaka, K., et al., "The Human Low Affinity Fcγ Receptors IIa, IIb and III Bind IgG with Fast Kinetics and Distinct Thermodynamic Properties" *J. Biol. Chem.* 276(48):44898-44904 (2001).
Martin, W. L., et al., "Characterization of the 2:1 Complex between the Class I MHC-Related Fc Receptor and its Fc Ligand in Solution." *Biochemistry*, 38:12639-12647 (1999).
Martin, W. L., et al., "Crystal Structure at 2.8 Å of an FcRn/Heterodimeric Fc Complex: Mechanism of pH-Dependent Binding" *Molecular Cell*, 7:867-877 (Apr. 2001).
Masztalerz, A , et al., Mechanisms of macrophage cytotoxicity in IL-2 and IL-12 mediated tumor regression, *Cancer Immunol Immunother.* 52:235-242 (2003).
Maxwell, K.F., et al., "Crystal structure of the human leukocyte Fc receptor, FcγRIIa," *Nature Structural Biology*, 6(5):437-442 (May 1999).
Mayfield, S. P., et al., "Expression and assembly of a fully active antibody algae," *PNAS*, 100(2):438-442 (Jan. 21. 2003).
Maynard, J., et al., "Antibody Engineering," *Annu. Rev. Biomed. Eng.*, 2:339-376 (2000).
Mechetina, L. V., et al., "Identification of CD16-2, a novel mouse receptor homologous to CD16/FcγRIII." *Immunogenetics*, 54:463-468 (2002).
Merchant, A. M., et al., "An efficient route to human bispecific IgG," *Nat Biotechnol.*, 16:677-681 (Jul. 1998).

(56) References Cited

OTHER PUBLICATIONS

Metes, D., et al., "Expression of Functional CD32 Molecules on Human NK Cells is Determined by an Allelic Polymorphism of the Fcγ RIIC Gene," *Blood*, 91(7):2369-2380 (Apr. 1, 1998).
Michaelson, T. E., et al., "Antibody Dependent Cell-Mediated Cytotoxicity Induced by Chimeric Mouse-Human IgG Subclasses and IgG3 Antibodies with Altered Hinge Region," *Molecular Immunology*, 29(3):319-326 (1992).
Michaelson, T. E., et al., "One disulfide bond in front of the second heavy chain constant region is necessary and sufficient for effector functions of human IgG3 without a genetic hinge," *PNAS*, 91:9243-9247 (Sep. 1994).
Michaelson, T. E., et al., "Primary Structure of the 'Hinge' Region of Human IgG3." *J Biol Chem.*, 252(3):883-889 (Feb. 10, 1977).
Miller, I., et al., IRTAs: a new family of immunoglobulinlike receptors differentially expressed in B cells, *Blood*, 99(8):2662-2669 (Apr. 15, 2002).
Mimura, Y., et al., "Role of Oligosaccharide Residues of IgG I-Fc in Fcγ RIIb Binding," *J. Biol. Chem.*, 276(49):45539-45547 (Dec. 7, 2001).
Morea, V., et al., "Antibody Modeling: Implications for Engineering and Design," *Methods*, 20:267-279 (2000).
Morgan, A., et al., "The N-terminal end of the CH2 domain of chimeric human IgG1 anti-HLA-DR is necessary for C1q, Fc gamma RI and Fc gamma RIII binding," *Immunology*, 86(2):319-324 (Oct. 1995).
Nakamura, K., et al., "Dissection and optimization of immune effector functions of humanized anti-ganglioside GM2 monoclonal antibody," *Molecular Immunology*, 37:1035-1046 (2000).
Neidhardt-Berard, E., et al., Dendritic cells loaded with killed breast cells induce differentiation of tumor-specific cytoxic T lymphocytes *Breast Cancer Res.*, 6:R322-R328 (Apr. 30, 2004).
Nimmerjahn, F., et al., "FcγRIV: A Novel FcR with Distinct IgG Subclass Specificity," *Immunity*, 23:41-51 (Jul. 2005).
Nimmerjahn, F., et al., "Divergent immunoglobulin-G Subclass Activity Through Selective Fc Receptor Binding," *Science*, 310:1510-1512 (Dec. 2, 2005).
Nimmerjahn. F., et al., "Supporting Online Material for: Divergent Immunoglobulin-G Subclass Activity Through Selective Fc Receptor Binding," *Science*, 310:1510 (2005).
Niwa, R., et al., "Defucosylated Chimeric Anti-CC Chemokine Receptor 4 IgG1 with Enhanced Antibody Dependnent Cellular cytotoxicity Shows Potent Therapeutic Activity to T-Cell Leukemia and Lymphoma," *Cancer Research*, 64:2127-2133 (Mar. 15, 2004).
Norderhaug, L., et al., "Chimeric mouse human IgG3 antibodies with an IgG4-like hinge region induce complement-mediated lysis more efficiently than IgG3 with normal hinge," *Eur. J. immunol.*, 21(10):2379-2384 (Oct. 1991).
O'Connor, S. J., et al., "Humanization of an antibody against human protein C and calcium-dependence involving framework residues," *Protein Engineering*, 11(4):321-328 (1998).
Ober, R. J., et al., "Differences in promiscuity for antibody-FcRn interactions across species: implications for therapeutic antibodies," *International Immunology*, 13(12):1551-1559 (2001).
Ober, R. J., et al., "Exocytosis of IgG as mediated by the receptor, FcRn: An analysis at the single-molecule level" *PNAS*, 101(30):11076-11081 (Jul. 27, 2004).
Okazaki, A., et al., "Fucose Depletion from Human IgG1 Oligosaccharide Enhances Binding Enthalpy and Association Rate Between IgG1 and FcγRIIIa," *J. Mol. Biol.*, 336:1239-1249 (2004).
Parren, P. W., et al., "Characterization of IgG FcR-mediated proliferation of human T cells induced by mouse and human anti-CD3 monoclonal antibodies. Identification of a functional polymorphism to human IgG2 anti-CD3," *J. Immunol.*, 148(3):695-701 (Feb. 1, 1992).
Parren, P. W., et al., "On the interaction of IgG subclasses with the low affinity FcγRIIa (CD32) on human monocytes, neutrophils, and platelets. Analysis of a functional polymorphism to human IgG2," *J. Clin. Invest.*, 90:1537-1546 (Oct. 1992).

Pearce, K. H., et al., "Mutational Analysis of Thrombopoietin for Identification of Receptor and Neutralizing Antibody Sites," *J. Biol. Chem.*, 272(33):20595-20602 (Aug. 15, 1997).
Penichet, M., et al., "Antibody-cytokine fusion proteins for the therapy of cancer," *Journal of Immunological Methods*, 248:91-101 (2001).
Preithner, S., et al., "High concentrations of therapeutic IgG1 antibodies are needed to compensate for inhibition of antibody-dependnent cellular cytotoxicity by excess endogenous immunoglobulin G," *Molecular Immunology*, (2005).
Presta, L.G., et al., "Engineering therapeutic antibodies for improved function," *Biochemical Society Transactions*, 30(part 4):487-490 (2002).
Radaev, S., et al., "Recognition of IgG by Fcγ Receptor," *J. Biol. Chem.*, 276(19):16478-16483 (May 11, 2001).
Radaev, S., et al., "Review: Recognition of immunoglobulins by Fcγ recptors," *Molecular Immunology*, 38:1073-1083 (2001).
Radaev, S., et al., "The Structure of Human Type III Fcγ Receptor in Complex with Fc," *J. Biol. Chem.*, 276(19):16469-16477 (2001).
Rafiq, K., et al., "Immune complex-mediated antigen presentation induces tumor immunity" *J. Clin. Invest.* 110:71-79 (2002).
Raghavan, M., et al., "Fc Receptors and Their Interactions with Immunoglobulins" *Annu. Rev. Cell Div. Biol.*, 12:181-220 (1996).
Ravetch, J. V., et al., "IgG Fc Receptors" *Annu. Rev. Immunol.*, 19:275-290 (2001).
Ravetch, J. V., et al., "Immune Inhibitory Receptors," *Science*, 290:84-89 (Oct. 6, 2000).
Ravetch, J. V., et al., "Fc Receptors," *Annu. Rev. Immunol.*, 9:457-492 (1991).
Reddy P. R., et al., "Elimination of Fc Receptor-Dependent Effector Functions of a Modified IgG4 Monoclonal Antibody to Human CD4" *J. Immunol.*, 164:1925-1933 (2000).
Redpath, S. et al., "The Influence of the Hinge Region Length in Binding of Human IgG to Human Fcγ Receptors," *Human Immunology*, 59:720-727 (1998).
Reichert, J., "Monoclonal antibodies in the clinic," *Nature Biotechnology*, 19:819-822 (2001).
Rozsnyay, Z., et al., "Distinctive role of IgG1 and IgG3 isotypes in Fc-γR-mediated functions," *Immunology*, 66(4):491-498 (Apr. 1989).
Sarmay, G., et al., "Mapping and Comparison of the Interaction Sites on the Fc Region of IgG Responsible for Triggering Antibody Dependent Cellular Cytotoxicity (ADCC) Through Different Types of Human FCγ Receptor," *Molecular Immunology*, 29(5):633-639 (1992).
Sautes-Fridman, C., et al., "Fc Gamma Receptors: A Magic Link with the Outside World," *ASHI Quarterly*, 148-151, (Fourth Quarter 2003).
Shields, R. L., et al., "High Resolution Mapping of the Binding Site on Human IgG1 for FcγRI, FcγRII, FcγRIII, and FcRn and Design of IgG1 Variants with Improved Binding to the FcγR" *J. Biol. Chem.*, 276(9):6591-6604 (2001).
Shields, R. L., et al., "Lack of Fucose on human IgG1 N-Linked Oligosaccharide Improves Binding to Human FcγRIII and Antibody-dependent Cellular Toxicity" *J. Biol. Chem.*, 277(30)26733-26740 (2002).
Shinkawa, T., et al., "The Absence of Fucose but Not the Presence of Galactose or Bisecting N-Acetylglucosamine of Human IgG1 complex-type Oligosaccharides Shows the Critical Role of Enhancing Antibody-dependent Cellular Cytotoxicity" *J. Biol. Chem.*, 278(5):3466-3473 (Jan. 31, 2003).
Shopes, B., "A genetically engineered human IgG mutant with enhanced cytolytic activity," *J Immunol.*, 148(9):2918-2922 (May 1, 1992).
Shopes, B., et al., "Recombinant human IgG1-murine IgE chimeric Ig. Construction, expression, and binding to human Fc gamma receptors," *J. Immunol.*, 145(11):3842-3848 (Dec. 1, 1990).
Simmons, L. C., et al., "Expression of full-length immunoglobulins in *Escherichia coli*; rapid and efficient production of aglycosylated antibodies" *J Immunol.*, Methods, 263:133-147 (2002).

(56) References Cited

OTHER PUBLICATIONS

Smith, I. F. R., et al., "Addition of a μ-Tailpiece to IgG Results in Polymeric Antibodies with Enhanced Effector Functions Including Complement-Mediated Cytolysis by IgG4," *J. Immunology*, 154:2226-2236 (1995).
Smith, K. G., et al., "T cell activation by anti-T3 antibodies: comparison of IgG1 and IgG2b switch variants and direct evidence for accessory function of macrophage Fc receptors," *Eur. J. Immunol.*, 16(5):478-486 (May 16, 1986).
Sonderman, P., et al., "Crystal structure of the soluble form of the human FCγ-receptor IIb: a new member of the immunoglobulin superfamily at 1.7Å resolution" *EMBO Journal*, 18(5):1095-1103 (1999).
Sonderman, P., et al., "Human Fcγ Receptor IIb Expressed in *Escherichia coli* Reveals IgG Binding Capability," *Biol. Chem.* 380:717-721 (Jun. 1999).
Sonderman, P., et al., "Molecular Basis for Immune Complex Recognition: A comparison of Fc-Receptor Structures," *J. Mol. Biol.*, 309:737-749 (2001).
Sonderman, P., et al., "The 3.20-Å crystal structure of the human IgG1 Fc fragment-FcγRIII complex," *Nature*, 406:267-273 (Jul. 20, 2000).
Sorenson, V., et al., "Effect of the IgM and IgA secretory tailpieces on polymerization and secretion of IgM and IgG," *J Immunol.*, 156(8):2858-2865 (Apr. 15, 1996).
Steplewski, Z., et al., "Biological activity of human-mouse IgG1, IgG2, IgG3, and IgG4 chimeric monoclonal antibodies with anti-tumor specificity," *PNAS USA*, 85:4852-4856 (Jul. 1988).
Stevenson, G. T., et al., "Preparation of Fcγ for addition to sulfhydryl-expressing ligands with minimal disturbance of the hinge," *J. of Immunological Methods*, 231:169-175 (1999).
Tao, M., et al., "Structural Features of Human immunoglobulin G that Determine Isotype-specific Differences in Complement Activation," *J. Exp. Med.*. 178:661-667 (Aug. 1993).
Tao, M., et al., "The Differential Ability of Human IgG1 and IgG4 to Activate Complement is Determined by the COOH-terminal Sequence of the $C_H2$ domain" *J. Exp. Med*, 173:1025-1028 (Apr. 1991).
Thommesen, J. E., et al., "Lysine 322 in the human IgG3 $C_H2$ domain is crucial for antibody dependent complement activation" *Molecular Immunology*, 37:995-1014 (2000).
Thrush, G., et al., "Immunotoxins: An Update," *Ann. Rev. Immunol.*, 14:49-71 (1996).
Torphy, T., "Pharmaceutical biotechnology Monoclonal antibodies: boundless potential, daunting challenges—Editorial Overview," *Curr. Opin. Biotechnol.*, 13:589-591 (2002).
Trail, P., et al., "Monoclonal antibody drug conjugates in the treatment of cancer" *Curr. Opin. Immunol.*, 11:584-588 (1999).
Trikha, M., "Monoclonal antibodies as therapeutics in oncology," *Curr. Opin. Biotech.*, 13:609-614 (2002).
Tuijnman W. B., et al., "A flow cytometric rosetting assay for the analysis of IgG-Fc receptor interactions," *J Immunol Methods*, 127(2):207-214 (Mar. 9, 1990).
Uchide, J. et al., "The Innate Mononuclear Phagocyte Network Depletes B Lymphocytes through Fc Receptor dependent mechanisms during Anti-CD20 Antibody Immunotherapy" *J. Exp. Med.* 199(12):1659-1669 (Jun. 21, 2004).
Umana, P., et al., "Engineered glycoforms of an antineuroblastoma IgG1 with optimized antibody-dependent cellular cytotoxic activity," *Nature Biotechnology*, 17:176-180 (1999).
Van Dijk, M., et al., "Human antibodies as next generation therapeutics," *Curr Opin. Chem. Biol.*, 5:368-374 (2001).
Van Royen-Kerkhof, A., et al., "Flow cytometric determination of FcγRIIa (CD32) polymorphism," *J. Immunol. Methods*, 294:135-144 (2004).
Van Schie, R. C. A. A., et al., "Evaluation of Human FcγRIIA (CD32) and FcγRIIIB (CD16) Polymorphisms in Caucasians and African-Americans Using Salivary DNA," Clinical and Diagnostic Laboratory Immunology, 7(4):676-681 (Jul. 2000).
Van Sorge, N. M., et al., "FcγR polymorphisms: Implications for function, disease and susceptibility and immunotherapy" *Tissue Antigens*, 61:189-202 (2003).
Vasserot, A., et al., "Optimization of protein therapeutics by directed evolution," *Drug Discovery Today*, 8(3):118-126 (Feb. 2003).
Vidarte, L., et al., "Serine 132 is the C3 Covalent Attachment Point of the CH1 domain of Human IgG1" *J. Biol. Chem.*, 276(41):38217-38223 (2001).
Waldmann, T., et al., "Emerging Therapies: Spectrum of Applications of Monoclonal Antibody Therapy," *Hemotology*, 394-408 (2000).
Ward, E. S., et al., "Evidence to support the cellular mechanism involved in serum IgG homeostatis in humans" *International Immunology*, 15(2):187-195 (2003).
Warmerdam, P. A., et al., "Interaction of a human Fc gamma RIIb1 (CD32) isoform with murine and human IgG subclasses," *Int Immunol.*, 5(3):239-247 (Mar. 1993).
Wawrzynczak, E. J., et al., "Recombinant mouse monoclonal antibodies with single amino acid substitutions affecting Clq and high affinity Fc receptor binding have identical serum half-lives in the BALB/c mouse," *Mol. Immunol.*, 29(2):221-227 (Feb. 1992).
Weiner, L. M., et al., "Tunable antibodies," *Nature Biotechnology*, 23(5):556-557 (May 2005).
Weng, W., et al., "Clinical Outcome of Lymphoma Patients After Idiotype Vaccination is Correlated With Humoral Immune Response and Immunoglobulin G Fc Receptor Genotype." *J. Clin Oncol.*, 22(23)1-8 (Dec. 1, 2004).
Weng, W.. et al., "Two Immunoglobulin G Fragment C Receptor Polymorphisms Independently Predict Response to Rituximab in Patients With Follicular Lymphoma," *Journal of Clinical Oncology*, 21:3940-3947 (2003).
West, A. P., et al., "Crystal Structure and immunoglobulin G Binding Properties of the Human Major Histocompatibility Complex-Related Fc Receptor," *Biochemistry*, 39:9698-9708 (2000).
White, C., et al., "Antibody-targeted immunotherapy for treatment of malignancy," *Annu Rev Med*, 52:125-145 (2001).
Wing, M. G., et al., "Mechanism of First-Dose Cytokine-Release Syndrome by CAMPATH 1-H: Involvement of CD16 (FcγRIII) and CD11a/CD18 (LFA-1) on NK Cells," *J. Clin. Invest.*, 98(12):2819-2826 (Dec. 1996).
Wolff, E. A., et al., "Monoclonal antibody homodimers: enhanced antitumor activity in nude mice," *Cancer Res.*, 53(11):2560-2565 (Jun. 1, 1993).
Wright, A., et al., "Effect of C2-Associated carbohydrate Structure on Ig Effector Function: Studies with Chimeric Mouse-Human IgG1 Antibodies in Glycosylation Mutants of Chinese Hamster Ovary Cells" *J. of Immunology*, 160:3393-3402 (1998).
Wright, A., et al., "In vivo trafficking and catabolism of IgG1 antibodies with Fc associated carbohydrates of differing structure," *Glycobiology*, 10(12):1347-1355 (2000).
Xu, D., et al., "In Vitro Characterization of Five Humanized OKT3 Effector Function Variant Antibodies," *Cellular Immunology*, 200:16-26 (2000).
Xu, M., et al., "Molecular Cloning and Characterization of SPAP1, an Inhibitory Receptor" *Biochemical and Biophysical Research Communications*, 280:768-775 (2001).
Xu, Y., et al., "Residue at Position 331 in the IgG1 and IgG4 $C_H2$ Domains Contributes to Their Differential Ability to Bind and Activate Complement" *J. Biol. Chem.* 269(5)-3469-3474 (1994).
Yamane-Ohnuki, N., et al., "Establishment of FUT8 Knockout Chinese Hamster Ovary Cells: An Ideal Host Cell Line for Producing Completely Defucosylated Antibodies With Enhancnced Antibody-Dependent Cellular Cytotoxicity," *Biotechnology and Bioengineering* 87(5):614-622 (2004).
Zelaschi, D., et al., "Human immunoglobulin allotypes: previously unrecognized determinants and alleles defined with monoclonal antibodies," *PNAS, USA*, 80:3762-3766 (Jun. 1983).
Zhou, H., et al., "DNA-based vaccines activate innate and adaptive antitumor immunity by engaging the NKG2D receptor" *PNAS*, 102(31):10846-10851 (Aug. 2, 2005).
Zhou, J., et al., "Generation of Mutated Variants of the Human Form of the MHC Class I-related Receptor, FcRn, with Increased Affinity for Mouse Immunoglobulin G," *J. Mol. Biol.*, 332:901-913 (2003).

(56) References Cited

OTHER PUBLICATIONS

Zhu, D., et al., "A novel human immunoglobulin Fcγ-Fcε bifunctional fusion protein inhibits FcεRI-mediated degranulation," *Nat Med.,* 8(5):518-521 (May 2002).
Shinkawa, T., et al., "The absence of fucose but not the presence of galactose or bisecting N-acetylglucosamine of human IgG1 complex-type oligosaccharides shows the critical role of enhancing antibody-dependent cellular cytotoxicity", *J. Biol. Chem.,* American Society of Biolochemical Biologists, Birminghan, US, Jan. 31, 2003, pp. 3466-3473, vol. 278, No. 5.
Yamane-Ohnuki, N., et al., "Establishment of FUT8 knockout chinese hamster ovary cells: an ideal host cell line for producing completely defucosylated antibodies with enhanced antibody-dependent cellular cytotoxicity", *Biotech. and Bioeng.,* Interscience Publishers, London, GB, Sep. 5, 2004, pp. 614-622, vol. 87, No. 5.
Shields, R. L., et al. "High resolution mapping of the binding site on human IgG1 for FcgammaRI, Fcgamma RII, FcgammaRIII and FcRn and design of IgG1 variants with improved binding to the FcgammaR", *J. Biol. Chem.,* American Society of Biolochemical Biologists, Birminghan, US, Mar. 2, 2001, pp. 6591-6604, vol. 276, No. 9.
Chappel, M. S., et al., "Identification of the Fcγ receptor class I binding site in human IgG through the use of recombinant IgG1/IgG2 hybrid and point-mutated antibodies," *PNAS, USA,* 88:9036-9040 (Oct. 1991).
Clark, M. R., Antibody Engineering—Chemical Immunology, Capra JD (Editor), "IgG Effector Mechanisms," Dissertation submitted to Immunology Division of Department of Pathology at Cambridge University, UK, 1997, vol. 65, pp. 88-110.
Davis, R. S. et al., "Identification of a family of Fc receptor homologs with preferential cell expression," *PNAS, USA,* 98(17):9772-9777 (Aug. 14, 2001).
Ghetie, V., et al., "Increasing the serum persistence of an IgG fragment by random mutagenesis," *Nat. Biotechol.,* 15:637-640 (Jul. 1997).
Sensel, M. G., et al., "Amino Acid Differences in the N-Teminus of $C_H2$ Influence the Relative abilities of IgG2 and IgG3 to Activate Complement" *Mol. Immunol.,* 34(14):1019-1029 (1997).
Request for Continued Examination and Amendment and Response to Final Office Action dated Aug. 23, 2010, U.S. Appl. No. 11/544,165, 10 pages.
Restriction Requirement dated Feb. 24, 2009, U.S. Appl. No. 11/544,165, 6 pages.
Response to Restriction Requirement dated Mar. 24, 2009, U.S. Appl. No. 11/544,165, 6 pages.
Non-Final Office Action dated Jun. 24, 2009, U.S. Appl. No. 11/544,165, 14 pages.
Amendment and Response to Non-Final Office Action dated Dec. 18,2009, 18 pages.
Final Office Action dated Mar. 22, 2010, U.S. Appl. No. 11/544,165, 25 pages.
Preliminary Amendment dated Mar. 15, 2007, U.S. Appl. No. 11/686,853, 9 pages.
Preliminary Amendment dated Mar. 29, 2007, U.S. Appl. No. 11/686,853, 5 pages.
Restriction Requirement dated Jun. 23, 2009, U.S. Appl. No. 11/686,853, 8 pages.
Response to Restriction Requirement dated Jul. 20, 2009, U.S. Appl. No. 11/686,853 7 pages.
Non-Final Office Action dated Oct. 6, 2009, U.S. Appl. No. 11/686,853, 18 pages.
Amendment and Response to Non-Final Office Action dated Feb. 8, 2010, U.S. Appl. No. 11/686,853, 17 pages.
Final Office Action dated Apr. 30, 2010, U.S. Appl. No. 11/686,853, 11 pages.
Skolnick and Fetrow. From genes to protein structure and function: novel applications of computational approaches in the genomic era. Trends in Biotechnology, 2000. vol. 18, pp. 34-39.
Burgess, Shaheen, Ravera, Jaye, Donohue, and Winkles. Possible dissociation of the heparin binding and mitogenic activities of heparin binding (acidic fibroblast) growth factor 1 from its receptor binding activities by site directed mutagenesis of a single lysine residue. Journal of Cell Biology, 1990. vol. 111, pp. 2129-2138.
Lazar, Watanabe, Dalton, and Sporn. Transforming growth factor alpha: mutation of aspartic acid 47 and leucine 48 results in different biological activities. Molecular and Cellular Biology, 1988. vol. 8, pp. 1247-1252.
Rudikoff, Giusti, Cook, and Scharff. Single amino acid substitution altering antigen-binding specificity. Proceedings of the National Academy of Sciences, 1982. vol. 79, pp. 1979-1983.
Mac Callum, Martin, and Thornton. Antibody antigen interactions: contact analysis and binding site topography. Journal of Molecular Biology, 1996. vol. 262, pp. 732-745.
De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanized monoclonal antibody. Journal of Immunology, 2002. vol. 169, pp. 3076-3084.
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.
Vajdos, Adams, Breece, Presta, De Vos, and Sidhu. Comprehensive functional maps of the antigen-binding site of an anti-ErbB2 antibody obtained with shotgun scanning mutagenesis. Journal of Molecular Biology, 2002. vol. 320, pp. 415-428.
Holm, Jafari, and Sundstrom. Functional mapping and single chain construction of the anti-cytokeratin 8 monoclonal antibody TSI. Molecular Immunology, 2007. vol. 44, pp. 1075-1084.
Chen, Wiesmann, Fuh, Li, Christinger, Mc Kay, De Vos, and Lowman. Selection and analysis of an optimized anti-VEGF antibody: crystal structure of an affinity matured Fab in complex with antigen. Journal of Molecular Biology, 1999. vol. 293, pp. 865-881.
Wu, Nie, Huse, and Watkins. Humanization of a murine monoclonal antibody by simultaneous optimization of framework and CDR residues. Journal of Molecular Biology, 1999. vol. 294, pp. 151-162.

\* cited by examiner

Figure 1a. WT AC10 VL (L0) (SEQ ID NO:1)

DIVLTQSPASLAVSLGQRATISCKASQSVDFDGDSYMNWYQQKPGQPPKVLIYAASNLESGIPARFS
GSGSGTDFTLNIHPVEEEDAATYYCQQSNEDPWTFGGGTKLEIK

Figure 1b. WT AC10 VH (H0) (SEQ ID NO:2)

QIQLQQSGPEVVKPGASVKISCKASGYTFTDYYITWVKQKPGQGLEWIGWIYPGSGNTKYNEKFKGK
ATLTVDTSSSTAFMQLSSLTSEDTAVYFCANYGNYWFAYWGQGTQVTVSA

Figure 3. CD30 Binding of AC10 Variants

| AC10 Variant | SPR KD (nM) | SPR Fold KD | AlphaScreen IC50 (nM) | AlphaScreen Fold IC50 |
|---|---|---|---|---|
| H2L1 | 9.49 | 0.36 | 55.1 | 0.06 |
| H2L2 | 5.95 | 0.57 | 49.2 | 0.06 |
| H1L2 | 7.55 | 0.45 | 45.3 | 0.07 |
| H1L1 | 5.63 | 0.60 | 27.7 | 0.11 |
| H2L3 | 6.75 | 0.50 | 27.2 | 0.12 |
| H2L0 | 8.00 | 0.42 | 19.4 | 0.16 |
| H1L3 | 5.09 | 0.67 | 17.4 | 0.18 |
| H1L0 | 6.39 | 0.53 | 9.77 | 0.32 |
| H0L2 | 3.48 | 0.97 | 7.81 | 0.41 |
| H3L2 | 2.86 | 1.19 | 6.57 | 0.48 |
| H3L0 | 3.08 | 1.10 | 6.18 | 0.51 |
| H3L1 | 2.44 | 1.39 | 6.09 | 0.52 |
| H0L1 | 3.29 | 1.03 | 5.19 | 0.61 |
| H0L3 | 3.00 | 1.13 | 4.61 | 0.69 |
| H0L0 | 3.39 | 1.00 | 3.18 | 1.00 |
| H3L3 | 2.33 | 1.45 | 1.99 | 1.59 |

Figure 5a. L3 AC10 VL (SEQ ID NO:3)

DIVLTQSPDSLAVSLGERATINCKASQSVDFDGDSYMNWYQQKPGQPPKVLIYAASNLESGIPARFSGSG
SGTDFTLTINSLEAEDAATYYCQQSNEDPWTFGGGTKVEIK

Figure 5b. H3 AC10 VH (SEQ ID NO:4)

QIQLVQSGPEVKKPGASVKVSCKASGYTFTDYYITWVRQAPGQGLEWMGWIYPGSGNTKYNEKFQGRF
VFSVDTSASTAYLQISSLKAEDTAVYFCANYGNYWFAYWGQGTLVTVSS

Figure 6a. L3 AC10 Secondary Variants

| Variant | Pos (Kabat) | L3 | Sub | String Impact | Fold Prot A | Fold CD30 | Fold FcγRIIIa |
|---|---|---|---|---|---|---|---|
| L3.1 | 1 | D | A | 0 | 0.89 | 1.30 | 0.96 |
| L3.2 | 1 | D | E | 1 | 1.09 | 1.24 | 1.46 |
| L3.3 | 1 | D | N | 0 | 1.24 | 1.66 | 1.35 |
| L3.4 | 1 | D | S | 0 | 0.97 | 1.04 | 1.18 |
| L3.5 | 3 | V | Q | 0 | 1.13 | 1.32 | 1.32 |
| L3.6 | 4 | L | M | 4 | 1.65 | 1.64 | 1.21 |
| L3.7 | 25 | A | S | 6 | | | |
| L3.8 | 27a | S | D | 0 | 1.02 | 0.94 | 0.61 |
| L3.9 | 27b | V | I | 1 | 1.04 | 0.58 | 0.81 |
| L3.10 | 27c | D | L | 5 | | | |
| L3.11 | 27c | D | S | 8 | | | |
| L3.12 | 27c | D | V | 3 | 1.24 | 1.15 | 1.19 |
| L3.13 | 27d | F | D | 0 | 1.07 | 0.32 | 0.98 |
| L3.14 | 27d | F | H | 4 | 0.86 | 0.08 | 0.93 |
| L3.15 | 27d | F | Y | 5 | 1.04 | 0.63 | 1.19 |
| L3.16 | 28 | D | N | -1 | 1.10 | 1.61 | 1.18 |
| L3.17 | 30 | D | K | 4 | 1.01 | 1.21 | 1.24 |
| L3.18 | 30 | D | N | 6 | 1.09 | 1.45 | 0.94 |
| L3.19 | 30 | D | S | 4 | 1.07 | 1.13 | 0.82 |
| L3.20 | 30 | D | Y | 0 | 0.82 | 0.78 | 0.73 |
| L3.21 | 31 | S | D | 0 | 1.01 | 0.81 | 0.95 |
| L3.22 | 31 | S | T | 3 | 1.03 | 0.46 | 0.97 |
| L3.23 | 31 | S | N | -1 | 1.03 | 0.71 | 1.00 |
| L3.24 | 32 | Y | D | 0 | 1.31 | 0.46 | 1.33 |
| L3.25 | 33 | M | L | 8 | 1.38 | 1.36 | 1.37 |
| L3.26 | 34 | N | S | 0 | | | |
| L3.27 | 34 | N | A | -1 | 1.39 | 0.38 | 1.36 |
| L3.28 | 34 | N | D | -6 | 1.19 | 0.41 | 1.76 |
| L3.29 | 46 | V | H | 4 | 0.06 | 0.03 | 0.11 |
| L3.30 | 46 | V | L | 9 | 0.86 | 0.39 | 0.75 |
| L3.31 | 46 | V | R | 4 | | | |
| L3.32 | 46 | V | S | 4 | 1.05 | 0.32 | 0.90 |
| L3.33 | 50 | A | D | 6 | 0.98 | 0.26 | 0.66 |
| L3.34 | 50 | A | S | 5 | 1.01 | 0.47 | 1.20 |
| L3.35 | 50 | A | W | 2 | | | |
| L3.36 | 53 | N | S | 8 | | | |
| L3.37 | 53 | N | T | 5 | 0.99 | 1.26 | 1.01 |
| L3.38 | 54 | L | R | 1 | 1.19 | 1.46 | 1.55 |
| L3.39 | 55 | E | A | 2 | 1.01 | 0.85 | 1.32 |
| L3.40 | 55 | E | Q | 6 | 0.99 | 0.87 | 1.07 |
| L3.41 | 56 | S | T | 8 | 1.50 | 1.80 | 1.23 |
| L3.42 | 58 | I | V | 4 | 1.44 | 1.55 | 0.95 |
| L3.43 | 60 | A | D | 1 | 1.11 | 1.16 | 1.08 |
| L3.44 | 60 | A | S | 2 | 0.82 | 1.08 | 0

Figure 6a (continued). L3 AC10 Secondary Variants

| Variant | Pos (Kabat) | L3 | Sub | String Impact | Fold Prot A | Fold CD30 | Fold FcγRIIIa |
|---|---|---|---|---|---|---|---|
| L3.45 | 67 | S | P | 0 | | | |
| L3.46 | 89 | Q | H | 1 | 1.37 | 0.08 | 1.64 |
| L3.47 | 91 | S | A | 8 | | | |
| L3.48 | 91 | S | G | 9 | 0.85 | 0.29 | 0.80 |
| L3.49 | 91 | S | H | 2 | 1.20 | 0.01 | 1.32 |
| L3.50 | 91 | S | L | 8 | 1.10 | 0.02 | 1.59 |
| L3.51 | 91 | S | Y | 8 | 1.00 | 0.02 | 1.50 |
| L3.52 | 92 | N | I | 3 | | | |
| L3.53 | 92 | N | S | 2 | 3.02 | 0.48 | 1.34 |
| L3.54 | 92 | N | Y | 8 | 1.39 | 0.96 | 1.05 |
| L3.55 | 93 | E | K | 8 | 0.62 | 0.27 | 0.49 |
| L3.56 | 93 | E | N | 8 | 1.06 | 0.64 | 0.84 |
| L3.57 | 93 | E | Q | 2 | | | |
| L3.58 | 93 | E | S | 8 | 0.90 | 0.49 | 0.87 |
| L3.59 | 94 | D | A | 3 | 1.16 | 0.09 | 1.14 |
| L3.60 | 94 | D | F | 9 | 1.22 | 0.02 | 1.19 |
| L3.61 | 94 | D | H | 8 | | | |
| L3.62 | 94 | D | L | 3 | 0.87 | 0.46 | 0.79 |
| L3.63 | 94 | D | S | 1 | 1.74 | 0.57 | 1.42 |
| L3.64 | 94 | D | T | 7 | 1.24 | 0.14 | 1.16 |
| L3.65 | 96 | W | F | | 0.33 | 0.34 | 0.29 |
| L3.66 | 96 | W | I | | 0.75 | 0.00 | 0.57 |
| L3.67 | 96 | W | L | | | | |
| L3.68 | 96 | W | Y | | | | |
| L3.69 | 100 | G | P | | | | |
| L3.70 | 100 | G | Q | | | | |

Figure 6b. H3 AC10 Secondary Variants

| Variant | Position (Kabat) | H3 | Sub | String Impact | Fold Prot A | Fold CD30 |
|---|---|---|---|---|---|---|
| H3.1 | 1 | Q | E | -1 | 0.83 | 1.00 |
| H3.2 | 2 | I | L | 0 | 1.60 | 2.76 |
| H3.3 | 2 | I | M | 2 | 0.88 | 0.68 |
| H3.4 | 2 | I | V | 0 | 0.98 | 1.28 |
| H3.5 | 9 | P | A | 2 | 0.95 | 1.29 |
| H3.6 | 16 | A | T | 2 | 0.89 | 1.13 |
| H3.7 | 24 | A | V | 2 | 1.54 | 4.45 |
| H3.8 | 31 | D | G | 2 | 0.80 | 1.40 |
| H3.9 | 31 | D | S | 2 | 0.82 | 1.65 |
| H3.10 | 33 | Y | D | 2 | 0.68 | 0.07 |
| H3.11 | 33 | Y | G | 3 | 0.96 | 0.73 |
| H3.12 | 33 | Y | W | 0 | 0.84 | 0.00 |
| H3.13 | 34 | I | L | 1 | 0.96 | 1.52 |
| H3.14 | 34 | I | M | 8 | 1.05 | 1.62 |
| H3.15 | 35 | T | D | 1 | 1.55 | 0.05 |
| H3.16 | 35 | T | G | 2 | 1.03 | 0.15 |
| H3.17 | 35 | T | H | 8 | 0.86 | 0.04 |
| H3.18 | 35 | T | N | 4 | 1.07 | 0.13 |
| H3.19 | 35 | T | S | 6 | 0.88 | 1.11 |
| H3.20 | 44 | G | A | 0 | 1.20 | 2.04 |
| H3.21 | 44 | G | R | 0 | 1.36 | 2.60 |
| H3.22 | 50 | W | I | 6 | 1.25 | 0.01 |
| H3.23 | 50 | W | R | 0 | 0.99 | 0.16 |
| H3.24 | 52 | Y | N | 2 | 1.03 | 0.03 |
| H3.25 | 52 | Y | T | 1 | 1.11 | 0.06 |
| H3.26 | 52 | Y | V | 1 | 1.33 | 0.06 |
| H3.27 | 52a | P | A | 1 | 1.02 | 2.00 |
| H3.28 | 52a | P | V | 1 | 1.44 | 1.34 |
| H3.29 | 54 | S | D | 1 | 1.45 | 1.81 |
| H3.30 | 54 | S | N | 5 | 1.13 | 1.45 |
| H3.31 | 58 | K | G | 4 | | |
| H3.32 | 58 | K | I | 2 | 1.22 | 1.09 |
| H3.33 | 58 | K | N | 5 | 1.26 | 0.50 |
| H3.34 | 60 | N | A | 7 | 0.87 | 1.30 |
| H3.35 | 60 | N | P | 0 | | |
| H3.36 | 60 | N | S | 7 | 1.02 | 1.24 |
| H3.37 | 60 | N | T | 0 | 1.12 | 1.01 |
| H3.38 | 60 | N | V | 0 | 1.16 | 1.14 |
| H3.39 | 60 | N | D | 0 | 1.09 | 1.00 |
| H3.40 | 61 | E | Q | 7 | 1.51 | 1.83 |
| H3.41 | 64 | Q | T | 0 | 0.98 | 1.38 |
| H3.42 | 71 | V | L | 4 | 1.10 | 0.66 |
| H3.43 | 71 | V | M | 9 | 1.17 | 0.88 |
| H3.44 | 71 | V | R | 1 | 1.25 | 1.76 |
| H3.45 | 87 | T | M | -1 | 0.99 | 1.14 |
| H3.46 | 89 | V | M | -4 | 1.41 | 1.39 |
| H3.47 | 91 | F | H | 2 | | |
| H3.48 | 91 | F | Y | 9 | 1.32 | 1.60 |
| H3.49 | 93 | A | T | 0 | 1.47 | 0.38 |
| H3.50 | 93 | A | V | 0 | 1.01 | 1.40 |

Figure 6b (continued). H3 AC10 Secondary Variants

| Variant | Position (Kabat) | H3 | Sub | String Impact | Fold Prot A | Fold CD30 |
|---|---|---|---|---|---|---|
| H3.51 | 94 | N | A | 9 | 1.51 | 0.08 |
| H3.52 | 94 | N | H | 5 | 1.23 | 1.24 |
| H3.53 | 94 | N | K | 9 | 1.67 | 0.02 |
| H3.54 | 94 | N | R | 9 | 1.26 | 0.00 |
| H3.55 | 94 | N | T | 9 | 1.24 | 0.91 |
| H3.56 | 99 | W | Y |  | 1.26 | 0.07 |
| H3.57 | 101 | A | D |  | 1.31 | 0.53 |
| H3.58 | 101 | A | Q |  | 1.17 | 0.16 |
| H3.59 | 102 | Y | H |  | 1.69 | 1.05 |
| H3.60 | 102 | Y | S |  | 1.04 | 0.82 |
| H3.61 | 102 | Y | V |  | 1.33 | 1.21 |
| H3.62 | 102 | Y | L |  | 1.34 | 1.22 |
| H3.63 | 102 | Y | F |  | 1.18 | 1.24 |
| H3.64 | 105 | Q | R |  | 1.15 | 1.28 |

Figure 8a. L3.71 AC10 VL (SEQ ID NO:5)

EIVLTQSPDSLAVSLGERATINCKASQSVDFDGDSYLNWYQQKPGQPPKVLIYAASTLQSGVPSRFS
GSGSGTDFTLTINSLEAEDAATYYCQQSNEDPWTFGGGTKVEIK

Figure 8b. L3.72 AC10 VL (SEQ ID NO:6)

AIVLTQSPDSLAVSLGERATINCKASQSVDFDGDSYLNWYQQKPGQPPKVLIYAASTLETGVPSRFS
GSGSGTDFTLTINSLEAEDAATYYCQQSNEDPWTFGGGTKVEIK

Figure 8c. H3.68 AC10 VH (SEQ ID NO:7)

QLQLVQSGPEVKKPGASVKVSCKVSGYTFTDYYITWVRQAPGQALEWMGWIYPGSGNTKYNEKFQ
GRFVFSVDTSASTAYLQISSLKAEDTAVYFCANYGNYWFAYWGQGTLVTVSS

Figure 8d. H3.69 AC10 VH (SEQ ID NO:8)

QLQLVQSGAEVKKPGASVKVSCKVSGYTFTDYYITWVRQAPGQALEWMGWIYPGSGNTKYSQKFQ
GRFVFSVDTSASTAYLQISSLKAEDTAVYYCANYGNYWFAYWGQGTLVTVSS

Figure 8e. H3.70 AC10 VH (SEQ ID NO:9)

QLQLVQSGAEVKKPGASVKVSCKVSGYTFTSYYISWVRQAPGQALEWMGWIYAGSGNTKYSQKFQ
GRFVFSVDTSASTAYLQISSLKAEDTAVYYCANYGNYWFAYWGQGTLVTVSS

Figure 10

|  | EC50 | Fold Increase |
|---|---|---|
| H3.0_L3.0_Std | 4.1E-09 | 1 |
| PBS_CTRL |  |  |
| AC10_H3.0_L3.0 | 2.8E-09 | 1.4 |
| AC10_H3.0_L3.71 | 5.6E-09 | 0.7 |
| AC10_H3.0_L3.72 | 1.5E-09 | 2.8 |
| AC10_H3.68_L3.0 | 1.5E-09 | 2.8 |
| AC10_H3.68_L3.71 | 2.0E-09 | 2.0 |
| AC10_H3.68_L3.72 | 1.4E-09 | 2.9 |
| AC10_H3.69_L3.0 | 1.1E-09 | 3.6 |
| AC10_H3.69_L3.71 | 1.1E-09 | 3.8 |
| AC10_H3.69_L3.72 | 6.0E-10 | 6.7 |
| AC10_H3.70_L3.0 | 6.6E-10 | 6.2 |
| AC10_H3.70_L3.71 | 3.9E-10 | 10.5 |
| AC10_H3.70_L3.72 | 7.6E-10 | 5.3 |

Figure 11

| Variants | DIG-CD30 EC50 | Fold Increase | Protein A EC50 | Fold Increase | FcgRIIIaV EC50 | Fold Increase | Normalized Fold Increase CD30 | RIIIaV |
|---|---|---|---|---|---|---|---|---|
| AC10_H3L3_STD | 1.4E-10 | 1.00 | 5.6E-10 | 1.00 | 5.9E-09 | 1.00 | 1.00 | 1.00 |
| AC10_H3L3 | 8.1E-11 | 1.75 | 4.5E-10 | 1.23 | 7.9E-09 | 0.74 | 1.42 | 0.60 |
| AC10_H3.69_L3.71 | 5.8E-11 | 2.45 | 5.3E-10 | 1.05 | 1.5E-08 | 0.39 | 2.34 | 0.38 |
| AC10_H3.69_2I_L3.71 | 1.2E-10 | 1.16 | 1.2E-09 | 0.48 | 1.1E-08 | 0.52 | 2.41 | 1.08 |
| AC10_H3.69_2V_L3.71 | 1.3E-11 | 11.08 | 2.0E-10 | 2.85 | 6.3E-09 | 0.93 | 3.88 | 0.33 |
| AC10_H3.69_G44?_L3.71 | 4.6E-11 | 3.06 | 4.2E-10 | 1.32 | 5.0E-09 | 1.18 | 2.31 | 0.89 |
| AC10_H3.70_L3.71 | 1.4E-10 | 1.00 | 4.5E-10 | 1.23 | 1.3E-08 | 0.47 | 0.81 | 0.38 |
| AC10_H3.70_2I_L3.71 | 1.7E-10 | 0.83 | 5.9E-10 | 0.95 | 9.5E-09 | 0.62 | 0.87 | 0.65 |
| AC10_H3.70_2V_L3.71 | 1.4E-10 | 1.01 | 4.1E-10 | 1.37 | 7.2E-09 | 0.82 | 0.74 | 0.60 |
| AC10_H3.70_G44?_L3.71 | 2.7E-10 | 0.52 | 3.5E-10 | 1.62 | 1.3E-08 | 0.45 | 0.32 | 0.28 |
| 5F11_H0_L0 | 2.0E-09 | 0.07 | 1.5E-09 | 0.38 | 7.1E-09 | 0.83 | 0.18 | 2.19 |
| AC10_H3.69_2V_L3.0 | 3.7E-11 | 3.86 | 4.5E-10 | 1.24 | 3.2E-09 | 1.85 | 3.10 | 1.49 |
| AC10_H3.69_G44?_L3.0 | 6.7E-11 | 2.09 | 5.4E-10 | 1.04 | 5.2E-09 | 1.13 | 2.01 | 1.09 |
| AC10_H3.69_2I_L3.0 | 2.4E-11 | 5.92 | 3.5E-10 | 1.60 | 3.7E-09 | 1.58 | 3.69 | 0.98 |
| AC10_H3.69_2V_L3.0 | 2.5E-11 | 5.60 | 4.1E-10 | 1.35 | 3.9E-09 | 1.50 | 4.15 | 1.11 |
| AC10_H3.69_44G?_L3.0 | 9.9E-11 | 1.43 | 7.8E-10 | 0.71 | 9.5E-09 | 0.62 | 2.00 | 0.87 |

Figure 13a (SEQ ID NO:10)
Anti-CD30 L3.71 AC10 variable light chain (VL)
EIVLTQSPDSLAVSLGERATINCKASQSVDFDGDSYLNWYQQKPGQPPKVLIYAASTLQSGVPSRFS
GSGSGTDFTLTINSLEAEDAATYYCQQSNEDPWTFGGGTKVEIK

Figure 13b (SEQ ID NO:11)
Anti-CD30 H3.69_V2 AC10 variable heavy chain (VH)
QVQLVQSGAEVKKPGASVKVSCKVSGYTFTDYYITWVRQAPGQALEWMGWIYPGSGNTKYSQKFQ
GRFVFSVDTSASTAYLQISSLKAEDTAVYYCANYGNYWFAYWGQGTLVTVSS

Figure 15a (SEQ ID NO:12)
Kappa constant light chain (Cκ)
RTVAAPSVFIFPPSDEQLKSGTASVVCLLNNFYPREAKVQWKVDNALQSGNSQESVTEQDSKDSTYS
LSSTLTLSKADYEKHKVYACEVTHQGLSSPVTKSFNRGEC

Figure 15b (SEQ ID NO:13)
IgG1 constant heavy chain (CH1-hinge-CH2-CH3)
ASTKGPSVFPLAPSSKSTSGGTAALGCLVKDYFPEPVTVSWNSGALTSGVHTFPAVLQSSGLYSLSS
VVTVPSSSLGTQTYICNVNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTCLVKGFYPSDIAVEWESNG
QPENNYKTTPPVLDSDGSFFLYSKLTVDKSRWQQGNVFSCSVMHEALHNHYTQKSLSLSPGK

Figure 15c (SEQ ID NO:14)
IgG2 constant heavy chain (CH1-hinge-CH2-CH3)
ASTKGPSVFPLAPCSRSTSESTAALGCLVKDYFPEPVTVSWNSGALTSGVHTFPAVLQSSGLYSLSS
VVTVPSSNFGTQTYTCNVDHKPSNTKVDKTVERKCCVECPPCPAPPVAGPSVFLFPPKPKDTLMISR
TPEVTCVVVDVSHEDPEVQFNWYVDGVEVHNAKTKPREEQFNSTFRVVSVLTVVHQDWLNGKEYK
CKVSNKGLPAPIEKTISKTKGQPREPQVYTLPPSREEMTKNQVSLTCLVKGFYPSDIAVEWESNGQP
ENNYKTTPPMLDSDGSFFLYSKLTVDKSRWQQGNVFSCSVMHEALHNHYTQKSLSLSPGK

Figure 15d (SEQ ID NO:15)
IgG3 constant heavy chain (CH1-hinge-CH2-CH3)
ASTKGPSVFPLAPCSRSTSGGTAALGCLVKDYFPEPVTVSWNSGALTSGVHTFPAVLQSSGLYSLSS
VVTVPSSSLGTQTYTCNVNHKPSNTKVDKRVELKTPLGDTTHTCPRCPEPKSCDTPPPCPRCPEPKS
CDTPPPCPRCPEPKSCDTPPPCPRCPAPELLGGPSVFLFPPKPKDTLMISRTPEVTCVVVDVSHEDP
EVQFKWYVDGVEVHNAKTKPREEQYNSTFRVVSVLTVLHQDWLNGKEYKCKVSNKALPAPIEKTISK
TKGQPREPQVYTLPPSREEMTKNQVSLTCLVKGFYPSDIAVEWESSGQPENNYNTTPPMLDSDGSF
FLYSKLTVDKSRWQQGNIFSCSVMHEALHNRFTQKSLSLSPGK

Figure 15e (SEQ ID NO:16)
IgG4 constant heavy chain (CH1-hinge-CH2-CH3)
ASTKGPSVFPLAPCSRSTSESTAALGCLVKDYFPEPVTVSWNSGALTSGVHTFPAVLQSSGLYSLSS
VVTVPSSSLGTKTYTCNVDHKPSNTKVDKRVESKYGPPCPSCPAPEFLGGPSVFLFPPKPKDTLMIS
RTPEVTCVVVDVSQEDPEVQFNWYVDGVEVHNAKTKPREEQFNSTYRVVSVLTVLHQDWLNGKEY
KCKVSNKGLPSSIEKTISKAKGQPREPQVYTLPPSQEEMTKNQVSLTCLVKGFYPSDIAVEWESNGQ
PENNYKTTPPVLDSDGSFFLYSRLTVDKSRWQEGNVFSCSVMHEALHNHYTQKSLSLSLGK

Figure 15f (SEQ ID NO:17)
IgG(1/2) constant heavy chain (CH1-hinge-CH2-CH3)
ASTKGPSVFPLAPSSKSTSGGTAALGCLVKDYFPEPVTVSWNSGALTSGVHTFPAVLQSSGLYSLSS
VVTVPSSSLGTQTYICNVNHKPSNTKVDKKVEPKSCDKTHTCPPCPAPPVAGPSVFLFPPKPKDTLMI
SRTPEVTCVVVDVSHEDPEVQFNWYVDGVEVHNAKTKPREEQFNSTFRVVSVLTVVHQDWLNGKE
YKCKVSNKGLPAPIEKTISKTKGQPREPQVYTLPPSREEMTKNQVSLTCLVKGFYPSDIAVEWESNG
QPENNYKTTPPMLDSDGSFFLYSKLTVDKSRWQQGNVFSCSVMHEALHNHYTQKSLSLSPGK

Figure 15g (SEQ ID NO:18)
IgG(1/2) ELLGG constant heavy chain (CH1-hinge-CH2-CH3)
ASTKGPSVFPLAPSSKSTSGGTAALGCLVKDYFPEPVTVSWNSGALTSGVHTFPAVLQSSGLYSLSS
VVTVPSSSLGTQTYICNVNHKPSNTKVDKKVEPKSCDKTHTCPPCPAPELLGGPSVFLFPPKPKDTL
MISRTPEVTCVVVDVSHEDPEVQFNWYVDGVEVHNAKTKPREEQFNSTFRVVSVLTVVHQDWLNGK
EYKCKVSNKGLPAPIEKTISKTKGQPREPQVYTLPPSREEMTKNQVSLTCLVKGFYPSDIAVEWESNG
QPENNYKTTPPMLDSDGSFFLYSKLTVDKSRWQQGNVFSCSVMHEALHNHYTQKSLSLSPGK

Figure 16a (SEQ ID NO:19)
Anti-CD30 light chain (VL-CL)
EIVLTQSPDSLAVSLGERATINCKASQSVDFDGDSYLNWYQQKPGQPPKVLIYAASTLQSGVPSRFS
GSGSGTDFTLTINSLEAEDAATYYCQQSNEDPWTFGGGTKVEIKRTVAAPSVFIFPPSDEQLKSGTAS
VVCLLNNFYPREAKVQWKVDNALQSGNSQESVTEQDSKDSTYSLSSTLTLSKADYEKHKVYACEVT
HQGLSSPVTKSFNRGEC

Figure 16b (SEQ ID NO:20)
Anti-CD30 heavy chain (VH-CH1-hinge-CH2-CH3)
QVQLVQSGAEVKKPGASVKVSCKVSGYTFTDYYITWVRQAPGQALEWMGWIYPGSGNTKYSQKFQ
GRFVFSVDTSASTAYLQISSLKAEDTAVYYCANYGNYWFAYWGQGTLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPDVFLFPPKPKDTLMISRTPEVTCVVVDV
SHEDPEVQFNWYVDGVEVHNAKTKPREEQFNSTFRVVSVLTVVHQDWLNGKEYKCKVSNKALPAP
EEKTISKTKGQPREPQVYTLPPSREEMTKNQVSLTCLVKGFYPSDIAVEWESNGQPENNYKTTPPML
DSDGSFFLYSKLTVDKSRWQQGNVFSCSVMHEALHNHYTQKSLSLSPGK

Figure 17

Anti-CD30 IgG(1/2) ELLGG Variants

| NNO Modification(s) | Isotypic Modification(s) | Isotypic Modification(s) |
|---|---|---|
| | (All are IgG(1/2) ELLGG) | |
| | γ1(118-225) / P233E/V234L/A235L/-236G | |
| S239D/I332E | γ1(118-225) / P233E/V234L/A235L/-236G | |
| S239D/I332E/K246H | γ1(118-225) / P233E/V234L/A235L/-236G | |
| S239D/I332E/S267E | γ1(118-225) / P233E/V234L/A235L/-236G | |
| S239D/I332E/H268D | γ1(118-225) / P233E/V234L/A235L/-236G | |
| S239D/I332E/H268E | γ1(118-225) / P233E/V234L/A235L/-236G | |
| S239D/I332E/S298A | γ1(118-225) / P233E/V234L/A235L/-236G | |
| S239D/I332E/S324G | γ1(118-225) / P233E/V234L/A235L/-236G | |
| S239D/I332E/K326T | γ1(118-225) / P233E/V234L/A235L/-236G | |
| S239D/I332E/G327D | γ1(118-225) / P233E/V234L/A235L/-236G | |
| S239D/I332E/A330Y | γ1(118-225) / P233E/V234L/A235L/-236G | |
| S239D/I332E/K334T | γ1(118-225) / P233E/V234L/A235L/-236G | |
| S239D/I332E/H268D/S324G | γ1(118-225) / P233E/V234L/A235L/-236G | |
| S239D/I332E/K326E/A330Y | γ1(118-225) / P233E/V234L/A235L/-236G | |
| S239D/I332E/K246H/T260H | γ1(118-225) / P233E/V234L/A235L/-236G | |
| S239D/I332E/S324I | γ1(118-225) / P233E/V234L/A235L/-236G | |
| | γ1(118-225) / P233E/V234L/A235L/-236G | G327A |
| G327D | γ1(118-225) / P233E/V234L/A235L/-236G | |
| S239D/I332E | γ1(118-225) / P233E/V234L/A235L/-236G | G327A |
| S239D/I332E/K246H | γ1(118-225) / P233E/V234L/A235L/-236G | G327A |
| S239D/I332E/K246H/G327D | γ1(118-225) / P233E/V234L/A235L/-236G | |
| S239D/I332E/S267E | γ1(118-225) / P233E/V234L/A235L/-236G | G327A |
| S239D/I332E/S267E/G327D | γ1(118-225) / P233E/V234L/A235L/-236G | |
| S239D/I332E/H268D | γ1(118-225) / P233E/V234L/A235L/-236G | G327A |
| S239D/I332E/H268D/G327D | γ1(118-225) / P233E/V234L/A235L/-236G | |
| S239D/I332E/H268E | γ1(118-225) / P233E/V234L/A235L/-236G | G327A |
| S239D/I332E/H268E/G327D | γ1(118-225) / P233E/V234L/A235L/-236G | |
| S239D/I332E/S298A | γ1(118-225) / P233E/V234L/A235L/-236G | G327A |
| S239D/I332E/S298A/G327D | γ1(118-225) / P233E/V234L/A235L/-236G | |
| S239D/I332E/S324G | γ1(118-225) / P233E/V234L/A235L/-236G | G327A |
| S239D/I332E/S324G/G327D | γ1(118-225) / P233E/V234L/A235L/-236G | |
| S239D/I332E/K326T | γ1(118-225) / P233E/V234L/A235L/-236G | G327A |
| S239D/I332E/K326T/G327D | γ1(118-225) / P233E/V234L/A235L/-236G | |
| S239D/I332E/A330Y | γ1(118-225) / P233E/V234L/A235L/-236G | G327A |
| S239D/I332E/A330Y/G327D | γ1(118-225) / P233E/V234L/A235L/-236G | |
| S239D/I332E/K334T | γ1(118-225) / P233E/V234L/A235L/-236G | G327A |
| S239D/I332E/K334T/G327D | γ1(118-225) / P233E/V234L/A235L/-236G | |
| S239D/I332E/H268D/S324G | γ1(118-225) / P233E/V234L/A235L/-236G | G327A |
| S239D/I332E/H268D/S324G/G327D | γ1(118-225) / P233E/V234L/A235L/-236G | |
| S239D/I332E/K326E/A330Y | γ1(118-225) / P233E/V234L/A235L/-236G | G327A |
| S239D/I332E/K326E/A330Y/G327D | γ1(118-225) / P233E/V234L/A235L/-236G | |
| S239D/I332E/K246H/T260H | γ1(118-225) / P233E/V234L/A235L/-236G | G327A |
| S239D/I332E/K246H/T260H/G327D | γ1(118-225) / P233E/V234L/A235L/-236G | |
| S239D/I332E/S324I | γ1(118-225) / P233E/V234L/A235L/-236G | G327A |
| S239D/I332E/S324I/G327D | γ1(118-225) / P233E/V234L/A235L/-236G | |
| S239D/I332E/V284D | γ1(118-225) / P233E/V234L/A235L/-236G | |
| S239D/I332E/V284E | γ1(118-225) / P233E/V234L/A235L/-236G | |
| S239D/I332E/M428L | γ1(118-225) / P233E/V234L/A235L/-236G | |
| S239D/I332E/T250Q/M428L | γ1(118-225) / P233E/V234L/A235L/-236G | |
| S239D/I332E/V284D | γ1(118-225) / P233E/V234L/A235L/-236G | G327A |
| S239D/I332E/V284D/G327D | γ1(118-225) / P233E/V234L/A235L/-236G | |
| S239D/I332E/V284E | γ1(118-225) / P233E/V234L/A235L/-236G | G327A |
| S239D/I332E/V284E/G327D | γ1(118-225) / P233E/V234L/A235L/-236G | |

Figure 19

| Amino Acid Modification | Variable Region | Constant Region | AlphaScreen IC50 (M) | Fold V158 FcγRIIIa |
|---|---|---|---|---|
| None (WT IgG1) | H3.69_V2_L3.71 AC10 | IgG1 | 1.3E-07 | 1.0 |
| I332E | H3.69_L3.71 AC10 | IgG1 | 1.9E-08 | 6.8 |
| I332E | H3.69_L3.71 AC10 | IgG1 | 3.56E-09 | 8.7 |
| S239D/I332E | H3.69_L3.71 AC10 | IgG1 | 5.1E-09 | 25.4 |
| S239D/I332E | H3.69_L3.71 AC10 | IgG1 | 5.31E-10 | 58.6 |
| None (IgG(1/2) ELLGG) | H3.69_V2_L3.71 AC10 | IgG(1/2) ELLGG | 3.8E-08 | 0.8 |
| S239/I332E | H3.69_V2_L3.71 AC10 | IgG(1/2) ELLGG | 8.1E-09 | 16.0 |
| S239/I332E/K334T | H3.69_V2_L3.71 AC10 | IgG(1/2) ELLGG | 2.8E-08 | 4.7 |
| S239D/I332E/H268E | H3.69_V2_L3.71 AC10 | IgG(1/2) ELLGG | 8.82E-10 | 35.3 |
| S239/I332E/H268D | H3.69_V2_L3.71 AC10 | IgG(1/2) ELLGG | 4.7E-09 | 27.4 |
| S239D/I332E/A330Y | H3.69_V2_L3.71 AC10 | IgG(1/2) ELLGG | 5.2E-08 | 2.5 |
| S239D/I332E/S267E | H3.69_V2_L3.71 AC10 | IgG(1/2) ELLGG | 7.2E-08 | 1.8 |
| S239/I332E/M428L | H3.69_V2_L3.71 AC10 | IgG(1/2) ELLGG | 1.5E-08 | 8.4 |
| S239D/I332E/K326T | H3.69_V2_L3.71 AC10 | IgG(1/2) ELLGG | 5.26E-09 | 5.9 |
| S239D/I332E/S324G | H3.69_V2_L3.71 AC10 | IgG(1/2) ELLGG | 8.93E-09 | 3.5 |
| S239D/I332E/S298A | H3.69_V2_L3.71 AC10 | IgG(1/2) ELLGG | 1.28E-09 | 24.4 |
| S239/I332E/H268D/S324G | H3.69_V2_L3.71 AC10 | IgG(1/2) ELLGG | 2.1E-08 | 6.1 |
| S239D/I332E/A330Y/K326E | H3.69_V2_L3.71 AC10 | IgG(1/2) ELLGG | 4.0E-09 | 32.8 |
| S239D/I332E/K246H/T260H | H3.69_V2_L3.71 AC10 | IgG(1/2) ELLGG | 5.79E-09 | 5.4 |
| S239D/I332E/K246H/S324I | H3.69_V2_L3.71 AC10 | IgG(1/2) ELLGG | 1.07E-08 | 2.9 |
| G327A | H3.69_V2_L3.71 AC10 | IgG(1/2) ELLGG | 6.4E-08 | 2.0 |
| G327D | H3.69_V2_L3.71 AC10 | IgG(1/2) ELLGG | 1.9E-07 | 0.7 |
| S239/I332E/G327A | H3.69_V2_L3.71 AC10 | IgG(1/2) ELLGG | 6.9E-09 | 18.7 |
| S239/I332E/G327D | H3.69_V2_L3.71 AC10 | IgG(1/2) ELLGG | 1.7E-08 | 7.7 |
| S239/I332E/G327A/H268E | H3.69_V2_L3.71 AC10 | IgG(1/2) ELLGG | 3.9E-10 | 330.1 |
| S239/I332E/G327D/H268E | H3.69_V2_L3.71 AC10 | IgG(1/2) ELLGG | 2.1E-09 | 61.7 |
| S239/I332E/G327A/H268D | H3.69_V2_L3.71 AC10 | IgG(1/2) ELLGG | 1.4E-09 | 90.8 |
| S239/I332E/G327D/H268D | H3.69_V2_L3.71 AC10 | IgG(1/2) ELLGG | 4.9E-09 | 26.7 |
| S239/I332E/S298A/G327A | H3.69_V2_L3.71 AC10 | IgG(1/2) ELLGG | 2.4E-09 | 55.2 |
| S239/I332E/S298A/G327D | H3.69_V2_L3.71 AC10 | IgG(1/2) ELLGG | 7.6E-09 | 17.0 |
| S239/I332E/G327A/K246H | H3.69_V2_L3.71 AC10 | IgG(1/2) ELLGG | 4.4E-09 | 29.4 |
| S239/I332E/G327D/K246H | H3.69_V2_L3.71 AC10 | IgG(1/2) ELLGG | 2.2E-08 | 5.9 |
| S239/I332E/A330Y/K326E/G327A | H3.69_V2_L3.71 AC10 | IgG(1/2) ELLGG | 1.3E-09 | 102.9 |

Figure 22. Cell Lines

| Cell Line | Lineage | Relative expression |
|---|---|---|
| L540 | HD-T | 183 |
| L540cy | HD-T | 120 |
| HDLM2 | HD-T | 156 |
| L428 | HD-B | 67 |
| KM-H2 | HD-B | 33 |
| MY-Z | HD-M | ? |
| Karpas 299 | ALCL | 158 |

HD-T = T-cell like; HD-B B-cell like; HD-M = myelomonocytoid

Relative expression as compared to Daudi cells

Adapted from Wahl et al, Cancer Res. 2002

XmAb™2513 Target:Effector Cell Ratio Titration

ADCC with low CD30 copy number cell line

Figure 25. Binding of H0L0 AC10 and 2513 to human and macaque cell lines

Figure 26. Increased FcγR-mediated antiproliferation

SEQUENCE LISTING

```
<160> NUMBER OF SEQ ID NOS: 35

<210> SEQ ID NO 1
<211> LENGTH: 111
<212> TYPE: PRT
<213> ORGANISM: Mus musculus

<400> SEQUENCE: 1

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
                20                  25                  30

Gly Asp Ser Tyr Met Asn Trp Tyr Gln Gln Lys Pro Gly Gln Pro Pro
            35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Trp Thr Phe Gly Gly Gly Thr Lys Leu Glu Ile Lys
                100                 105                 110

<210> SEQ ID NO 2
<211> LENGTH: 117
<212> TYPE: PRT
<213> ORGANISM: Mus musculus

<400> SEQUENCE: 2
```

Gln Ile Gln Leu Gln Gln Ser Gly Pro Glu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Thr Trp Val Lys Gln Lys Pro Gly Gln Gly Leu Glu Trp Ile
                35                  40                  45

Gly Trp Ile Tyr Pro Gly Ser Gly Asn Thr Lys Tyr Asn Glu Lys Phe
        50                  55                  60

Lys Gly Lys Ala Thr Leu Thr Val Asp Thr Ser Ser Thr Ala Phe
65                  70                  75                  80

Met Gln Leu Ser Ser Leu Thr Ser Glu Asp Thr Ala Val Tyr Phe Cys
                85                  90                  95

Ala Asn Tyr Gly Asn Tyr Trp Phe Ala Tyr Trp Gly Gln Gly Thr Gln
                100                 105                 110

Val Thr Val Ser Ala
            115

<210> SEQ ID NO 3
<211> LENGTH: 111
<212> TYPE: PRT
<213> ORGANISM: Artificial Sequence
<220> FEATURE:
<223> OTHER INFORMATION: L3 AC10 VL

<400> SEQUENCE: 3

Asp Ile Val Leu Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Gln Gln Ser Asn
                85                  90                  95

Glu Asp Pro Trp Thr Phe Gly Gly Gly Thr Lys Val Glu Ile Lys
                100                 105                 110

<210> SEQ ID NO 4
<211> LENGTH: 117
<212> TYPE: PRT
<213> ORGANISM: Artificial Sequence
<220> FEATURE:
<223> OTHER INFORMATION: H3 AC10 VH

<400> SEQUENCE: 4

Gln Ile Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
                35                  40                  45

Gly Trp Ile Tyr Pro Gly Ser Gly Asn Thr Lys Tyr Asn Glu Lys Phe
        50                  55                  60

Gln Gly Arg Phe Val Phe Ser Val Asp Thr Ser Ala Ser Thr Ala Tyr
65                  70                  75                  80

Leu Gln Ile Ser Ser Leu Lys Ala Glu Asp Thr Ala Val Tyr Phe Cys
            85                  90                  95

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 5
<211> LENGTH: 111
<212> TYPE: PRT
<213> ORGANISM: Artificial Sequence
<220> FEATURE:
<223> OTHER INFORMATION: L3.71 AC10 VL

<400> SEQUENCE: 5

Glu Ile Val Leu Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Tyr Leu Asn Trp Tyr Gln Gln Lys Pro Gly Gln Pro Pro
        35                  40                  45

Lys Val Leu Ile Tyr Ala Ala Ser Thr Leu Gln Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Gln Gln Ser Asn
                85                  90                  95

Glu Asp Pro Trp Thr Phe Gly Gly Gly Thr Lys Val Glu Ile Lys
            100                 105                 110

<210> SEQ ID NO 6
<211> LENGTH: 111
<212> TYPE: PRT
<213> ORGANISM: Artificial Sequence
<220> FEATURE:
<223> OTHER INFORMATION: L3.72 AC10 VL

<400> SEQUENCE: 6

Ala Ile Val Leu Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Tyr Leu Asn Trp Tyr Gln Gln Lys Pro Gly Gln Pro Pro
        35                  40                  45

Lys Val Leu Ile Tyr Ala Ala Ser Thr Leu Glu Thr Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Gln Gln Ser Asn
                85                  90                  95

Glu Asp Pro Trp Thr Phe Gly Gly Gly Thr Lys Val Glu Ile Lys
            100                 105                 110

<210> SEQ ID NO 7
<211> LENGTH: 117
<212> TYPE: PRT
<213> ORGANISM: Artificial Sequence
<220> FEATURE:
<223> OTHER INFORMATION: H3.68 AC10 VH -continued

<400> SEQUENCE: 7

Gln Leu Gln Leu Val Gln Ser Gly Pro Glu Val Lys Lys Pro Gly Ala
1               5                   10                  15

Ser Val Lys Val Ser Cys Lys Val Ser Gly Tyr Thr Phe Thr Asp Tyr
            20                  25                  30

Tyr Ile Thr Trp Val Arg Gln Ala Pro Gly Gln Ala Leu Glu Trp Met
        35                  40                  45

Gly Trp Ile Tyr Pro Gly Ser Gly Asn Thr Lys Tyr Asn Glu Lys Phe
    50                  55                  60

Gln Gly Arg Phe Val Phe Ser Val Asp Thr Ser Ala Ser Thr Ala Tyr
65                  70                  75                  80

Leu Gln Ile Ser Ser Leu Lys Ala Glu Asp Thr Ala Val Tyr Phe Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 8
<211> LENGTH: 117
<212> TYPE: PRT
<213> ORGANISM: Artificial Sequence
<220> FEATURE:
<223> OTHER INFORMATION: H3.69 AC10 VH

<400> SEQUENCE: 8

Gln Leu Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Asp Tyr
            20                  25                  30

Tyr Ile Thr Trp Val Arg Gln Ala Pro Gly Gln Ala Leu Glu Trp Met
        35                  40                  45

Gly Trp Ile Tyr Pro Gly Ser Gly Asn Thr Lys Tyr Ser Gln Lys Phe
    50                  55                  60

Gln Gly Arg Phe Val Phe Ser Val Asp Thr Ser Ala Ser Thr Ala Tyr
65                  70                  75                  80

Leu Gln Ile Ser Ser Leu Lys Ala Glu Asp Thr Ala Val Tyr Tyr Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 9
<211> LENGTH: 117
<212> TYPE: PRT
<213> ORGANISM: Artificial Sequence
<220> FEATURE:
<223> OTHER INFORMATION: H3.70 AC10 VH

<400> SEQUENCE: 9

Gln Leu Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Ser Tyr
            20                  25                  30

Tyr Ile Ser Trp Val Arg Gln Ala Pro Gly Gln Ala Leu Glu Trp Met
        35                  40                  45

Gly Trp Ile Tyr Ala Gly Ser Gly Asn Thr Lys Tyr Ser Gln Lys Phe
            50                  55                  60

Gln Gly Arg Phe Val Phe Ser Val Asp Thr Ser Ala Ser Thr Ala Tyr
65                  70                  75                  80

Leu Gln Ile Ser Ser Leu Lys Ala Glu Asp Thr Ala Val Tyr Tyr Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 10
<211> LENGTH: 111
<212> TYPE: PRT
<213> ORGANISM: Artificial Sequence
<220> FEATURE:
<223> OTHER INFORMATION: Anti-CD30 L3.71 AC10 variable light chain (VL)

<400> SEQUENCE: 10

Glu Ile Val Leu Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Tyr Leu Asn Trp Tyr Gln Gln Lys Pro Gly Gln Pro Pro
        35                  40                  45

Lys Val Leu Ile Tyr Ala Ala Ser Thr Leu Gln Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Gln Gln Ser Asn
                85                  90                  95

Glu Asp Pro Trp Thr Phe Gly Gly Gly Thr Lys Val Glu Ile Lys
            100                 105                 110

<210> SEQ ID NO 11
<211> LENGTH: 117
<212> TYPE: PRT
<213> ORGANISM: Artificial Sequence
<220> FEATURE:
<223> OTHER INFORMATION: Anti-CD30 H3.69_V2 AC10 variable heavy chain
      (VH)

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Asp Tyr
            20                  25                  30

Tyr Ile Thr Trp Val Arg Gln Ala Pro Gly Gln Ala Leu Glu Trp Met
        35                  40                  45

Gly Trp Ile Tyr Pro Gly Ser Gly Asn Thr Lys Tyr Ser Gln Lys Phe
    50                  55                  60

Gln Gly Arg Phe Val Phe Ser Val Asp Thr Ser Ala Ser Thr Ala Tyr
65                  70                  75                  80

Leu Gln Ile Ser Ser Leu Lys Ala Glu Asp Thr Ala Val Tyr Tyr Cys
                85                  90                  95

Ala Asn Tyr Gly Asn Tyr Trp Phe Ala Tyr Trp Gly Gln Gly Thr Leu
            100                 105                 110

```
Val Thr Val Ser Ser
        115

<210> SEQ ID NO 12
<211> LENGTH: 107
<212> TYPE: PRT
<213> ORGANISM: Homo sapiens

<400> SEQUENCE: 12

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 13
<211> LENGTH: 330
<212> TYPE: PRT
<213> ORGANISM: Homo sapiens

<400> SEQUENCE: 13

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 14
<211> LENGTH: 326
<212> TYPE: PRT
<213> ORGANISM: Homo sapiens

<400> SEQUENCE: 14

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255
```

```
Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 15
<211> LENGTH: 377
<212> TYPE: PRT
<213> ORGANISM: Homo sapiens

<400> SEQUENCE: 15

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
        130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
```

```
            290                 295                 300
Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
                340                 345                 350

Phe Ser Cys Ser Val Met His Glu Ala Leu His Asn Arg Phe Thr Gln
                355                 360                 365

Lys Ser Leu Ser Leu Ser Pro Gly Lys
                370                 375

<210> SEQ ID NO 16
<211> LENGTH: 327
<212> TYPE: PRT
<213> ORGANISM: Homo sapiens

<400> SEQUENCE: 16

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285
```

```
Arg Leu Thr Val Asp Lys Ser Arg Trp Gln Glu Gly Asn Val Phe Ser
            290                 295                 300
Cys Ser Val Met His Glu Ala Leu His Asn His Tyr Thr Gln Lys Ser
305                 310                 315                 320
Leu Ser Leu Ser Leu Gly Lys
                325
```

```
<210> SEQ ID NO 17
<211> LENGTH: 329
<212> TYPE: PRT
<213> ORGANISM: Artificial Sequence
<220> FEATURE:
<223> OTHER INFORMATION: IgG(1/2) constant heavy chain
      (CH1-hinge-CH2-CH3)

<400> SEQUENCE: 17

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Pro Val Ala Gly Pro Ser Val Phe Leu Phe Pro Pro Lys
        115                 120                 125
Pro Lys Asp Thr Leu Met Ile Ser Arg Thr Pro Glu Val Thr Cys Val
    130                 135                 140
Val Val Asp Val Ser His Glu Asp Pro Glu Val Gln Phe Asn Trp Tyr
145                 150                 155                 160
Val Asp Gly Val Glu Val His Asn Ala Lys Thr Lys Pro Arg Glu Glu
                165                 170                 175
Gln Phe Asn Ser Thr Phe Arg Val Val Ser Val Leu Thr Val Val His
            180                 185                 190
Gln Asp Trp Leu Asn Gly Lys Glu Tyr Lys Cys Lys Val Ser Asn Lys
        195                 200                 205
Gly Leu Pro Ala Pro Ile Glu Lys Thr Ile Ser Lys Thr Lys Gly Gln
    210                 215                 220
Pro Arg Glu Pro Gln Val Tyr Thr Leu Pro Pro Ser Arg Glu Glu Met
225                 230                 235                 240
Thr Lys Asn Gln Val Ser Leu Thr Cys Leu Val Lys Gly Phe Tyr Pro
                245                 250                 255
Ser Asp Ile Ala Val Glu Trp Glu Ser Asn Gly Gln Pro Glu Asn Asn
            260                 265                 270
Tyr Lys Thr Thr Pro Pro Met Leu Asp Ser Asp Gly Ser Phe Phe Leu
        275                 280                 285
Tyr Ser Lys Leu Thr Val Asp Lys Ser Arg Trp Gln Gln Gly Asn Val
    290                 295                 300
Phe Ser Cys Ser Val Met His Glu Ala Leu His Asn His Tyr Thr Gln
305                 310                 315                 320
```

Lys Ser Leu Ser Leu Ser Pro Gly Lys
            325

<210> SEQ ID NO 18
<211> LENGTH: 330
<212> TYPE: PRT
<213> ORGANISM: Artificial Sequence
<220> FEATURE:
<223> OTHER INFORMATION: IgG(1/2) ELLGG constant heavy chain
      (CH1-hinge-CH2-CH3)

<400> SEQUENCE: 18

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Val
            180                 185                 190

His Gln Asp Trp Leu Asn Gly Lys Glu Tyr Lys Cys Lys Val Ser Asn
        195                 200                 205

Lys Gly Leu Pro Ala Pro Ile Glu Lys Thr Ile Ser Lys Thr Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Met Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 19
<211> LENGTH: 218
<212> TYPE: PRT
<213> ORGANISM: Artificial Sequence
<220> FEATURE:
<223> OTHER INFORMATION: Anti-CD30 light chain (VL-CL)

<400> SEQUENCE: 19

```
Glu Ile Val Leu Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Tyr Leu Asn Trp Tyr Gln Gln Lys Pro Gly Gln Pro Pro
        35                  40                  45

Lys Val Leu Ile Tyr Ala Ala Ser Thr Leu Gln Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Gln Gln Ser Asn
                85                  90                  95

Glu Asp Pro Trp Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 20
<211> LENGTH: 447
<212> TYPE: PRT
<213> ORGANISM: Artificial Sequence
<220> FEATURE:
<223> OTHER INFORMATION: Anti-CD30 heavy chain (VH-CH1-hinge-CH2-CH3)

<400> SEQUENCE: 20

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Asp Tyr
            20                  25                  30

Tyr Ile Thr Trp Val Arg Gln Ala Pro Gly Gln Ala Leu Glu Trp Met
        35                  40                  45

Gly Trp Ile Tyr Pro Gly Ser Gly Asn Thr Lys Tyr Ser Gln Lys Phe
    50                  55                  60

Gln Gly Arg Phe Val Phe Ser Val Asp Thr Ser Ala Ser Thr Ala Tyr
65                  70                  75                  80

Leu Gln Ile Ser Ser Leu Lys Ala Glu Asp Thr Ala Val Tyr Tyr Cys
                85                  90                  95
```

```
Ala Asn Tyr Gly Asn Tyr Trp Phe Ala Tyr Trp Gly Gln Gly Thr Leu
                100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Asp Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Ala Leu Pro Ala Pro Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 21
<211> LENGTH: 5
<212> TYPE: PRT
<213> ORGANISM: Artificial Sequence
<220> FEATURE:
<223> OTHER INFORMATION: Peptide linkers

<400> SEQUENCE: 21

Gly Ser Gly Gly Ser
1               5
```

```
<210> SEQ ID NO 22
<211> LENGTH: 5
<212> TYPE: PRT
<213> ORGANISM: Artificial Sequence
<220> FEATURE:
<223> OTHER INFORMATION: Peptide linkers

<400> SEQUENCE: 22

Gly Gly Gly Gly Ser
1               5

<210> SEQ ID NO 23
<211> LENGTH: 5
<212> TYPE: PRT
<213> ORGANISM: Mus musculus

<400> SEQUENCE: 23

Asp Tyr Tyr Ile Thr
1               5

<210> SEQ ID NO 24
<211> LENGTH: 16
<212> TYPE: PRT
<213> ORGANISM: Mus musculus

<400> SEQUENCE: 24

Trp Ile Tyr Pro Gly Ser Gly Asn Thr Lys Tyr Asn Glu Lys Phe Lys
1               5                   10                  15

<210> SEQ ID NO 25
<211> LENGTH: 4
<212> TYPE: PRT
<213> ORGANISM: Mus musculus

<400> SEQUENCE: 25

Trp Phe Ala Tyr
1

<210> SEQ ID NO 26
<211> LENGTH: 14
<212> TYPE: PRT
<213> ORGANISM: Mus musculus

<400> SEQUENCE: 26

Ala Ser Gln Ser Val Asp Phe Asp Gly Asp Ser Tyr Met Asn
1               5                   10

<210> SEQ ID NO 27
<211> LENGTH: 7
<212> TYPE: PRT
<213> ORGANISM: Mus musculus

<400> SEQUENCE: 27

Ala Ala Ser Asn Leu Glu Ser
1               5

<210> SEQ ID NO 28
<211> LENGTH: 8
<212> TYPE: PRT
<213> ORGANISM: Mus musculus

<400> SEQUENCE: 28

Gln Gln Ser Asn Glu Asp Pro Trp
1               5
```

<210> SEQ ID NO 29
<211> LENGTH: 16
<212> TYPE: PRT
<213> ORGANISM: Artificial Sequence
<220> FEATURE:
<223> OTHER INFORMATION: H3 AC10 VH CDR2

<400> SEQUENCE: 29

Trp Ile Tyr Pro Gly Ser Gly Asn Thr Lys Tyr Asn Glu Lys Phe Gln
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: H3.69 AC10 VH CDR2

<400> SEQUENCE: 30

Trp Ile Tyr Pro Gly Ser Gly Asn Thr Lys Tyr Ser Gln Lys Phe Gln
1               5                   10                  15

<210> SEQ ID NO 31
<211> LENGTH: 5
<212> TYPE: PRT
<213> ORGANISM: Artificial Sequence
<220> FEATURE:
<223> OTHER INFORMATION: H3.70 AC10 VH CDR1

<400> SEQUENCE: 31

Ser Tyr Tyr Ile Ser
1               5

<210> SEQ ID NO 32
<211> LENGTH: 16
<212> TYPE: PRT
<213> ORGANISM: Artificial Sequence
<220> FEATURE:
<223> OTHER INFORMATION: H3.70 AC10 VH CDR2

<400> SEQUENCE: 32

Trp Ile Tyr Ala Gly Ser Gly Asn Thr Lys Tyr Ser Gln Lys Phe Gln
1               5                   10                  15

<210> SEQ ID NO 33
<211> LENGTH: 14
<212> TYPE: PRT
<213> ORGANISM: Artificial Sequence
<220> FEATURE:
<223> OTHER INFORMATION: L3.71 AC10 VL CDR1

<400> SEQUENCE: 33

Ala Ser Gln Ser Val Asp Phe Asp Gly Asp Ser Tyr Leu Asn
1               5                   10

<210> SEQ ID NO 34
<211> LENGTH: 7
<212> TYPE: PRT
<213> ORGANISM: Artificial Sequence
<220> FEATURE:
<223> OTHER INFORMATION: L3.71 AC10 VL CDR2

<400> SEQUENCE: 34

Ala Ala Ser Thr Leu Gln Ser
1               5

```
<210> SEQ ID NO 35
<211> LENGTH: 7
<212> TYPE: PRT
<213> ORGANISM: Artificial Sequence
<220> FEATURE:
<223> OTHER INFORMATION: L3.72 AC10 VL CDR2

<400> SEQUENCE: 35

Ala Ala Ser Thr Leu Glu Thr
1               5
```

OPTIMIZED ANTI-CD30 ANTIBODIES

This application is a divisional of U.S. Patent Application No. 12/089,384, filed Apr. 4, 2008, that issued as U.S. Patent No. 7,973,136 on Jul. 5, 2011, and which is the national stage application of PCT Patent Application No. PCT/US2006/039306, filed Oct. 6, 2006, and which claims benefit under 35 U.S. C. §119(e) to U.S. Provisional Patent Application Nos. 60/776,598, filed Feb. 24, 2006; 60/737,998, filed Nov. 11, 2005; 60/724,624, filed Oct. 6, 2005; 60/750,697 filed Dec. 12, 2005 and 60/745,536 filed Apr. 25, 2006, all of which are incorporated herein by reference in their entireties.

FIELD OF THE INVENTION

The present invention relates to optimized proteins that target CD30, and their application, particularly for therapeutic purposes.

BACKGROUND OF THE INVENTION

CD30 is a 120-kDa type I transmembrane protein that is expressed on activated B and T lymphocytes in healthy individuals. Expression of CD30 has been observed in several nonmalignant disorders, including lymphomatoid papulosis, and in virally transformed B and T cells. CD30 is also expressed in several types of malignancies, including Hodgkin's disease, anaplastic large-cell lymphoma (ALCL), immunoblastic lymphoma, multiple myeloma, adult T-cell lymphoma leukemia, mycosis fungoides, germ-cell malignancies, and thyroid carcinoma. Soluble CD30 is detected at low levels in the sera of healthy individuals and in individuals infected with one of several different viruses, including hepatitis B and C, human immunodeficiency virus (HIV), and Epstein-Barr virus (EBV), and at higher levels, in individuals with systemic lupus erythematosis, rheumatoid arthritis, and Hashimoto's thyroiditis. Elevated levels of soluble CD30 in sera from patients who have anaplastic large-cell lymphoma or Hodgkin's disease have been reported to correlate with a poor prognosis (Younes & Kadin, 2003, Journal of Clinical Oncology, 21(18):3526-3534; Al-Shamkhani, 2004, Current Opinion in Pharmacology, 4:355-359).

CD30L (CD153) is a type II transmembrane protein that belongs to the TNF family, and is expressed in a wide variety of hematopoietic cells including activated T cells, activated macrophages, B cells, neutrophils, eosiniphils, and mast cells. Engagement of CD30L on these cells with CD30 on the surface of H-RS cells regulates growth and activation, as well as epithelial cells and Hassall's corpuscles in the thymus medulla. A number of hematopoietic tumors also express CD30L, including chronic lymphocytic leukemia (CLL), follicular B-cell lymphoma, hairy cell leukemia, T-cell lymphoblastic lymphoma, and adult T-cell leukemia lymphoma (Younes & Kadin, 2003, Journal of Clinical Oncology, 21(18):3526-3534; Al-Shamkhani, 2004, Current Opinion in Pharmacology, 4:355-359, entirely incorporated by reference).

A common class of therapeutic proteins are monoclonal antibodies. A number of favorable properties of antibodies, including but not limited to specificity for target, ability to mediate immune effector mechanisms, and long half-life in serum, make antibodies powerful therapeutics. A number of antibodies that target CD30 are approved or in clinical trials for the treatment of a variety of cancers. There are also anti-CD30 antibodies in development. Despite the favorable differential expression of CD30 on tumor cells versus normal cells and the number of anti-CD30 antibodies in development, anti-CD30 antibodies have not been successful clinically.

There are a number of possible mechanisms by which antibodies destroy tumor cells, including anti-proliferation via blockage of needed growth pathways, intracellular signaling leading to apoptosis, enhanced down regulation and/or turnover of receptors, CDC, ADCC, ADCP, and promotion of an adaptive immune response (Cragg et al., 1999, *Curr Opin Immunol* 11:541-547; Glennie et al., 2000, *Immunol Today* 21:403-410, both entirely incorporated by reference). Anti-tumor efficacy may be due to a combination of these mechanisms, and their relative importance in clinical therapy appears to be cancer dependent.

A promising means for enhancing the anti-tumor potency of antibodies is via enhancement of their ability to mediate cytotoxic effector functions such as ADCC, ADCP, and CDC. The importance of FcγR-mediated effector functions for the anti-cancer activity of antibodies has been demonstrated in mice (Clynes et al., 1998, *Proc Natl Acad Sci USA* 95:652-656; Clynes et al., 2000, *Nat Med* 6:443-446, both entirely incorporated by reference), and the affinity of interaction between Fc and certain FcγRs correlates with targeted cytotoxicity in cell-based assays (Shields et al., 2001, *J Biol Chem* 276:6591-6604; Presta et al., 2002, *Biochem Soc Trans* 30:487-490; Shields et al., 2002, *J Biol Chem* 277: 26733-26740, each of which is incorporated by reference in its entirety). Additionally, a correlation has been observed between clinical efficacy in humans and their allotype of high (V158) or low (F158) affinity polymorphic forms of FcγRIIIa (Cartron et al., 2002, Blood 99:754-758; Weng & Levy, 2003, Journal of Clinical Oncology, 21:3940-3947, both entirely incorporated by reference). Together these data suggest that an antibody that is optimized for binding to certain FcγRs may better mediate effector functions and thereby destroy cancer cells more effectively in patients. The balance between activating and inhibiting receptors is an important consideration, and optimal effector function may result from an antibody that has enhanced affinity for activation receptors, for example FcγRI, FcγRIIa/c, and FcγRIIIa, yet reduced affinity for the inhibitory receptor FcγRIIb. Furthermore, because FcγRs can mediate antigen uptake and processing by antigen presenting cells, enhanced FcγR affinity may also improve the capacity of antibody therapeutics to elicit an adaptive immune response. With respect to CD30, ADCC has been implicated as an important effector mechanism for the anti-tumor cytotoxic capacity of some anti-CD30 antibodies (Bleeker et al., 2004, J. Immunol. 173(7):4699-707; Bier et al., 1998, Cancer Immunol Immunother 46:167-173, both entirely incorporated by reference).

Some success has been achieved at obtaining Fc variants with selectively enhanced binding to FcγRs, and in some cases these Fc variants have been shown to provide enhanced potency and efficacy in cell-based effector function assays. See, for example, U.S. Pat. No. 5,624,821, PCT WO 00/42072, U.S. Pat. No. 6,737,056, U.S. Ser. No. 10/672,280, PCT US03/30249, and U.S. Ser. No. 10/822,231, and U.S. Ser. No. 60/627,774, filed Nov. 12, 2004 and entitled "Optimized Fc Variants", and references cited therein, each of which is incorporated by reference in its entirety. Enhanced affinity of Fc for FcγR has also been achieved using engineered glycoforms generated by expression of antibodies in engineered or variant cell lines (Umaña et al., 1999, *Nat Biotechnol* 17:176-180; Davies et al., 2001, *Biotechnol Bioeng* 74:288-294; Shields et al., 2002, *J Biol*

Chem 277:26733-26740; Shinkawa et al., 2003, *J Biol Chem* 278:3466-3473, each of which is incorporated by reference in its entirety).

The present invention provides variants of anti-CD30 antibodies that provide enhanced effector function. A variety of modifications are described that provide anti-CD30 antibodies with optimized clinical properties. A broad array of applications of the anti-CD30 antibodies are contemplated.

SUMMARY OF THE INVENTION

In one aspect, the present invention is directed to an anti-CD30 antibody including a variant Fc region. The antibody binds with altered affinity to an FcγR as compared to the parent antibody In certain embodiments, at least one amino acid substitution in the Fc region at a position selected from the group consisting of 221, 222, 224, 227, 228, 230, 231, 223, 233, 234, 235, 236, 237, 238, 239, 240, 241, 243, 244, 245, 246, 247, 249, 250, 258, 262, 263, 264, 265, 266, 267, 268, 269, 270, 271, 272, 273, 274, 275, 276, 278, 280, 281, 283, 285, 286, 288, 290, 291, 293, 294, 295, 296, 297, 298, 299, 300, 302, 313, 317, 318, 320, 322, 323, 324, 325, 326, 327, 328, 329, 330, 331, 332, 333, 334, 335 336 and 428 relative to a parent Fc region, where numbering is according to the EU index as in Kabat. In other aspects, the antibody includes one or more amino acid substitutions in the Fc are selected from among 230, 240, 244, 245, 247, 262, 263, 266, 273, 275, 299, 302, 313, 323, 325, 328, and 332. In further variations, the substitution is selected from the group consisting of H268E, A330Y, A330L and G236A.

In other aspects, the antibody is a humanized antibody. The antibody comprises a variable heavy chain sequence selected from the group consisting of SEQ ID NOS: 2, 4, 7-9 and 11, and/or a variable light chain sequence selected from the group consisting of SEQ ID NOS: 1, 3, 5, 6 and 10. In certain variations, the antibody comprises a heavy chain constant region selected from the group consisting of SEQ ID NOS: 13-19 and/or a light chain constant region SEQ ID NO: 12. In still further variations, the antibody comprises the heavy chain sequence of SEQ ID NO:19 and/or a light chain sequence of SEQ ID NO:20.

The antibody can comprise an engineered glycoform. In certain variations, the anti-CD30 antibody can have reduced fucosylation relative to the parent antibody.

In certain variations, the antibody exhibits altered binding to an FcγR selected from the group consisting of human FcγRI, FcγRIIa, FcγRIIb, FcγRIIc and FcγRIIIa. In certain variations, the antibody binds with greater affinity to the FcγR relative to the parent antibody. In other variations, the antibody binds with reduced affinity to the FcγR relative to the parent antibody.

The antibody can have altered effector function as compared to the parent Fc region. In certain embodiments, the effector function is ADCC. For example, ADCC can be enhanced relative to the parent antibody or inhibited relative to the parent antibody.

In other aspects, the present invention is directed to methods of one or more indications associated with CD30 by administering the anti-CD30 antibody. In certain variations, the indications include cancer, autoimmune disorder, infection disease, and an inflammatory disorder. The anti-CDE30 antibody can be any variation disclosed herein.

The present invention is further directed to pharmaceutical compositions including the anti-CD30 antibody. Formulations including the anti-CD30 antibodies are also included. The pharmaceutical composition can include an anti-CD30 antibody and a pharmaceutically acceptable carrier.

The present invention is also directed to additional compositions comprising the anti-CD30 antibody. In one embodiment, the composition comprises an anti-CD30 antibody, sodium chloride and a surfactant. In certain embodiments, the surfactant is sorbitol. In other embodiments, the surfactant is polysorbate 20 or polysorbate 80. In still other embodiments, the composition can have a pH in the range of 6.0-7.0.

BRIEF DESCRIPTION OF THE DRAWINGS

The following drawings further illustrate aspects of the invention, and do not constrain the scope of the invention.

FIG. 1. Sequences of WT AC10 VL (FIG. 1a) and VH (FIG. 1b)

FIG. 3. Table of CD30 affinities of AC10 Fv variants.

FIG. 5. Sequences of L3 AC10 VL (FIG. 2a) and H3 AC10 VH (FIG. 2b)

FIG. 6. Table of H3 and L3 AC10 variants.

FIG. 8. Sequences of L3.71 AC10 VL, L3.72 AC10 VL, H3.68 AC10 VH, H3.69 AC10 VH, and H3.70 AC10 VH.

FIG. 10. Table of data from FIG. 9.

FIG. 11. H3.69/L3.71 AC10 variants and data.

FIG. 13. Amino acid sequences of variable light (VL) and heavy (VH) chains of the H3.69_V2/L3.71 AC10 antibody.

FIG. 15. Constant chain amino acid sequences.

FIG. 16. Light and heavy chains of the H3.69_V2/L3.71 AC10 IgG(1/2) ELLG antibody comprising mutations S239D/I332E/G327A. EU residues 233-236, 239, 327, and 332 are bolded in the heavy chain sequences.

FIG. 17. Anti-CD30 IgG(1/2) ELLGG Variants. Novel modifications and isotypic modifications are provided for each variant. All IgG variants comprise the variable region of the anti-CD30 antibody H3.69 V2_L3.71 AC10. The variants comprise the IgG(1/2) ELLGG constant region as described in FIG. 18, and potentially one or more additional isotypic modifications and/or one or more novel modifications.

FIG. 19. Data for binding of anti-CD30 IgG variants to human V158 FcγRIIIa as measured by the competition AlphaScreen. For each variant are provided the IC50 (M) and Fold IC50 relative to H3.69_V2_L3.71 AC10 IgG1.

FIG. 22. Cell lines and relative expression of the target antigen CD30.

DETAILED DESCRIPTION OF THE INVENTION

Figure 2A:
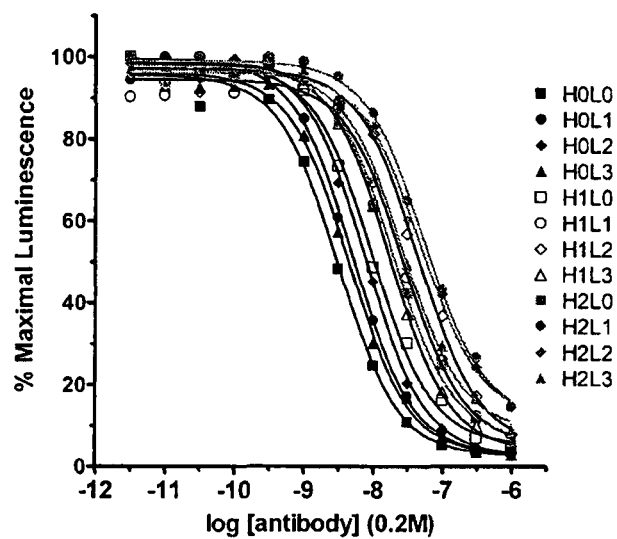
FIG. 2. AlphaScreen™ assay measuring binding between AC10 variants and the target antigen CD30. In the presence of competitor variant antibody, a characteristic inhibition curve is observed as a decrease in luminescence signal. The binding data were normalized to the maximum and minimum luminescence signal for each particular curve, provided by the baselines at low and high antibody concentrations respectively. The curves represent the fits of the data to a one site competition model using nonlinear regression, and the fits provide IC50s for each antibody.

The present invention is directed to anti-CD30 antibodies and methods of using the same. In certain aspects, the anti-CD30 antibodies include a variant Fc region. In further embodiments, the antibodies are humanized. The present invention is further directed to methods of using the anti-CD30 antibodies in various disease indications.

In order that the invention may be more completely understood, several definitions are set forth below. Such definitions are meant to encompass grammatical equivalents.

By "ADCC" or "antibody dependent cell-mediated cytotoxicity" as used herein is meant the cell-mediated reaction wherein nonspecific cytotoxic cells that express FcγRs recognize bound antibody on a target cell and subsequently cause lysis of the target cell.

By "ADCP" or antibody dependent cell-mediated Phagocytosis as used herein is meant the cell-mediated reaction wherein nonspecific cytotoxic cells that express FcγRs recognize bound antibody on a target cell and subsequently cause phagocytosis of the target cell.

By "amino acid modification" herein is meant an amino acid substitution, insertion, and/or deletion in a polypeptide sequence. The preferred amino acid modification herein is a substitution. By "amino acid substitution" or "substitution" herein is meant the replacement of an amino acid at a particular position in a parent polypeptide sequence with another amino acid. For example, the substitution 1332E refers to a variant polypeptide, in this case an Fc variant, in which the isoleucine at position 332 is replaced with a glutamic acid.

By "amino acid" and "amino acid identity" as used herein is meant one of the 20 naturally occurring amino acids or any non-natural analogues that may be present at a specific, defined position. By "protein" herein is meant at least two covalently attached amino acids, which includes proteins, polypeptides, oligopeptides and peptides. The protein may be made up of naturally occurring amino acids and peptide bonds, or synthetic peptidomimetic structures, i.e. "analogs", such as peptoids (see Simon et al., 1992, *Proc Natl Acad Sci USA* 89(20):9367, entirely incorporated by reference,) particularly when LC peptides are to be administered to a patient. Thus "amino acid", or "peptide residue", as used herein means both naturally occurring and synthetic amino acids. For example, homophenylalanine, citrulline and noreleucine are considered amino acids for the purposes of the invention. "Amino acid" also includes imino acid residues such as proline and hydroxyproline. The side chain may be in either the (R) or the (S) configuration. In the preferred embodiment, the amino acids are in the (S) or L-configuration. If non-naturally occurring side chains are used, non-amino acid substituents may be used, for example to prevent or retard in vivo degradation.

By "effector function" as used herein is meant a biochemical event that results from the interaction of an antibody Fc region with an Fc receptor or ligand. Effector functions include but are not limited to ADCC, ADCP, and CDC. By "effector cell" as used herein is meant a cell of the immune system that expresses one or more Fc receptors and mediates one or more effector functions. Effector cells include but are not limited to monocytes, macrophages, neutrophils, dendritic cells, eosinophils, mast cells, platelets, B cells, large granular lymphocytes, Langerhans' cells, natural killer (NK) cells, and γγT cells, and may be from any organism including but not limited to humans, mice, rats, rabbits, and monkeys.

By "library" herein is meant a set of Fc variants in any form, including but not limited to a list of nucleic acid or amino acid sequences, a list of nucleic acid or amino acid substitutions at variable positions, a physical library comprising nucleic acids that encode the library sequences, or a physical library comprising the Fc variant proteins, either in purified or unpurified form.

By "Fc" or "Fc region", as used herein is meant the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cgamma2 and Cgamma3 (Cγ$_2$ and Cγ$_3$) and the hinge between Cgamma1 (Cγ1) and Cgamma2 (Cγ$_2$). Although the boundaries of the Fc region may vary, the human IgG heavy chain Fc region is usually defined to comprise residues C226 or P230 to its carboxylterminus, wherein the numbering is according to the EU index as in Kabat. Fc may refer to this region in isolation, or this region in the context of an Fc polypeptide, as described below. By "Fc polypeptide" as used herein is meant a polypeptide that comprises all or part of an Fc region. Fc polypeptides include antibodies, Fc fusions, isolated Fcs, and Fc fragments.

By "Fc gamma receptor" or "FcγR" as used herein is meant any member of the family of proteins that bind the IgG antibody Fc region and are substantially encoded by the FcγR genes. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRII (CD16), including isoforms FcγRIIIa (including allotypes V158 and F158) and FcγRIIIb (including allotypes FcγRIIIb-NA1 and FcγRIIIb-NA2) (Jefferis et al., 2002, *Immunol Lett* 82:57-65, entirely incorporated by reference), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRII) (CD16), and FcγRII)-2 (CD16-2), as well as any undiscovered mouse FcγRs or FcγR isoforms or allotypes.

By "Fc ligand" as used herein is meant a molecule, preferably a polypeptide, from any organism that binds to the Fc region of an antibody to form an Fc-ligand complex. Fc ligands include but are not limited to FcγRs, FcγRs, FcγRs, FcRn, C1q, C3, mannan binding lectin, mannose receptor, *staphylococcal* protein A, *streptococcal* protein G, and viral FcγR. Fc ligands also include Fc receptor homologs (FcRH), which are a family of Fc receptors that are homologous to the FcγRs (Davis et al., 2002, *Immunological Reviews* 190:123-136). Fc ligands may include undiscovered molecules that bind Fc.

By "IgG" as used herein is meant a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, IgG3. By "immunoglobulin (Ig)" herein is meant a protein consisting of one or more polypeptides substantially encoded by immunoglobulin genes. Immunoglobulins include but are not limited to antibodies. Immunoglobulins may have a number of structural forms, including but not limited to full length antibodies, antibody fragments, and individual immunoglobulin domains. By "immunoglobulin (IQ) domain" herein is meant a region of an immunoglobulin that exists as a distinct structural entity as ascertained by one skilled in the art of protein structure. Ig domains typically have a characteristic β-sandwich folding topology. The known Ig domains in the IgG class of antibodies are $V_H$, $C\gamma 1$, $C\gamma_2$, $C\gamma_3$, $V_L$, and $C_L$.

By "parent polypeptide" or "precursor polypeptide" (including Fc parent or precursors) as used herein is meant a polypeptide that is subsequently modified to generate a variant. Said parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent Fc polypeptide" as used herein is meant a Fc polypeptide that is modified to generate a variant, and by "parent antibody" as used herein is meant an antibody that is modified to generate a variant antibody.

As outlined above, certain positions of the Fc molecule can be altered. By "position" as used herein is meant a location in the sequence of a protein. Positions may be numbered sequentially, or according to an established format, for example the EU index as in Kabat. For example, position 297 is a position in the human antibody IgG1. Corresponding positions are determined as outlined above, generally through alignment with other parent sequences.

By "residue" as used herein is meant a position in a protein and its associated amino acid identity. For example, Asparagine 297 (also referred to as Asn297, also referred to as N297) is a residue in the human antibody IgG1.

By "target antigen" as used herein is meant the molecule that is bound specifically by the variable region of a given antibody. A target antigen may be a protein, carbohydrate, lipid, or other chemical compound.

By "target cell" as used herein is meant a cell that expresses a target antigen.

By "variable region" as used herein is meant the region of an immunoglobulin that comprises one or more Ig domains substantially encoded by any of the VK, VA, and/or $V_H$ genes that make up the kappa, lambda, and heavy chain immunoglobulin genetic loci respectively.

By "variant protein", "protein variant", "variant polypeptide", or "polypeptide variant" as used herein is meant a polypeptide sequence that differs from that of a parent polypeptide sequence by virtue of at least one amino acid modification. Variant polypeptide may refer to the polypeptide itself, a composition comprising the polypeptide, or the amino sequence that encodes it. Preferably, the variant polypeptide has at least one amino acid modification compared to the parent polypeptide, e.g. from about one to about ten amino acid modifications, and preferably from about one to about five amino acid modifications compared to the parent. The variant polypeptide sequence herein will preferably possess at least about 80% homology with a parent polypeptide sequence, and most preferably at least about 90% homology, more preferably at least about 95% homology. Accordingly, by "variant Fc" or "Fc variant" as used herein is meant an Fc sequence that differs from that of a parent Fc sequence by virtue of at least one amino acid modification. An Fc variant may only encompass an Fc region, or may exist in the context of an antibody, Fc fusion, or other polypeptide that is substantially encoded by Fc. Fc variant may refer to the Fc polypeptide itself, compositions comprising the Fc variant polypeptide, or the amino acid sequence that encodes it. Accordingly, by "variant anti-CD30 antibody" or "anti-CD30 antibody variant" as used herein is meant an anti-CD30 antibody, as defined above, that differs in sequence from that of a parent anti-CD30 antibody sequence by virtue of at least one amino acid modification. Variant anti-CD30 antibody may refer to the protein itself, compositions comprising the protein, or the amino acid sequence that encodes it.

For all immunoglobulin heavy chain constant region positions discussed in the present invention, numbering is according to the EU index as in Kabat (Kabat et al., 1991, Sequences of Proteins of Immunological Interest, 5th Ed., United States Public Health Service, National Institutes of Health, Bethesda). The "EU index as in Kabat" refers to the residue numbering of the human IgG1 EU antibody.

Anti-CD30 Antibodies

An anti-CD30 antibody is an antibody that binds to CD30. Anti-CD30 antibodies may bind any epitope or region on CD30, and may be specific for fragments, splice forms, or aberrant forms of CD30. The present application is directed to anti-CD-30 antibodies. Various anti-CD30 antibodies are disclosed U.S. patent application Ser. No. 11/004,590, filed Dec. 3, 2004, titled "Methods of Generating Variant Proteins with Increased Host String Content and Compositions Thereof"; and in provisional U.S. applications 60/724,624, filed Oct. 6, 2005, titled "Anti-CD30 Antibodies"; 60/737,998, filed Nov. 18, 2005, titled "Anti-CD30 Antibodies"; 60/750,697, filed Dec. 15, 2005, titled "Anti-CD30 Antibodies"; 60/776,598, filed Feb. 24, 2006, titled "Anti-CD30 Antibodies"; each of which is incorporated by reference in its entirety. The anti-CD30 antibodies may be, for example, traditional antibodies, antibody fragments, bispecific antibodies, or other immunoglobulin formats or antibody fusions. The antibodies may also be chimeric antibodies, humanized antibodies, or fully human antibodies. Antibodies also include labeled or covalently modified antibodies, as described herein.

Antibodies

Antibodies are immunological proteins that bind a specific antigen. In most mammals, including humans and mice, antibodies are constructed from paired heavy and light polypeptide chains. The light and heavy chain variable regions show significant sequence diversity between antibodies, and are responsible for binding the target antigen. Each chain is made up of individual immunoglobulin (Ig) domains, and thus the generic term immunoglobulin is used for such proteins.

In certain embodiments, antibodies can be monoclonal or polyclonal. Antibodies can be antagonists, agonists, neutralizing, inhibitory, or stimulatory.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. IgA has several subclasses, including but not limited to IgA1 and IgA2. Thus, "isotype" as used herein is meant any of the subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE.

Each of the light and heavy chains are made up of two distinct regions, referred to as the variable and constant regions. The IgG heavy chain is composed of four immunoglobulin domains linked from N- to C-terminus in the order $V_H$-CH1-CH2-CH3, referring to the heavy chain variable domain, heavy chain constant domain 1, heavy chain constant domain 2, and heavy chain constant domain 3 respectively (also referred to as $V_H$-Cγ1-Cγ2-Cγ3, referring to the heavy chain variable domain, constant gamma 1 domain, constant gamma 2 domain, and constant gamma 3 domain respectively). The IgG light chain is composed of two immunoglobulin domains linked from N- to C-terminus in the order $V_L$-$C_L$, referring to the light chain variable domain and the light chain constant domain respectively. The constant regions show less sequence diversity, and are responsible for binding a number of natural proteins to elicit important biochemical events. The distinguishing features between these antibody classes are their constant regions, although subtler differences may exist in the V region.

The variable region of an antibody contains the antigen binding determinants of the molecule, and thus determines the specificity of an antibody for its target antigen. The variable region is so named because it is the most distinct in sequence from other antibodies within the same class. The amino-terminal portion of each chain includes a variable region of about 100 to 110 or more amino acids primarily responsible for antigen recognition. In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. There are 6 CDRs total, three each per heavy and light chain, designated $V_H$ CDR1, $V_H$ CDR2, $V_H$ CDR3, $V_L$ CDR1, $V_L$ CDR2, and $V_L$ CDR3. The variable region outside of the CDRs is referred to as the framework (FR) region. Although not as diverse as the CDRs, sequence variability does occur in the FR region between different antibodies. Overall, this characteristic architecture of antibodies provides a stable scaffold (the FR region) upon which substantial antigen binding diversity (the CDRs) can be explored by the immune system to obtain specificity for a broad array of antigens. A number of high-resolution structures are available for a variety of variable region fragments from different organisms, some unbound and some in complex with antigen. Sequence and structural features of antibody variable regions are disclosed, for example, in Morea et al., 1997, *Biophys Chem* 68:9-16; Morea et al., 2000, *Methods* 20:267-279, hereby entirely incorporated by reference, and the conserved features of antibodies are disclosed, for example, in Maynard et al., 2000, *Annu Rev Biomed Eng* 2:339-376, hereby entirely incorporated by reference.

The carboxy-terminal portion of each chain defines a constant region primarily responsible for effector function. Kabat et al. collected numerous primary sequences of the variable regions of heavy chains and light chains. Based on the degree of conservation of the sequences, they classified individual primary sequences into the CDR and the framework and made a list thereof (see SEQUENCES OF IMMUNOLOGICAL INTEREST, 5th edition, NIH publication, No. 91-3242, E. A. Kabat et al.).

In the IgG subclass of immunoglobulins, there are several immunoglobulin domains in the heavy chain. By "immunoglobulin (Ig) domain" herein is meant a region of an immunoglobulin having a distinct tertiary structure. Of interest in the present invention are the heavy chain domains, including, the constant heavy (CH) domains and the hinge domains. In the context of IgG antibodies, the IgG isotypes each have three CH regions. Accordingly, "CH" domains in the context of IgG are as follows: "CH1" refers to positions 118-220 according to the EU index as in Kabat. "CH2" refers to positions 237-340 according to the EU index as in Kabat, and "CH3" refers to positions 341-447 according to the EU index as in Kabat.

Another type of Ig domain of the heavy chain is the hinge region. By "hinge" or "hinge region" or "antibody hinge region" or "immunoglobulin hinge region" herein is meant the flexible polypeptide comprising the amino acids between the first and second constant domains of an antibody. Structurally, the IgG CH1 domain ends at EU position 220, and the IgG CH2 domain begins at residue EU position 237. Thus for IgG the antibody hinge is herein defined to include positions 221 (D221 in IgG1) to 236 (G236 in IgG1), wherein the numbering is according to the EU index as in Kabat. In some embodiments, for example in the context of an Fc region, the lower hinge is included, with the "lower hinge" generally referring to positions 226 or 230. Specifically included within the definition of "antibody" are full-length antibodies that contain an Fc variant portion. By "full length antibody" herein is meant the structure that constitutes the natural biological form of an antibody, including variable and constant regions. For example, in most mammals, including humans and mice, the full length antibody of the IgG class is a tetramer and consists of two identical pairs of two immunoglobulin chains, each pair having one light and one heavy chain, each light chain comprising immunoglobulin domains $V_L$ and $C_L$, and each heavy chain comprising immunoglobulin domains $V_H$, Cγ1, Cγ2, and Cγ3. In some mammals, for example in camels and llamas, IgG antibodies may consist of only two heavy chains, each heavy chain comprising a variable domain attached to the Fc region. By "IgG" as used herein is meant a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, IgG3.

As is well known in the art, immunoglobulin polymorphisms exist in the human population. Gm polymorphism is determined by the IGHG1, IGHG2 and IGHG3 genes which have alleles encoding allotypic antigenic determinants referred to as G1m, G2m, and G3m allotypes for markers of the human IgG1, IgG2 and IgG3 molecules (no Gm allotypes have been found on the gamma 4 chain). Markers may be classified into 'allotypes' and 'isoallotypes'. These are distinguished on different serological bases dependent upon the strong sequence homologies between isotypes. Allotypes are antigenic determinants specified by allelic forms of the Ig genes. Allotypes represent slight differences in the amino acid sequences of heavy or light chains of different individuals. Even a single amino acid difference can give rise to an allotypic determinant, although in many cases there are several amino acid substitutions that have occurred. Allotypes are sequence differences between alleles of a subclass whereby the antisera recognize only the allelic differences. An isoallotype is an allele in one isotype which produces an epitope which is shared with a non-polymorphic homologous region of one or more other isotypes and because of this the antisera will react with both the relevant allotypes and the relevant homologous isotypes (Clark, 1997, IgG effector mechanisms, Chem. Immunol. 65:88-110; Gorman & Clark, 1990, Semin Immunol 2(6):457-66, both hereby which is incorporated by reference in its entirety).

Allelic forms of human immunoglobulins have been well-characterized (WHO Review of the notation for the allotypic and related markers of human immunoglobulins. J Immunogen 1976, 3: 357-362; WHO Review of the notation for the allotypic and related markers of human immunoglobulins. 1976, Eur. J. Immunol. 6, 599-601; Loghem E van, 1986, Allotypic markers, Monogr Allergy 19: 40-51, all hereby entirely incorporated by reference). Additionally, other polymorphisms have been characterized (Kim et al., 2001, J. Mol. Evol. 54:1-9, hereby which are incorporated by reference in their entirety). At present, 18 Gm allotypes are known: G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b5, b0, b3, b4, s, t, g1, c5, u, v, g5) (Lefranc, et al., The human IgG subclasses: molecular analysis of structure, function and regulation. Pergamon, Oxford, pp. 43-78 (1990); Lefranc, G. et al., 1979, Hum. Genet.: 50, 199-211, both hereby entirely incorporated by reference). Allotypes that are inherited in fixed combinations are called Gm haplotypes. FIG. 3 shows common haplotypes of the gamma chain of human IgG1 (FIG. 3a) and IgG2 (FIG. 3b) showing the positions and the relevant amino acid substitutions. The Fc variants of the present invention may be substantially encoded by any allotype, isoallotype, or haplotype of any immunoglobulin gene.

Alternatively, the antibodies can be a variety of structures, including, but not limited to, antibody fragments, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each, respectively.

Antibody fragments, bispecific antibodies, and other immunoglobulin formats

In one embodiment, the antibody is an antibody fragment. Of particular interest are antibodies that comprise Fc regions, Fc fusions, and the constant region of the heavy chain (CH1-hinge-CH2-CH3), again also including constant heavy region fusions.

Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546) which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883), (viii) bispecific single chain Fv dimers (PCT/US92/09965) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448). The antibody fragments may be modified. For example, the molecules may be stabilized by the incorporation of disulphide bridges linking the VH and VL domains (Reiter et al., 1996, Nature Biotech. 14:1239-1245).

In one embodiment, the antibodies of the invention multispecific antibody, and notably a bispecific antibody, also sometimes referred to as "diabodies". These are antibodies that bind to two (or more) different antigens. Diabodies can be manufactured in a variety of ways known in the art (Holliger and Winter, 1993, Current Opinion Biotechnol. 4:446-449), e.g., prepared chemically or from hybrid hybridomas. In one embodiment, the antibody is a minibody. Minibodies are minimized antibody-like proteins comprising a scFv joined to a CH3 domain. Hu et al., 1996, Cancer Res. 56:3055-3061. In some cases, the scFv can be joined to the Fc region, and may include some or all of the hinge region.

Chimeric, Humanized, and Fully Human Antibodies

In some embodiments, the scaffold components can be a mixture from different species. As such, if the antibody is an antibody, such antibody may be a chimeric antibody and/or a humanized antibody. In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human. "Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321: 522-525, Verhoeyen et al., 1988, Science 239:1534-1536. "Backmutation" of selected acceptor framework residues to the corresponding donor residues is often required to regain affinity that is lost in the initial grafted construct (U.S. Pat. Nos. 5,530,101; 5,585,089; 5,693,761; 5,693,762; 6,180,370; 5,859,205; 5,821,337; 6,054,297; 6,407,213). The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system. Roque et al., 2004, Biotechnol. Prog. 20:639-654. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein). Humanization methods include but are not limited to methods described in Jones et al., 1986, *Nature* 321:522-525; Riechmann et al., 1988; *Nature* 332:323-329; Verhoeyen et al., 1988, *Science*, 239:1534-1536; Queen et al., 1989, *Proc Natl Acad Sci, USA* 86:10029-33; He et al., 1998, J. Immunol. 160: 1029-1035; Carter et al., 1992, *Proc Natl Acad Sci USA* 89:4285-9, Presta et al., 1997, Cancer Res.57(20): 4593-9; Gorman et al., 1991, Proc. Natl. Acad. Sci. USA 88:4181-4185; O'Connor et al., 1998, *Protein Eng* 11:321-8. Humanization or other methods of reducing the immunogenicity of nonhuman antibody variable regions may include resurfacing methods, as described for example in Roguska et al., 1994, Proc. Natl. Acad. Sci. USA 91:969-973. In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16): 10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759. Other humanization methods may involve the grafting of only parts of the CDRs, including but not limited to methods described in U.S. Ser. No. 09/810,502; Tan et al., 2002, J. Immunol. 169:1119-1125; De Pascalis et al., 2002, J. Immunol. 169:3076-3084.

In one embodiment, the antibody is a fully human antibody with at least one modification as outlined herein. "Fully human antibody" or "complete human antibody" refers to a human antibody having the gene sequence of an antibody derived from a human chromosome with the modifications outlined herein. Fully human antibodies may be obtained, for example, using transgenic mice (Bruggemann et al., 1997, *Curr Opin Biotechnol* 8:455-458) or human antibody libraries coupled with selection methods (Griffiths et al., 1998, *Curr Opin Biotechnol* 9:102-108).

Antibody Fusions

In one embodiment, the antibodies of the invention are antibody fusion proteins (sometimes referred to herein as an "antibody conjugate"). One type of antibody fusions are Fc fusions, which join the Fc region with a conjugate partner. By "Fc fusion" as used herein is meant a protein wherein one or more polypeptides is operably linked to an Fc region. Fc fusion is herein meant to be synonymous with the terms "immunoadhesin", "Ig fusion", "Ig chimera", and "receptor globulin" (sometimes with dashes) as used in the prior art (Chamow et al., 1996, Trends Biotechnol 14:52-60; Ashkenazi et al., 1997, Curr Opin Immunol 9:195-200). An Fc fusion combines the Fc region of an immunoglobulin with a fusion partner, which in general can be any protein or small molecule. Virtually any protein or small molecule may be linked to Fc to generate an Fc fusion. Protein fusion partners may include, but are not limited to, the variable region of any antibody, the target-binding region of a receptor, an adhesion molecule, a ligand, an enzyme, a cytokine, a chemokine, or some other protein or protein domain. Small molecule fusion partners may include any therapeutic agent that directs the Fc fusion to a therapeutic target. Such targets may be any molecule, preferably an extracellular receptor, that is implicated in disease.

In addition to antibodies, an antibody-like protein that is finding an expanding role in research and therapy is the Fc fusion (Chamow et al., 1996, *Trends Biotechnol* 14:52-60; Ashkenazi et al., 1997, *Curr Opin Immunol* 9:195-200, both hereby entirely incorporated by reference). An Fc fusion is a protein wherein one or more polypeptides is operably linked to Fc. An Fc fusion combines the Fc region of an antibody, and thus its favorable effector functions and pharmacokinetics, with the target-binding region of a receptor, ligand, or some other protein or protein domain. The role of the latter is to mediate target recognition, and thus it is functionally analogous to the antibody variable region. Because of the structural and functional overlap of Fc fusions with antibodies, the discussion on antibodies in the present invention extends also to Fc fusions.

In addition to Fc fusions, antibody fusions include the fusion of the constant region of the heavy chain with one or more fusion partners (again including the variable region of any antibody), while other antibody fusions are substantially or completely full length antibodies with fusion partners. In one embodiment, a role of the fusion partner is to mediate target binding, and thus it is functionally analogous to the variable regions of an antibody (and in fact can be). Virtually any protein or small molecule may be linked to Fc to generate an Fc fusion (or antibody fusion). Protein fusion partners may include, but are not limited to, the target-binding region of a receptor, an adhesion molecule, a ligand, an enzyme, a cytokine, a chemokine, or some other protein or protein domain. Small molecule fusion partners may include any therapeutic agent that directs the Fc fusion to a therapeutic target. Such targets may be any molecule, preferably an extracellular receptor, that is implicated in disease.

The conjugate partner can be proteinaceous or non-proteinaceous; the latter generally being generated using functional groups on the antibody and on the conjugate partner. For example linkers are known in the art; for example, homo-or hetero-bifunctional linkers as are well known (see, 1994 Pierce Chemical Company catalog, technical section on cross-linkers, pages 155-200, incorporated herein by reference).

Suitable conjugates include, but are not limited to, labels as described below, drugs and cytotoxic agents including, but not limited to, cytotoxic drugs (e.g., chemotherapeutic agents) or toxins or active fragments of such toxins. Suitable toxins and their corresponding fragments include diptheria A chain, exotoxin A chain, ricin A chain, abrin A chain, curcin, crotin, phenomycin, enomycin and the like. Cytotoxic agents also include radiochemicals made by conjugating radioisotopes to antibodies, or binding of a radionuclide to a chelating agent that has been covalently attached to the antibody. Additional embodiments utilize calicheamicin, auristatins, geldanamycin, maytansine, and duocarmycins and analogs; for the latter, see U.S. 2003/0050331, hereby incorporated by reference in its entirety.

Covalent Modifications of Antibodies

Covalent modifications of antibodies are included within the scope of this invention, and are generally, but not always, done post-translationally. For example, several types of covalent modifications of the antibody are introduced into the molecule by reacting specific amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using 125I or 131I to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking antibodies to a water-insoluble support matrix or surface for use in a variety of methods, in addition to methods described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco, pp. 79-86 [1983]), acetylation of the N-terminal amine, and amidation of any C-terminal carboxyl group.

Another type of covalent modification of the antibody comprises linking the antibody to various nonproteinaceous polymers, including, but not limited to, various polyols such as polyethylene glycol, polypropylene glycol or polyoxyalkylenes, in the manner set forth in U.S. Pat. No. 4,640,835; 4,496,689; 4,301,144; 4,670,417; 4,791,192 or 4,179,337. In addition, as is known in the art, amino acid substitutions may be made in various positions within the antibody to facilitate the addition of polymers such as PEG. See for example, U.S. Publication No. 2005/0114037, incorporated herein by reference in its entirety.

Labeled Antibodies

In some embodiments, the covalent modification of the antibodies of the invention comprises the addition of one or more labels. In some cases, these are considered antibody fusions.

The term "labeling group" means any detectable label. In some embodiments, the labeling group is coupled to the antibody via spacer arms of various lengths to reduce potential steric hindrance. Various methods for labeling proteins are known in the art and may be used in performing the present invention.

In general, labels fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labeling group is coupled to the antibody via spacer arms of various lengths to reduce potential steric hindrance. Various methods for labeling proteins are known in the art and may be used in performing the present invention.

Specific labels include optical dyes, including, but not limited to, chromophores, phosphors and fluorophores, with the latter being specific in many instances. Fluorophores can be either "small molecule" fluores, or proteinaceous fluores.

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, Oreg.), FITC, Rhodamine, and Texas Red (Pierce, Rockford, Ill.), Cy5, Cy5.5, Cy7 (Amersham Life Science, Pittsburgh, Pa.). Suitable optical dyes, including fluorophores, are described in Molecular Probes Handbook by Richard P. Haugland, hereby expressly incorporated by reference. \

Suitable proteinaceous fluorescent labels also include, but are not limited to, green fluorescent protein, including a Renilla, Ptilosarcus, or Aequorea species of GFP (Chalfie et al., 1994, Science 263:802-805), EGFP (Clontech Laboratories, Inc., Genbank Accession Number U55762), blue fluorescent protein (BFP, Quantum Biotechnologies, Inc. 1801 de Maisonneuve Blvd. West, 8th Floor, Montreal, Quebec, Canada H3H 1J9; Stauber, 1998, Biotechniques 24:462-471; Heim et al., 1996, Curr. Biol. 6:178-182), enhanced yellow fluorescent protein (EYFP, Clontech Laboratories, Inc.), luciferase (Ichiki et al., 1993, J. Immunol. 150:5408-5417), β galactosidase (Nolan et al., 1988, Proc. Natl. Acad. Sci. U.S.A. 85:2603-2607) and Renilla (WO92/15673, WO95/07463, WO98/14605, WO98/26277, WO99/49019, U.S. Pat. Nos. 5,292,658, 5,418,155, 5,683,888, 5,741,668, 5,777,079, 5,804,387, 5,874,304, 5,876,995, 5,925,558). All of the above-cited references are expressly incorporated herein by reference.

The variable regions of any known or undiscovered anti-CD30 antibody may find use in the present invention. A number of useful antibodies have been discovered that target CD30.

Anti-CD30 antibodies of the present invention may comprise Fc fragments. An Fc fragment of the present invention may comprise from 1-90% of the Fc region, with 10-90% being preferred, and 30-90% being most preferred. Thus for example, an Fc fragment of the present invention may comprise an IgG1 Cγ2 domain, an IgG1 Cγ2 domain and hinge region, an IgG1 Cγ3 domain, and so forth. In one embodiment, an Fc fragment of the present invention additionally comprises a fusion partner, effectively making it an Fc fragment fusion. Fc fragments may or may not contain extra polypeptide sequence.

Anti-CD30 antibodies of the present invention may be substantially encoded by genes from any organism, preferably mammals, including but not limited to humans, rodents including but not limited to mice and rats, lagomorpha including but not limited to rabbits and hares, camelidae including but not limited to camels, llamas, and dromedaries, and non-human primates, including but not limited to Prosimians, Platyrrhini (New World monkeys), Cercopithecoidea (Old World monkeys), and Hominoidea including the Gibbons and Lesser and Great Apes. In a most preferred embodiment, the anti-CD30 antibodies of the present invention are substantially human. The anti-CD30 antibodies of the present invention may be substantially encoded by immunoglobulin genes belonging to any of the antibody classes. In a most preferred embodiment, the anti-CD30 antibodies of the present invention comprise sequences belonging to the IgG class of antibodies, including human subclasses IgG1, IgG2, IgG3, and IgG4. In an alternate embodiment, the anti-CD30 antibodies of the present invention comprise sequences belonging to the IgA (including human subclasses IgA1 and IgA2), IgD, IgE, IgG, or IgM classes of antibodies. The anti-CD30 antibodies of the present invention may comprise more than one protein chain. That is, the present invention may find use in an anti-CD30 antibody that is a monomer or an oligomer, including a homo- or hetero-oligomer.

As reverenced in U.S. patent application Ser. No. 11/544,165, filed Oct. 3, 2006 and incorporated herein by reference in its entirety, certain combinations of amino acid modifications at positions 235, 236, 237, 238, 239, 265, 266, 267, 268, 269, 270, 295, 296, 298, 299, 325, 326, 327, 328, 329, 330, and 332 allow modification of FcγR binding properties, the effector function, and potentially the clinical properties of Fc polypeptides, including antibodies and Fc fusions. In particular, Fc variants that selectively improve binding to one or more human activating receptors relative to FcγRIIb, or selectively improve binding to FcγRIIb relative to one or more activating receptors, may comprise a substitution, as described herein, selected from the group consisting of 234G, 234I, 235D, 235E, 235I, 235Y, 236A, 236S, 239D, 267D, 267E, 267Q, 268D, 268E, 293R, 295E, 324G, 324I, 327H, 328A, 328F, 328I, 330I, 330L, 330Y, 332D, and 332E.

Additional exemplary substitutions that may also be combined include other substitutions that modulate FcγR affinity and complement activity, including but not limited to 298A, 298T, 326A, 326D, 326E, 326W, 326Y, 333A, 333S, 334L, and 334A (U.S. Pat. No. 6,737,056; Shields et al, Journal of Biological Chemistry, 2001, 276(9):6591-6604; U.S. Pat. No. 6,528,624; Idusogie et al., 2001, J. Immunology 166: 2571-2572). Preferred variants that may be particularly useful to combine with variants of the present invention include those that comprise the substitutions 298A, 326A, 333A, and 334A. AlphaScreen data measuring the binding of Fc variants comprising these substitutions to the human activating receptors V158 and F158 FcγRIIIa and the inhibitory receptor FcγRIIb. Additional substitutions that may be combined with the FcγR selective variants of the present invention 247L, 255L, 270E, 392T, 396L, and 421 K (U.S. Ser. Nos. 10/754,922; 10/902,588), and 280H, 280Q, and 280Y (U.S. Ser. No. 10/370,749), all of which are expressly incorporated herein by reference In other embodiments, Fc variants of the present invention may be combined with Fc variants that alter FcRn binding. In particular, variants that increase Fc binding to FcRn include but are not limited to: 250E, 250Q, 428L, 428F, 250Q/428L (Hinton et al., 2004, J. Biol. Chem. 279(8): 6213-6216, Hinton et al. 2006 Journal of Immunology 176:346-356, U.S. Ser. No. 11/102,621, PCT/US2003/033037, PCT/US2004/011213, U.S. Ser. Nos. 10/822,300, 10/687,118, PCT/US2004/034440, U.S. Ser. No. 10/966,673 each of which is incorporated by reference in its entirety), 256A, 272A, 286A, 305A, 307A, 311A, 312A, 376A, 378Q, 380A, 382A, 434A (Shields et al, Journal of Biological Chemistry, 2001, 276(9):6591-6604, U.S. Ser. No. 10/982,470, U.S. Pat. No. 6,737,056, U.S. Ser. Nos. 11/429,793, 11/429,786, PCT/US2005/029511, U.S. Ser. No. 11/208,422, each of which is incorporated by reference in its entirety), 252F, 252T, 252Y, 252W, 254T, 256S, 256R, 256Q, 256E, 256D, 256T, 309P, 311S, 433R, 433S, 433I, 433P, 433Q, 434H, 434F, 434Y, 252Y/254T/256E, 433K/434F/436H, 308T/309P/311S (DaII Acqua et al. Journal of Immunology, 2002, 169:5171-5180, U.S. Pat. No. 7,083,784, PCT/US97/03321, U.S. Pat. No. 6,821,505, PCT/US01/48432, U.S. Ser. No. 11/397,328, each of which is incorporated by reference in its entirety), 257C, 257M, 257L, 257N, 257Y, 279E, 279Q, 279Y, insertion of Ser after 281, 283F, 284E, 306Y, 307V, 308F, 308Y 311V, 385H, 385N, (PCT/US2005/041220, U.S. Ser. Nos. 11/274,065, 11/436,266 each of which is incorporated by reference in its entirety) 204D, 284E, 285E, 286D, and 290E (PCT/US2004/037929 which is incorporated by reference in its entirety).

A key feature of the Fc region is the conserved N-linked glycosylation that occurs at N297. This carbohydrate, or oligosaccharide as it is sometimes referred, plays a critical structural and functional role for the antibody, and is one of the principle reasons that antibodies must be produced using mammalian expression systems. Efficient Fc binding to FcγR and C1q requires this modification, and alterations in the composition of the N297 carbohydrate or its elimination affect binding to these proteins (Umaña et al., 1999, *Nat Biotechnol* 17:176-180; Davies et al., 2001, *Biotechnol Bioeng* 74:288-294; Mimura et al., 2001, *J Biol Chem* 276:45539-45547.; Radaev et al., 2001, *J Biol Chem* 276: 16478-16483; Shields et al., 2001, *J Biol Chem* 276:6591-6604; Shields et al., 2002, *J Biol Chem* 277:26733-26740; Simmons et al., 2002, *J Immunol Methods* 263:133-147, each of which is incorporated by reference in its entirety).

Fc variants of the present invention may be substantially encoded by genes from any organism, preferably mammals, including but not limited to humans, rodents including but not limited to mice and rats, lagomorpha including but not limited to rabbits and hares, camelidae including but not limited to camels, llamas, and dromedaries, and non-human primates, including but not limited to Prosimians, Platyrrhini (New World monkeys), Cercopithecoidea (Old World monkeys), and Hominoidea including the Gibbons and Lesser and Great Apes. In a certain embodiments, the Fc variants of the present invention are substantially human.

In the most preferred embodiment, the anti-CD30 antibodies of the invention are based on human IgG sequences, and thus human IgG sequences are used as the "base" sequences against which other sequences are compared, including but not limited to sequences from other organisms, for example rodent and primate sequences, as well as sequences from other immunoglobulin classes such as IgA, IgE, IgGD, IgGM, and the like. It is contemplated that, although the anti-CD30 antibodies of the present invention are engineered in the context of one parent anti-CD30 antibody, the variants may be engineered in or "transferred" to the context of another, second parent anti-CD30 antibody. This is done by determining the "equivalent" or "corresponding" residues and substitutions between the first and second anti-CD30 antibodies, typically based on sequence or structural homology between the sequences of the two anti-CD30 antibodies. In order to establish homology, the amino acid sequence of a first anti-CD30 antibody outlined herein is directly compared to the sequence of a second anti-CD30 antibody. After aligning the sequences, using one or more of the homology alignment programs known in the art (for example using conserved residues as between species), allowing for necessary insertions and deletions in order to maintain alignment (i.e., avoiding the elimination of conserved residues through arbitrary deletion and insertion), the residues equivalent to particular amino acids in the primary sequence of the first anti-CD30 antibody are defined. Alignment of conserved residues preferably should conserve 100% of such residues. However, alignment of greater than 75% or as little as 50% of conserved residues is also adequate to define equivalent residues. Equivalent residues may also be defined by determining structural homology between a first and second anti-CD30 antibody that is at the level of tertiary structure for anti-CD30 antibodies whose structures have been determined. In this case, equivalent residues are defined as those for which the atomic coordinates of two or more of the main chain atoms of a particular amino acid residue of the parent or precursor (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the proteins. Regardless of how equivalent or corresponding residues are determined, and regardless of the identity of the parent anti-CD30 antibody in which the anti-CD30 antibodies are made, what is meant to be conveyed is that the anti-CD30 antibodies discovered by the present invention may be engineered into any second parent anti-CD30 antibody that has significant sequence or structural homology with said anti-CD30 antibody. Thus for example, if a variant anti-CD30 antibody is generated wherein the parent anti-CD30 antibody is human IgG1, by using the methods described above or other methods for determining equivalent residues, said variant anti-CD30 antibody may be engineered in a human IgG2 parent anti-CD30 antibody, a human IgA parent anti-CD30 antibody, a mouse IgG2a or IgG2b parent anti-CD30 antibody, and the like. Again, as described above, the context of the parent anti-CD30 antibody does not affect the ability to transfer the anti-CD30 antibodies of the present invention to other parent anti-CD30 antibodies. For example, the variant anti-CD30 antibodies that are engineered in a human IgG1 antibody that targets one CD30 epitope may be transferred into a human IgG2 antibody that targets a different CD30 epitope, and so forth.

The anti-CD30 antibody of the present invention may be virtually any antibody that binds CD30. Anti-CD30 antibodies of the invention may display selectivity for CD30 versus alternative targets, for example other RTKs, or selectivity for a specific form of the CD30 target versus alternative forms. Examples include full-length versus splice variants, cell-surface vs. soluble forms, selectivity for various polymorphic variants, or selectivity for specific conformational forms of a target. An anti-CD30 antibody of the present invention may bind any epitope or region on CD30, and may be specific for fragments, mutant forms, splice forms, or aberrant forms of CD30.

The anti-CD30 antibodies of the present invention may find use in a wide range of products. In one embodiment the anti-CD30 antibody of the invention is a therapeutic, a diagnostic, or a research reagent, preferably a therapeutic. Alternatively, the anti-CD30 antibody of the present invention may be used for agricultural or industrial uses. An anti-CD30 antibody of the present invention may find use in an antibody composition that is monoclonal or polyclonal. The anti-CD30 antibodies of the present invention may be agonists, antagonists, neutralizing, inhibitory, or stimulatory. In a preferred embodiment, the anti-CD30 antibodies of the present invention are used to kill target cells that bear the CD30 target antigen, for example cancer cells. In an alternate embodiment, the anti-CD30 antibodies of the present invention are used to block, antagonize, or agonize the CD30 target antigen. In an alternately preferred embodiment, the anti-CD30 antibodies of the present invention are used to block, antagonize, or agonize the target antigen and kill the target cells that bear the target antigen.

Modifications

The present invention provides variant anti-CD30 antibodies that are optimized for a number of therapeutically relevant properties. A variant anti-CD30 antibody comprises one or more amino acid modifications relative to a parent anti-CD30 antibody, wherein said amino acid modification(s) provide one or more optimized properties. Thus the anti-CD30 antibodies of the present invention are variants anti-CD30 antibodies. An anti-CD30 antibody of the present invention differs in amino acid sequence from its parent anti-CD30 antibody by virtue of at least one amino acid modification. Thus variant anti-CD30 antibodies of the present invention have at least one amino acid modification compared to the parent. Alternatively, the variant anti-CD30 antibodies of the present invention may have more than one amino acid modification as compared to the parent, for example from about one to fifty amino acid modifications, preferably from about one to ten amino acid modifications, and most preferably from about one to about five amino acid modifications compared to the parent. Thus the sequences of the variant anti-CD30 antibodies and those of the parent anti-CD30 antibodies are substantially homologous. For example, the variant anti-CD30 antibody sequences herein will possess about 80% homology with the parent anti-CD30 antibody sequence, preferably at least about 90% homology, and most preferably at least about 95% homology.

In a most preferred embodiment, the anti-CD30 antibodies of the present invention comprise amino acid modifications that provide optimized effector function properties relative to the parent. Most preferred substitutions and optimized effector function properties are described in U.S. Ser. No. 10/672,280, PCT US03/30249, and U.S. Ser. No. 10/822,231, and U.S. Ser. No. 60/627,774, filed Nov. 12, 2004 and entitled "Optimized Fc Variants". Properties that may be optimized include but are not limited to enhanced or reduced affinity for an FcγR. In a preferred embodiment, the anti-CD30 antibodies of the present invention are optimized to possess enhanced affinity for a human activating FcγR, preferably FcγRI, FcγRIIa, FcγRIIc, FcγRIIIa, and FcγRIIIb, most preferably FcγRIIIa. In an alternately preferred embodiment, the anti-CD30 antibodies are optimized to possess reduced affinity for the human inhibitory receptor FcγRIIb. These preferred embodiments are anticipated to provide anti-CD30 antibodies with enhanced therapeutic properties in humans, for example enhanced effector function and greater anti-cancer potency. In an alternate embodiment, the anti-CD30 antibodies of the present invention are optimized to have reduced or ablated affinity for a human FcγR, including but not limited to FcγRI, FcγRIIa, FcγRIIb, FcγRIIc, FcγRIIIa, and FcγRIIIb. These embodiments are anticipated to provide anti-CD30 antibodies with enhanced therapeutic properties in humans, for example reduced effector function and reduced toxicity. In other embodiments, anti-CD30 antibodies of the present invention provide enhanced affinity for one or more FcγRs, yet reduced affinity for one or more other FcγRs. For example, an anti-CD30 antibody of the present invention may have enhanced binding to FcγRIIIa, yet reduced binding to FcγRIIb. Alternately, an anti-CD30 antibody of the present invention may have enhanced binding to FcγRIIa and FcγRI, yet reduced binding to FcγRIIb. In yet another embodiment, an anti-CD30 antibody of the present invention may have enhanced affinity for FcγRIIb, yet reduced affinity to one or more activating FcγRs.

Preferred embodiments comprise optimization of Fc binding to a human FcγR, however in alternate embodiments the anti-CD30 antibodies of the present invention possess enhanced or reduced affinity for FcγRs from nonhuman organisms, including but not limited to rodents and non-human primates. anti-CD30 antibodies that are optimized for binding to a nonhuman FcγR may find use in experimentation. For example, mouse models are available for a variety of diseases that enable testing of properties such as efficacy, toxicity, and pharmacokinetics for a given drug candidate. As is known in the art, cancer cells can be grafted or injected into mice to mimic a human cancer, a process referred to as xenografting. Testing of anti-CD30 antibodies that comprise anti-CD30 antibodies that are optimized for one or more mouse FcγRs, may provide valuable information with regard to the efficacy of the protein, its mechanism of action, and the like. The anti-CD30 antibodies of the present invention may also be optimized for enhanced functionality and/or solution properties in aglycosylated form. In a preferred embodiment, the aglycosylated anti-CD30 antibodies of the present invention bind an Fc ligand with greater affinity than the aglycosylated form of the parent anti-CD30 antibody. Said Fc ligands include but are not limited to FcγRs, C1 g, FcRn, and proteins A and G, and may be from any source including but not limited to human, mouse, rat, rabbit, or monkey, preferably human. In an alternately preferred embodiment, the anti-CD30 antibodies are optimized to be more stable and/or more soluble than the aglycosylated form of the parent anti-CD30 antibody.

CD30 targeting proteins of the invention may comprise modifications that modulate interaction with Fc ligands other than FcγRs, including but not limited to complement proteins, FcRn, and Fc receptor homologs (FcRHs). FcRHs include but are not limited to FcRH1, FcRH2, FcRH3, FcRH4, FcRH5, and FcRH6 (Davis et al., 2002, Immunol. Reviews 190:123-136).

Preferably, the Fc ligand specificity of the anti-CD30 antibody of the present invention will determine its therapeutic utility. The utility of a given anti-CD30 antibody for therapeutic purposes will depend on the epitope or form of the CD30 target antigen and the disease or indication being treated. For some targets and indications, enhanced FcγR-mediated effector functions may be preferable. This may be particularly favorable for anti-cancer anti-CD30 antibodies. Thus anti-CD30 antibodies may be used that comprise anti-CD30 antibodies that provide enhanced affinity for activating FcγRs and/or reduced affinity for inhibitory FcγRs. For some targets and indications, it may be further beneficial to utilize anti-CD30 antibodies that provide differential selectivity for different activating FcγRs; for example, in some cases enhanced binding to FcγRIIa and FcγRIIIa may be desired, but not FcγRI, whereas in other cases, enhanced binding only to FcγRIIa may be preferred. For certain targets and indications, it may be preferable to utilize anti-CD30 antibodies that enhance both FcγR-mediated and complement-mediated effector functions, whereas for other cases it may be advantageous to utilize anti-CD30 antibodies that enhance either FcγR-mediated or complement-mediated effector functions. For some CD30 targets or cancer indications, it may be advantageous to reduce or ablate one or more effector functions, for example by knocking out binding to C1q, one or more FcγR's, FcRn, or one or more other Fc ligands. For other targets and indications, it may be preferable to utilize anti-CD30 antibodies that provide enhanced binding to the inhibitory FcγRIIb, yet WT level, reduced, or ablated binding to activating FcγRs. This may be particularly useful, for example, when the goal of an anti-CD30 antibody is to inhibit inflammation or auto-immune disease, or modulate the immune system in some way.

Clearly an important parameter that determines the most beneficial selectivity of a given anti-CD30 antibody to treat a given disease is the context of the anti-CD30 antibody, that is what type of anti-CD30 antibody is being used. Thus the Fc ligand selectivity or specificity of a given anti-CD30 antibody will provide different properties depending on whether it composes an antibody or an anti-CD30 antibodies with a coupled fusion or conjugate partner. For example, toxin, radionucleotide, or other conjugates may be less toxic to normal cells if the anti-CD30 antibody that comprises them has reduced or ablated binding to one or more Fc ligands. As another example, in order to inhibit inflammation or auto-immune disease, it may be preferable to utilize an anti-CD30 antibody with enhanced affinity for activating FcγRs, such as to bind these FcγRs and prevent their activation. Conversely, an anti-CD30 antibody that comprises two or more Fc regions with enhanced FcγRIIb affinity may co-engage this receptor on the surface of immune cells, thereby inhibiting proliferation of these cells. Whereas in some cases an anti-CD30 antibodies may engage its target antigen on one cell type yet engage FcγRs on separate cells from the target antigen, in other cases it may be advantageous to engage FcγRs on the surface of the same cells as the target antigen. For example, if an antibody targets an antigen on a cell that also expresses one or more FcγRs, it may be beneficial to utilize an anti-CD30 antibody that enhances or reduces binding to the FcγRs on the surface of that cell. This may be the case, for example when the anti-CD30 antibody is being used as an anti-cancer agent, and co-engagement of target antigen and FcγR on the surface of the same cell promote signaling events within the cell that result in growth inhibition, apoptosis, or other anti-proliferative effect. Alternatively, antigen and FcγR co-engagement on the same cell may be advantageous when the anti-CD30 antibody is being used to modulate the immune system in some way, wherein co-engagement of target antigen and FcγR provides some proliferative or anti-proliferative effect. Likewise, anti-CD30 antibodies that comprise two or more Fc regions may benefit from anti-CD30 antibodies that modulate FcγR selectivity or specificity to co-engage FcγRs on the surface of the same cell.

The Fc ligand specificity of the anti-CD30 antibodies of the present invention can be modulated to create different effector function profiles that may be suited for particular CD30 epitopes, indications or patient populations. Table 1 describes several preferred embodiments of receptor binding profiles that include improvements to, reductions to or no effect to the binding to various receptors, where such changes may be beneficial in certain contexts. The receptor binding profiles in the table could be varied by degree of increase or decrease to the specified receptors. Additionally, the binding changes specified could be in the context of additional binding changes to other receptors such as C1q or FcRn, for example by combining with ablation of binding to C1q to shut off complement activation, or by combining with enhanced binding to C1q to increase complement activation. Other embodiments with other receptor binding profiles are possible, the listed receptor binding profiles are exemplary.

TABLE 1

| Receptor binding improvement | Receptor binding reduction | Cell activity | Therapeutic activity |
| --- | --- | --- | --- |
| Solely I | — | enhance dendritic cell activity and uptake, and subsequence presentation of antigens; enhance monocyte and macrophage response to antibody | enhance cell-based immune response against target |
| IIIa | | Enhance ADCC and phagocytosis of broad range of cell types | Increased target cell lysis |
| IIIa | IIb | Enhance ADCC and phagocytosis of broad range of cell types | Increased target cell lysis |
| IIb, IIc | | Reduction of activity of all FcR bearing cell types except NK cells and possible activation of NK cells via IIc receptor signaling | Enhancement of target cell lysis selective for NK cell accessible target cells |
| IIb, IIIa | — | Possible NK cell specific activation and enhancement of NK cell mediated ADCC | Enhancement of target cell lysis selective for NK cell accessible target cells |
| IIIb | | Neutrophil mediated phagocytosis enhancement | Enhanced target cell destruction for neutrophil accessible cells |
| FcαR | | Neutrophil mediated phagocytosis enhancement | Enhanced target cell destruction for neutrophil accessible cells |
| I, IIa, IIIa | IIb | enhance dendritic cell activity and uptake, and subsequence presentation of antigens to T cells; enhance monocyte and macrophage response to antibody | enhance cell-based immune response against target |
| IIb | IIIa, IIa, I | Reduction in activity of monocytes, macrophages, neutrophils, NK, dendritic and other gamma receptor bearing cells | Eliminate or reduce cell-mediated cytotoxicity against target bearing cells |

The presence of different polymorphic forms of FcγRs provides yet another parameter that impacts the therapeutic utility of the anti-CD30 antibodies of the present invention. Whereas the specificity and selectivity of a given anti-CD30 antibody for the different classes of FcγRs significantly affects the capacity of an anti-CD30 antibody to target a given antigen for treatment of a given disease, the specificity or selectivity of an anti-CD30 antibody for different polymorphic forms of these receptors may in part determine which research or pre-clinical experiments may be appropriate for testing, and ultimately which patient populations may or may not respond to treatment. Thus the specificity or selectivity of anti-CD30 antibodies of the present invention to Fc ligand polymorphisms, including but not limited to FcγR, C1q, FcRn, and FcRH polymorphisms, may be used to guide the selection of valid research and pre-clinical experiments, clinical trial design, patient selection, dosing dependence, and/or other aspects concerning clinical trials.

The anti-CD30 antibodies of the present invention may be combined with other amino acid modifications in the Fc region that provide altered or optimized interaction with one or more Fc ligands, including but not limited to FcγRs, C1q, FcRn, FcR homologues, and/or as yet undiscovered Fc ligands. Additional modifications may provide altered or optimized affinity and/or specificity to the Fc ligands. Additional modifications may provide altered or optimized effector functions, including but not limited to ADCC, ADCP, CDC, and/or serum half-life. Such combination may provide additive, synergistic, or novel properties in antibodies. In one embodiment, the anti-CD30 antibodies of the present invention may be combined with known Fc variants (Duncan et al., 1988, *Nature* 332:563-564; Lund et al., 1991, *J Immunol* 147:2657-2662; Lund et al., 1992, *Mol Immunol* 29:53-59; Alegre et al., 1994, *Transplantation* 57:1537-1543; Hutchins et al., 1995, *Proc Natl Acad Sci USA* 92:11980-11984; Jefferis et al., 1995, *Immunol Lett* 44:111-117; Lund et al., 1995, *Faseb J* 9:115-119; Jefferis et al., 1996, *Immunol Lett* 54:101-104; Lund et al., 1996, *J Immunol* 157:4963-4969; Armour et al., 1999, *Eur J Immunol* 29:2613-2624; Idusogie et al., 2000, *J Immunol* 164:4178-4184; Reddy et al., 2000, *J Immunol* 164:1925-1933; Xu et al., 2000, *Cell Immunol* 200:16-26; Idusogie et al., 2001, *J Immunol* 166:2571-2575; Shields et al., 2001, *J Biol Chem* 276:6591-6604; Jefferis et al., 2002, *Immunol Lett* 82:57-65; Presta et al., 2002, *Biochem Soc Trans* 30:487-490; Hinton et al., 2004, *J Biol Chem* 279:6213-6216) (U.S. Pat. Nos. 5,624,821; 5,885,573; 6,194,551; PCT WO 00/42072; PCT WO 99/58572; US 2004/0002587 A1), U.S. Pat. No. 6,737,056, PCT US2004/000643, U.S. Ser. No. 10/370,749, and PCT/US2004/005112). For example, as described in U.S. Pat. No. 6,737,056, PCT US2004/000643, U.S. Ser. No. 10/370,749, and PCT/US2004/005112, the substitutions S298A, S298D, K326E, K326D, E333A, K334A, and P396L provide optimized FcγR binding and/or enhanced ADCC. Furthermore, as disclosed in Idusogie et al., 2001, J. Immunology 166:2571-2572, substitutions $K_{326}W$, K326Y, and E333S provide enhanced binding to the complement protein C1q and enhanced CDC. Finally, as described in Hinton et al., 2004, *J. Biol. Chem.* 279(8): 6213-6216, substitutions T250Q, T250E, M428L, and M428F provide enhanced binding to FcRn and improved pharmacokinetics. All references above entirely incorporated by reference.

Because the binding sites for FcγRs, C1q, and FcRn reside in the Fc region, the differences between the IgGs in the Fc region are likely to contribute to differences in FcγR- and C1q-mediated effector functions. It is also possible that the modifications can be made in other non-Fc regions of an anti-CD30 antibody, including for example the Fab and hinge regions of an antibody. For example, as disclosed in For example, as disclosed in U.S. Ser. No. 60/614,944, U.S. Ser. No. 60/619,409, and U.S. Ser. No. 11/090,981, each of which is incorporated by reference in its entirety, the Fab and hinge regions of an antibody may impact effector functions such as antibody dependent cell-mediated cytotoxicity (ADCC), antibody dependent cell-mediated phagocytosis (ADCP), and complement dependent cytotoxicity (CDC). Thus modifications outside the Fc region of an anti-CD30 antibody of the present invention are contemplated. For example, anti-CD30 antibodies of the present invention may comprise one or more amino acid modifications in the VL, CL, VH, CH1, and/or hinge regions of an antibody.

Other modifications may provide additional or novel binding determinants into an anti-CD30 antibody, for example additional or novel Fc receptor binding sites, for example as described in U.S. Ser. No. 60/531,752, filed Dec. 22, 2003 entirely incorporated by reference. In one embodiment, an anti-CD30 antibody of one antibody isotype may be engineered such that it binds to an Fc receptor of a different isotype. This may be particularly applicable when the Fc binding sites for the respective Fc receptors do not significantly overlap. For example, the structural determinants of IgA binding to FcγRI may be engineered into an IgG anti-CD30 antibody.

The anti-CD30 antibodies of the present invention may comprise modifications that modulate the in vivo pharmacokinetic properties of an anti-CD30 antibody. These include, but are not limited to, modifications that enhance affinity for the neonatal Fc receptor FcRn (U.S. Ser. No. 10/020,354; WO2001 US0048432; EP2001000997063; U.S. Pat. No. 6,277,375; U.S. Ser. No. 09/933,497; WO1997US0003321; U.S. Pat. No. 6,737,056; WO2000US0000973; Shields et al. J. Biol. Chem., 276(9), 6591-6604 (2001); Zhou et al. J. Mol. Biol., 332, 901-913 (2003), each of which is incorporated by reference in its entirety). These further include modifications that modify FcRn affinity in a pH-specific manner. In some embodiments, where enhanced in vivo half-life is desired, modifications that specifically enhance FcRn affinity at lower pH (5.5-6) relative to higher pH (7-8) are preferred (Hinton et al. J. Biol. Chem. 279(8), 6213-6216 (2004); Dall' Acqua et al. J. Immuno. 169, 5171-5180 (2002); Ghetie et al. Nat. Biotechnol., 15(7), 637-640 (1997); WO2003US0033037; and WO2004US0011213, each of which is incorporated by reference in its entirety). For example, as described in Hinton et al., 2004, "Engineered Human IgG Antibodies with Longer Serum Half-lives in Primates" J. Biol. Chem. 279(8): 6213-6216, substitutions T250Q, T250E, M428L, and M428F provide enhanced binding to FcRn and improved pharmacokinetics. Additionally preferred modifications are those that maintain the wild-type Fc's improved binding at lower pH relative to the higher pH. In alternative embodiments, where rapid in vivo clearance is desired, modifications that reduce affinity for FcRn are preferred. (U.S. Pat. No. 6,165,745; WO1993US0003895; EP1993000910800; WO1997US0021437; Medesan et al., J. Immunol., 158(5), 2211-2217 (1997); Ghetie and Ward, Annu. Rev. Immunol., 18, 739-766 (2000); Martin et al. Molecular Cell, 7, 867-877 (2001); Kim et al. Eur. J. Immunol. 29, 2819-2825 (1999), each of which is incorporated by reference in its entirety).

CD30 targeting proteins of the present invention may comprise one or more modifications that provide optimized properties that are not specifically related to effector function per se. Said modifications may be amino acid modifications, or may be modifications that are made enzymatically or chemically. Such modification(s) likely provide some improvement in the anti-CD30 antibody, for example an enhancement in its stability, solubility, function, or clinical use. The present invention contemplates a variety of improvements that made be made by coupling the anti-CD30 antibodies of the present invention with additional modifications.

In a preferred embodiment, the anti-CD30 antibodies of the present invention may comprise modifications to reduce immunogenicity in humans. In a most preferred embodiment, the immunogenicity of an anti-CD30 antibody of the present invention is reduced using a method described in U.S. Ser. No. 60/619,483, filed Oct. 14, 2004 and U.S. Ser. No. 11/004,590, entitled "Methods of Generating Variant Proteins with Increased Host String Content and Compositions Thereof," entirely incorporated by reference. In alternate embodiments, the antibodies of the present invention are humanized (Clark, 2000, *Immunol Today* 21:397-402, entirely incorporated by reference). By "humanized" antibody as used herein is meant an antibody comprising a human framework region (FR) and one or more complementarity determining regions (CDR's) from a non-human (usually mouse or rat) antibody. The non-human antibody providing the CDR's is called the "donor" and the human immunoglobulin providing the framework is called the "acceptor". Humanization relies principally on the grafting of donor CDRs onto acceptor (human) VL and VH frameworks (Winter U.S. Pat. No. 5,225,539, entirely incorporated by reference). This strategy is referred to as "CDR grafting". "Backmutation" of selected acceptor framework residues to the corresponding donor residues is often required to regain affinity that is lost in the initial grafted construct (U.S. Pat. Nos. 5,530,101; 5,585,089; 5,693,761; 5,693,762; 6,180,370; 5,859,205; 5,821,337; 6,054,297; 6,407,213, each of which is incorporated by reference in its entirety). The humanized antibody optimally also will comprise at least a portion of an immunoglobulin constant region, typically that of a human immunoglobulin, and thus will typically comprise a human Fc region. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein, each of which is incorporated by reference in its entirety). Humanization methods include but are not limited to methods described in Jones et al., 1986, Nature 321:522-525; Riechmann et al., 1988; Nature 332:323-329; Verhoeyen et al., 1988, *Science*, 239: 1534-1536; Queen et al., 1989, *Proc Natl Acad Sci, USA* 86:10029-33; He et al., 1998, *J. Immunol.* 160: 1029-1035; Carter et al., 1992, *Proc Natl Acad Sci USA* 89:4285-9; Presta et al., 1997, *Cancer Res.*57(20):4593-9; Gorman et al., 1991, *Proc. Natl. Acad. Sci. USA* 88:4181-4185; O'Connor et al., 1998, *Protein Eng* 11:321-8, each of which is incorporated by reference in its entirety. Humanization or other methods of reducing the immunogenicity of nonhuman antibody variable regions may include resurfacing methods, as described for example in Roguska et al., 1994, *Proc. Natl. Acad. Sci. USA* 91:969-973, entirely incorporated by reference. In one embodiment, selection based methods may be employed to humanize and/or affinity mature antibody variable regions, including but not limited to methods described in Wu et al., 1999, *J. Mol. Biol.* 294:151-162; Baca et al., 1997, *J. Biol. Chem.* 272(16):10678-10684; Rosok et al., 1996, *J. Biol. Chem.* 271(37): 22611-22618; Rader et al., 1998, *Proc. Natl. Acad. Sci. USA* 95: 8910-8915; Krauss et al., 2003, *Protein Engineering* 16(10):753-759, each of which is incorporated by reference in its entirety. Other humanization methods may involve the grafting of only parts of the CDRs, including but not limited to methods described in U.S. Ser. No. 09/810,502; Tan et al., 2002, *J. Immunol.* 169:1119-1125; De Pascalis et al., 2002, *J. Immunol.* 169:3076-3084, entirely incorporated by reference. Structure-based methods may be employed for humanization and affinity maturation, for example as described in U.S. Ser. No. 10/153,159 and related applications, each of which is incorporated by reference in its entirety.

In certain variations, as described more fully in Example 2, the immunogenicity of the antibody has been reduced using a method described in U.S. Ser. No. 60/619,483, filed Oct. 14, 2004 and U.S. Ser. No. 11/004,590, entitled "Methods of Generating Variant Proteins with Increased Host String Content and Compositions Thereof", filed on Dec. 3, 2004, both entirely incorporated by reference. In an alternate embodiment, the antibodies of the present invention may be fully human, that is the sequences of the antibodies are completely or substantially human. A number of methods are known in the art for generating fully human antibodies, including the use of transgenic mice (Bruggemann et al., 1997, *Curr Opin Biotechnol* 8:455-458, incorporated by reference in its entirety) or human antibody libraries coupled with selection methods (Griffiths et al., 1998, *Curr Opin Biotechnol* 9:102-108, incorporated by reference in its entirety).

Modifications to reduce immunogenicity may include modifications that reduce binding of processed peptides derived from the parent sequence to MHC proteins. For example, amino acid modifications would be engineered such that there are no or a minimal number of immune epitopes that are predicted to bind, with high affinity, to any prevalent MHC alleles. Several methods of identifying MHC-binding epitopes in protein sequences are known in the art and may be used to score epitopes in an anti-CD30 antibody of the present invention. See for example WO 98/52976; WO 02/079232; WO 00/3317; U.S. Ser. No. 09/903,378; 10/039,170; U.S. Ser. No. 60/222,697; U.S. Ser. No. 10/339,788; PCT WO 01/21823; and PCT WO 02/00165; Mallios, 1999, *Bioinformatics* 15: 432-439; Mallios, 2001, *Bioinformatics* 17: 942-948; Sturniolo et al., 1999, *Nature Biotech.* 17: 555-561; WO 98/59244; WO 02/069232; WO 02/77187; Marshall et al., 1995, *J. Immunol.* 154: 5927-5933; and Hammer et al., 1994, *J. Exp. Med.* 180: 2353-2358, each of which is incorporated by reference in its entirety. Sequence-based information can be used to determine a binding score for a given peptide—MHC interaction (see for example Mallios, 1999, *Bioinformatics* 15: 432-439; Mallios, 2001, *Bioinformatics* 17: p 942-948; Sturniolo et al., 1999, N*ature Biotech.* 17: 555-561, each of which is incorporated by reference in its entirety). It is possible to use structure-based methods in which a given peptide is computationally placed in the peptide-binding groove of a given MHC molecule and the interaction energy is determined (for example, see WO 98/59244 and WO 02/069232, both entirely incorporated by reference). Such methods may be referred to as "threading" methods. Alternatively, purely experimental methods can be used; for example a set of overlapping peptides derived from the protein of interest can be experimentally tested for the ability to induce T-cell activation and/or other aspects of an immune response. (see for example WO 02/77187, entirely incorporated by reference). In a preferred embodiment, MHC-binding propensity scores are calculated for each 9-residue frame along the protein sequence using a matrix method (see Sturniolo et. al., supra; Marshall et. al., 1995, *J. Immunol.* 154: 5927-5933, and Hammer et. al., 1994, *J. Exp. Med.* 180: 2353-2358, each of which is incorporated by reference in its entirety). It is also possible to consider scores for only a subset of these residues, or to consider also the identities of the peptide residues before and after the 9-residue frame of interest. The matrix comprises binding scores for specific amino acids interacting with the peptide binding pockets in different human class II MHC molecule. In the most preferred embodiment, the scores in the matrix are obtained from experimental peptide binding studies. In an alternate preferred embodiment, scores for a given amino acid binding to a given pocket are extrapolated from experimentally characterized alleles to additional alleles with identical or similar residues lining that pocket. Matrices that are produced by extrapolation are referred to as "virtual matrices". In an alternate embodiment, additional amino acid modifications may be engineered to reduce the propensity of the intact molecule to interact with B cell receptors and circulating antibodies.

Anti-CD30 antibodies of the present invention may comprise amino acid modifications in one or more regions outside the Fc region, for example the antibody Fab region, that provide optimal properties. In one embodiment, the variable region of an antibody of the present invention may be affinity matured, that is to say that amino acid modifications have been made in the VH and/or VL domains of the antibody to enhance binding of the antibody to its target antigen. Such types of modifications may improve the association and/or the dissociation kinetics for binding to the target antigen. Other modifications include those that improve selectivity for target antigen vs. alternative targets. These include modifications that improve selectivity for antigen expressed on target vs. non-target cells. Other improvements to the target recognition properties may be provided by additional modifications. Such properties may include, but are not limited to, specific kinetic properties (i.e. association and dissociation kinetics), selectivity for the particular target versus alternative targets, and selectivity for a specific form of target versus alternative forms. Examples include full-length versus splice variants, cell-surface vs. soluble forms, selectivity for various polymorphic variants, or selectivity for specific conformational forms of the CD30 target.

CD30 targeting proteins of the invention may comprise one or more modifications that provide reduced or enhanced internalization of an anti-CD30 antibody. In one embodiment, anti-CD30 antibodies of the present invention can be utilized or combined with additional modifications in order to reduce the cellular internalization of an anti-CD30 antibody that occurs via interaction with one or more Fc ligands. This property might be expected to enhance effector function, and potentially reduce immunogenicity of the anti-CD30 antibodies of the invention. Alternatively, anti-CD30 antibodies of the present anti-CD30 antibodies of the present invention can be utilized directly or combined with additional modifications in order to enhance the cellular internalization of an anti-CD30 antibody that occurs via interaction with one or more Fc ligands. For example, in a preferred embodiment, an anti-CD30 antibody is used that provides enhanced binding to FcγRI, which is expressed on dendritic cells and active early in immune response. This strategy could be further enhanced by combination with additional modifications, either within the anti-CD30 antibody or in an attached fusion or conjugate partner, that promote recognition and presentation of Fc peptide fragments by MHC molecules. These strategies are expected to enhance target antigen processing and thereby improve antigenicity of the target antigen (Bonnerot and Amigorena, 1999, *Immunol Rev.* 172:279-84, entirely incorporated by reference), promoting an adaptive immune response and greater target cell killing by the human immune system. These strategies may be particularly advantageous when the targeted antigen is shed from the cellular surface. An additional application of these concepts arises with idiotype vaccine immunotherapies, in which clone-specific antibodies produced by a patient's lymphoma cells are used to vaccinate the patient.

In a preferred embodiment, modifications are made to improve biophysical properties of the anti-CD30 antibodies of the present invention, including but not limited to stability, solubility, and oligomeric state. Modifications can include, for example, substitutions that provide more favorable intramolecular interactions in the anti-CD30 antibody such as to provide greater stability, or substitution of exposed nonpolar amino acids with polar amino acids for higher solubility. A number of optimization goals and methods are described in U.S. Ser. No. 10/379,392, entirely incorporated by reference, that may find use for engineering additional modifications to further optimize the anti-CD30 antibodies of the present invention. The anti-CD30 antibodies of the present invention can also be combined with additional modifications that reduce oligomeric state or size, such that tumor penetration is enhanced, or in vivo clearance rates are increased as desired.

Other modifications to the anti-CD30 antibodies of the present invention include those that enable the specific formation or homodimeric or homomultimeric molecules. Such modifications include but are not limited to engineered disulfides, as well as chemical modifications or aggregation methods which may provide a mechanism for generating covalent homodimeric or homomultimers. For example, methods of engineering and compositions of such molecules are described in Kan et al., 2001, *J. Immunol.*, 2001, 166: 1320-1326; Stevenson et al., 2002, *Recent Results Cancer Res.* 159: 104-12; U.S. Pat. No. 5,681,566; Caron et al., 1992, *J. Exp. Med.* 176:1191-1195, and Shopes, 1992, *J. Immunol.* 148(9):2918-22, each of which is incorporated by reference in its entirety. Additional modifications to the variants of the present invention include those that enable the specific formation or heterodimeric, heteromultimeric, bifunctional, and/or multifunctional molecules. Such modifications include, but are not limited to, one or more amino acid substitutions in the CH3 domain, in which the substitutions reduce homodimer formation and increase heterodimer formation. For example, methods of engineering and compositions of such molecules are described in Atwell et al., 1997, *J. Mol. Biol.* 270(1):26-35, and Carter et al., 2001, *J. Immunol. Methods* 248:7-15, both entirely incorporated by reference. Additional modifications include modifications in the hinge and CH3 domains, in which the modifications reduce the propensity to form dimers.

In further embodiments, the anti-CD30 antibodies of the present invention comprise modifications that remove proteolytic degradation sites. These may include, for example, protease sites that reduce production yields, as well as protease sites that degrade the administered protein in vivo. In a preferred embodiment, additional modifications are made to remove covalent degradation sites such as deamidation (i.e. deamidation of glutaminyl and asparaginyl residues to the corresponding glutamyl and aspartyl residues), oxidation, and proteolytic degradation sites. Deamidation sites that are particular useful to remove are those that have enhance propensity for deamidation, including, but not limited to asparaginyl and gltuamyl residues followed by glycines (NG and QG motifs, respectively). In such cases, substitution of either residue can significantly reduce the tendency for deamidation. Common oxidation sites include methionine and cysteine residues. Other covalent modifications, that can either be introduced or removed, include hydroxylation of proline and lysine, phosphorylation of hydroxyl groups of seryl or threonyl residues, methylation of the "—amino groups of lysine, arginine, and histidine side chains (T. E. Creighton, Proteins: Structure and Molecular Properties, W.H. Freeman & Co., San Francisco, pp. 79-86 (1983), entirely incorporated by reference), acetylation of the N-terminal amine, and amidation of any C-terminal carboxyl group. Additional modifications also may include but are not limited to posttranslational modifications such as N-linked or O-linked glycosylation and phosphorylation.

Modifications may include those that improve expression and/or purification yields from hosts or host cells commonly used for production of biologics. These include, but are not limited to various mammalian cell lines (e.g. CHO), yeast cell lines, bacterial cell lines, and plants. Additional modifications include modifications that remove or reduce the ability of heavy chains to form inter-chain disulfide linkages. Additional modifications include modifications that remove or reduce the ability of heavy chains to form intra-chain disulfide linkages.

The anti-CD30 antibodies of the present invention may comprise modifications that include the use of unnatural amino acids incorporated using, for example, the technologies developed by Schultz and colleagues, including but not limited to methods described by Cropp & Shultz, 2004, Trends Genet. 20(12):625-30, Anderson et al., 2004, Proc. Natl. Acad. Sci. U.S.A. 101(2):7566-71, Zhang et al., 2003, 303(5656):371-3, and Chin et al., 2003, Science 301(5635): 964-7, each of which is incorporated by reference in its entirety. In some embodiments, these modifications enable manipulation of various functional, biophysical, immunological, or manufacturing properties discussed above. In additional embodiments, these modifications enable additional chemical modification for other purposes. Other modifications are contemplated herein. For example, the anti-CD30 antibody may be linked to one of a variety of nonproteinaceous polymers, e.g., polyethylene glycol (PEG), polypropylene glycol, polyoxyalkylenes, or copolymers of polyethylene glycol and polypropylene glycol. Additional amino acid modifications may be made to enable specific or non-specific chemical or posttranslational modification of the anti-CD30 antibodies. Such modifications, include, but are not limited to PEGylation and glycosylation. Specific substitutions that can be utilized to enable PEGylation include, but are not limited to, introduction of novel cysteine residues or unnatural amino acids such that efficient and specific coupling chemistries can be used to attach a PEG or otherwise polymeric moiety. Introduction of specific glycosylation sites can be achieved by introducing novel N-X-T/S sequences into the anti-CD30 antibodies of the present invention.

Glycoform Modification

Many polypeptides, including antibodies, are subjected to a variety of post-translational modifications involving carbohydrate moieties, such as glycosylation with oligosaccharides. There are several factors that can influence glycosylation. The species, tissue and cell type have all been shown to be important in the way that glycosylation occurs. In addition, the extracellular environment, through altered culture conditions such as serum concentration, may have a direct effect on glycosylation. (Lifely et al., 1995, Glycobiology 5(8): 813-822).

All antibodies contain carbohydrate at conserved positions in the constant regions of the heavy chain. Each antibody isotype has a distinct variety of N-linked carbohydrate structures. Aside from the carbohydrate attached to the heavy chain, up to 30% of human IgGs have a glycosylated Fab region. IgG has a single N-linked biantennary carbohydrate at Asn297 of the CH2 domain. For IgG from either serum or produced ex vivo in hybridomas or engineered cells, the IgG are heterogeneous with respect to the Asn297 linked carbohydrate. Jefferis et al., 1998, Immunol. Rev. 163:59-76; and Wright et al., 1997, Trends Biotech 15:26-32. For human IgG, the core oligosaccharide normally consists of $GlcNAc_2Man_3GlcNAc$, with differing numbers of outer residues.

The carbohydrate moieties of the present invention will be described with reference to commonly used nomenclature for the description of oligosaccharides. A review of carbohydrate chemistry which uses this nomenclature is found in Hubbard et al. 1981, Ann. Rev. Biochem. 50:555-583. This nomenclature includes, for instance, Man, which represents mannose; GlcNAc, which represents 2-N-acetylglucosamine; Gal which represents galactose; Fuc for fucose; and Glc, which represents glucose. Sialic acids are described by the shorthand notation NeuNAc, for 5-N-acetyl-neuraminic acid, and NeuNGc for 5-glycolylneuraminic.

The term "glycosylation" means the attachment of oligosaccharides (carbohydrates containing two or more simple sugars linked together e.g. from two to about twelve simple sugars linked together) to a glycoprotein. The oligosaccharide side chains are typically linked to the backbone of the glycoprotein through either N- or O-linkages. The oligosaccharides of the present invention occur generally are attached to a CH2 domain of an Fc region as N-linked oligosaccharides. "N-linked glycosylation" refers to the attachment of the carbohydrate moiety to an asparagine residue in a glycoprotein chain. The skilled artisan will recognize that, for example, each of murine IgG1, IgG2a, IgG2b and IgG3 as well as human IgG1, IgG2, IgG3, IgG4, IgA and IgD CH2 domains have a single site for N-linked glycosylation at amino acid residue 297 (Kabat et al. Sequences of Proteins of Immunological Interest, 1991).

For the purposes herein, a "mature core carbohydrate structure" refers to a processed core carbohydrate structure attached to an Fc region which generally consists of the following carbohydrate structure $GlcNAc(Fucose)$-$GlcNAc$-$Man$-$(Man$-$GlcNAc)_2$ typical of biantennary oligosaccharides. The mature core carbohydrate structure is attached to the Fc region of the glycoprotein, generally via N-linkage to Asn297 of a CH2 domain of the Fc region. A "bisecting GlcNAc" is a GlcNAc residue attached to the β1,4 mannose of the mature core carbohydrate structure. The bisecting GlcNAc can be enzymatically attached to the mature core carbohydrate structure by a β(1,4)-N-acetylglucosaminyl-transferase III enzyme (GnTIII). CHO cells do not normally express GnTIII (Stanley et al., 1984, J. Biol. Chem. 261: 13370-13378), but may be engineered to do so (Umana et al., 1999, Nature Biotech. 17:176-180).

The present invention contemplates Fc variants that comprise modified glycoforms or engineered glycoforms. By "modified glycoform" or "engineered glycoform" as used herein is meant a carbohydrate composition that is covalently attached to an IgG, wherein said carbohydrate composition differs chemically from that of a parent IgG. Engineered glycoforms may be useful for a variety of purposes, including but not limited to enhancing or reducing FcγR-mediated effector function. In a preferred embodiment, the Fc variants of the present invention are modified to control the level of fucosylated and/or bisecting oligosaccharides that are covalently attached to the Fc region. A variety of methods are well known in the art for generating modified glycoforms (Umaña et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473); (U.S. Pat. No. 6,602,684; U.S. Ser. Nos. 10/277,370; 10/113,929; PCT WO 00/61739A1; PCT WO 01/29246A1; PCT WO 02/31140A1; PCT WO 02/30954A1); (Potelligent™ technology [Biowa, Inc., Princeton, N.J.]; GlycoMAb™ glycosylation engineering technology [GLYCART biotechnology AG, Zurich, Switzerland]; all of which are expressly incorporated by reference). These techniques control the level of fucosylated and/or bisecting oligosaccharides that are covalently attached to the Fc region, for example by expressing an IgG in various organisms or cell lines, engineered or otherwise (for example Lec-13 CHO cells or rat hybridoma YB2/0 cells), by regulating enzymes involved in the glycosylation pathway (for example FUT8[α1,6-fucosyltranserase] and/or β1-4-N-acetylglucosaminyltransferase III [GnTIII]), or by modifying carbohydrate(s) after the IgG has been expressed. The use of a particular mode of generating a modified glycoform, for example the use of the Lec-13 cell line in the present study, is not meant to constrain the present invention to that particular embodiment. Rather, the present invention contemplates Fc variants with modified glycoforms irrespective of how they are produced. Engineered glycoform typically refers to the different carbohydrate or oligosaccharide; thus an anti-CD30 antibody, for example an anti-CD30 antibody, may comprise an engineered glycoform. Alternatively, engineered glycoform may refer to the anti-CD30 antibody that comprises the different carbohydrate or oligosaccharide.

Engineered glycoform typically refers to the different carbohydrate or oligosaccharide; thus an IgG variant, for example an antibody or Fc fusion, can include an engineered glycoform. Alternatively, engineered glycoform may refer to the IgG variant that comprises the different carbohydrate or oligosaccharide. For the purposes herein, a "parent Fc polypeptide" is a glycosylated Fc polypeptide having the same amino acid sequence and mature core carbohydrate structure as an engineered glycoform of the present invention, except that fucose is attached to the mature core carbohydrate structure. For instance, in a composition comprising the parent glycoprotein about 50-100% or about 70-100% of the parent glycoprotein comprises a mature core carbohydrate structure having fucose attached thereto.

The present invention provides a composition comprising a glycosylated Fc polypeptide having an Fc region, wherein about 51-100% of the glycosylated Fc polypeptide in the composition comprises a mature core carbohydrate structure which lacks fucose, attached to the Fc region of the Fc polypeptide. More preferably, about 80-100% of the Fc polypeptide in the composition comprises a mature core carbohydrate structure which lacks fucose and most preferably about 90-99% of the Fc polypeptide in the composition lacks fucose attached to the mature core carbohydrate structure. In a most preferred embodiment, the Fc polypeptide in the composition both comprises a mature core carbohydrate structure that lacks fucose and additionally comprises at least one amino acid modification in the Fc region. In the most preferred embodiment, the combination of engineered glycoform and amino acid modification provides optimal Fc receptor binding properties to the Fc polypeptide. The anti-CD30 antibodies of the present invention may be fused or conjugated to one or more other molecules or polypeptides. Conjugate and fusion partners may be any molecule, including small molecule chemical compounds and polypeptides. For example, a variety of antibody conjugates and methods are described in Trail et al., 1999, Curr. Opin. Immunol. 11:584-588, entirely incorporated by reference. Possible conjugate partners include but are not limited to cytokines, cytotoxic agents, toxins, radioisotopes, chemotherapeutic agent, anti-angiogenic agents, a tyrosine kinase inhibitors, and other therapeutically active agents. In some embodiments, conjugate partners may be thought of more as payloads, that is to say that the goal of a conjugate is targeted delivery of the conjugate partner to a targeted cell, for example a cancer cell or immune cell, by the anti-CD30 antibody. Thus, for example, the conjugation of a toxin to an anti-CD30 antibody targets the delivery of said toxin to cells expressing the CD30 antigen. As will be appreciated by one skilled in the art, in reality the concepts and definitions of fusion and conjugate are overlapping. The designation of an anti-CD30 antibody as a fusion or conjugate is not meant to constrain it to any particular embodiment of the present invention. Rather, these terms are used loosely to convey the broad concept that any anti-CD30 antibody of the present invention may be linked genetically, chemically, or otherwise, to one or more polypeptides or molecules to provide some desirable property.

In one embodiment, the anti-CD30 antibodies of the present invention are fused or conjugated to a cytokine. By "cytokine" as used herein is meant a generic term for proteins released by one cell population that act on another cell as intercellular mediators. For example, as described in Penichet et al., 2001, J. Immunol. Methods 248:91-101, entirely incorporated by reference, cytokines may be fused to antibody to provide an array of desirable properties. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1 alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; C5a; and other polypeptide factors including LIF and kit ligand (KL). As used herein, the term cytokine includes proteins from natural sources or from recombinant cell culture, and biologically active equivalents of the native sequence cytokines.

In an alternate embodiment, the anti-CD30 antibodies of the present invention are fused, conjugated, or operably linked to a toxin, including but not limited to small molecule toxins and enzymatically active toxins of bacterial, fungal, plant or animal origin, including fragments and/or variants thereof. For example, a variety of immunotoxins and immunotoxin methods are described in Thrush et al., 1996, Ann. Rev. Immunol. 14:49-71, entirely incorporated by reference. Small molecule toxins include but are not limited to calicheamicin, maytansine (U.S. Pat. No. 5,208,020, entirely incorporated by reference), trichothene, and CC1065. In one embodiment of the invention, the anti-CD30 antibody is conjugated to one or more maytansine molecules (e.g. about 1 to about 10 maytansine molecules per antibody molecule). Maytansine may, for example, be converted to May-SS-Me which may be reduced to May-SH3 and reacted with modified antibody (Chari et al., 1992, *Cancer Research* 52: 127-131, entirely incorporated by reference) to generate a maytansinoid-antibody conjugate. Another conjugate of interest comprises an anti-CD30 antibody conjugated to one or more calicheamicin molecules. The calicheamicin family of antibiotics are capable of producing double-stranded DNA breaks at sub-picomolar concentrations. Structural analogues of calicheamicin that may be used include but are not limited to $\gamma_1^1$, $\alpha_2^1$, $\alpha_3$, N-acetyl-$\gamma_1^1$, PSAG, and $\Theta_1$, (Hinman et al., 1993, Cancer Research 53:3336-3342; Lode et al., 1998, Cancer Research 58:2925-2928) (U.S. Pat. Nos. 5,714,586; 5,712,374; 5,264,586; 5,773,001, each of which is incorporated by reference in its entirety). Dolastatin 10 analogs such as auristatin E (AE) and monomethylauristatin E (MMAE) may find use as conjugates for the anti-CD30 antibodies of the present invention (Doronina et al., 2003, Nat Biotechnol 21(7):778-84; Francisco et al., 2003 Blood 102(4):1458-65, both entirely incorporated by reference). Useful enyzmatically active toxins include but are not limited to diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, PCT WO 93/21232, entirely incorporated by reference. The present invention further contemplates a conjugate between an anti-CD30 antibody of the present invention and a compound with nucleolytic activity, for example a ribonuclease or DNA endonuclease such as a deoxyribonuclease (Dnase).

In an alternate embodiment, an anti-CD30 antibody of the present invention may be fused, conjugated, or operably linked to a radioisotope to form a radioconjugate. A variety of radioactive isotopes are available for the production of radioconjugate antibodies. Examples include, but are not limited to, At211, I113, I125, Y90, Re186, Re188, Sm153, Bi212, P32, and radioactive isotopes of Lu. See for example, reference.

In yet another embodiment, an anti-CD30 antibody of the present invention may be conjugated to a "receptor" (such streptavidin) for utilization in tumor pretargeting wherein the anti-CD30 antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide). In an alternate embodiment, the anti-CD30 antibody is conjugated or operably linked to an enzyme in order to employ Antibody Dependent Enzyme Mediated Prodrug Therapy (ADEPT). ADEPT may be used by conjugating or operably linking the anti-CD30 antibody to a prodrug-activating enzyme that converts a prodrug (e.g. a peptidyl chemotherapeutic agent, see PCT WO 81/01145, entirely incorporated by reference) to an active anti-cancer drug. See, for example, PCT WO 88/07378 and U.S. Pat. No. 4,975,278, both entirely incorporated by reference. The enzyme component of the immunoconjugate useful for ADEPT includes any enzyme capable of acting on a prodrug in such a way so as to covert it into its more active, cytotoxic form. Enzymes that are useful in the method of this invention include but are not limited to alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as .beta.-galactosidase and neuramimidase useful for converting glycosylated prodrugs into free drugs; beta-lactamase useful for converting drugs derivatized with .alpha.-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, for example, Massey, 1987, Nature 328: 457-458, entirely incorporated by reference). Anti-CD30 antibody-abzyme conjugates can be prepared for delivery of the abzyme to a tumor cell population. A variety of additional conjugates are contemplated for the anti-CD30 antibodies of the present invention. A variety of chemotherapeutic agents, anti-angiogenic agents, tyrosine kinase inhibitors, and other therapeutic agents are described below, which may find use as anti-CD30 antibody conjugates.

Also contemplated as fusion and conjugate partners are Fc polypeptides. Thus an anti-CD30 antibody may be a multimeric Fc polypeptide, comprising two or more Fc regions. The advantage of such a molecule is that it provides multiple binding sites for Fc receptors with a single protein molecule. In one embodiment, Fc regions may be linked using a chemical engineering approach. For example, Fab' s and Fc's may be linked by thioether bonds originating at cysteine residues in the hinges, generating molecules such as FabFc$_2$ (Kan et al., 2001, *J. Immunol.*, 2001, 166: 1320-1326; Stevenson et al., 2002, *Recent Results Cancer Res.* 159: 104-12; U.S. Pat. No. 5,681,566, each of which is incorporated by reference in its entirety). Fc regions may be linked using disulfide engineering and/or chemical cross-linking, for example as described in Caron et al., 1992, J. Exp. Med. 176:1191-1195, and Shopes, 1992, J. Immunol. 148(9):2918-22. In a preferred embodiment, Fc regions may be linked genetically. For example multiple Cγ2 domains have been fused between the Fab and Fc regions of an antibody (White et al., 2001, *Protein Expression and Purification* 21: 446-455, entirely incorporated by reference). In a preferred embodiment, Fc regions in an anti-CD30 antibody are linked genetically to generated tandemly linked Fc regions as described in U.S. Ser. No. 60/531,752, filed Dec. 22, 2003, entitled "Fc polypeptides with novel Fc receptor binding sites," entirely incorporated by reference. Tandemly linked Fc polypeptides may comprise two or more Fc regions, preferably one to three, most preferably two Fc regions. It may be advantageous to explore a number of engineering constructs in order to obtain homo- or heterotandemly linked anti-CD30 antibodies with the most favorable structural and functional properties. Tandemly linked anti-CD30 antibodies may be homo-tandemly linked anti-CD30 antibodies, that is an anti-CD30 antibody of one isotype is fused genetically to another anti-CD30 antibody of the same isotype. It is anticipated that because there are multiple FcγR, C1q, and/or FcRn binding sites on tandemly linked Fc polypeptides, effector functions and/or pharmacokinetics may be enhanced. In an alternate embodiment, anti-CD30 antibodies from different isotypes may be tandemly linked, referred to as hetero-tandemly linked anti-CD30 antibodies. For example, because of the capacity to target FcγR and FcαRI receptors, an anti-CD30 antibody that binds both FcγRs and FcαRI may provide a significant clinical improvement.

Fusion and conjugate partners may be linked to any region of an anti-CD30 antibody of the present invention, including at the N- or C-termini, or at some residue in-between the termini. In a preferred embodiment, a fusion or conjugate partner is linked at the N- or C-terminus of the anti-CD30 antibody, most preferably the N-terminus. A variety of linkers may find use in the present invention to covalently link anti-CD30 antibodies to a fusion or conjugate partner. By "linker", "linker sequence", "spacer", "tethering sequence" or grammatical equivalents thereof, herein is meant a molecule or group of molecules (such as a monomer or polymer) that connects two molecules and often serves to place the two molecules in a preferred configuration. A number of strategies may be used to covalently link molecules together. These include, but are not limited to polypeptide linkages between N- and C-termini of proteins or protein domains, linkage via disulfide bonds, and linkage via chemical cross-linking reagents. In one aspect of this embodiment, the linker is a peptide bond, generated by recombinant techniques or peptide synthesis. Choosing a suitable linker for a specific case where two polypeptide chains are to be connected depends on various parameters, including but not limited to the nature of the two polypeptide chains (e.g., whether they naturally oligomerize), the distance between the N- and the C-termini to be connected if known, and/or the stability of the linker towards proteolysis and oxidation. Furthermore, the linker may contain amino acid residues that provide flexibility. Thus, the linker peptide may predominantly include the following amino acid residues: Gly, Ser, Ala, or Thr. The linker peptide should have a length that is adequate to link two molecules in such a way that they assume the correct conformation relative to one another so that they retain the desired activity. Suitable lengths for this purpose include at least one and not more than 50 amino acid residues. Preferably, the linker is from about 1 to 30 amino acids in length, with linkers of 1 to 20 amino acids in length being most preferred. In addition, the amino acid residues selected for inclusion in the linker peptide should exhibit properties that do not interfere significantly with the activity of the polypeptide. Thus, the linker peptide on the whole should not exhibit a charge that would be inconsistent with the activity of the polypeptide, or interfere with internal folding, or form bonds or other interactions with amino acid residues in one or more of the monomers that would seriously impede the binding of receptor monomer domains. Useful linkers include glycine-serine polymers (including, for example, (GS)n, (GSGGS)n (GGGGS)n and (GGGS)n, where n is an integer of at least one), glycine-alanine polymers, alanine-serine polymers, and other flexible linkers such as the tether for the shaker potassium channel, and a large variety of other flexible linkers, as will be appreciated by those in the art. Glycine-serine polymers are preferred since both of these amino acids are relatively unstructured, and therefore may be able to serve as a neutral tether between components. Secondly, serine is hydrophilic and therefore able to solubilize what could be a globular glycine chain. Third, similar chains have been shown to be effective in joining subunits of recombinant proteins such as single chain antibodies. Suitable linkers may also be identified by screening databases of known three-dimensional structures for naturally occurring motifs that can bridge the gap between two polypeptide chains. In a preferred embodiment, the linker is not immunogenic when administered in a human patient. Thus linkers may be chosen such that they have low immunogenicity or are thought to have low immunogenicity. For example, a linker may be chosen that exists naturally in a human. In a most preferred embodiment, the linker has the sequence of the hinge region of an antibody, that is the sequence that links the antibody Fab and Fc regions; alternatively the linker has a sequence that comprises part of the hinge region, or a sequence that is substantially similar to the hinge region of an antibody. Another way of obtaining a suitable linker is by optimizing a simple linker, e.g., (Gly4Ser)n, through random mutagenesis. Alternatively, once a suitable polypeptide linker is defined, additional linker polypeptides can be created to select amino acids that more optimally interact with the domains being linked. Other types of linkers that may be used in the present invention include artificial polypeptide linkers and inteins. In another embodiment, disulfide bonds are designed to link the two molecules. In another embodiment, linkers are chemical cross-linking agents. For example, a variety of bifunctional protein coupling agents may be used, including but not limited to N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., 1971, Science 238:1098, entirely incorporated by reference. Chemical linkers may enable chelation of an isotope. For example, Carbon-14-labeled 1-isothiocyanatobenzyl-3-methyldiethylene triaminepentaacetic acid (MX-DTPA) is an exemplary chelating agent for conjugation of radionucleotide to the antibody (see PCT WO 94/11026, entirely incorporated by reference). The linker may be cleavable, facilitating release of the cytotoxic drug in the cell. For example, an acid-labile linker, peptidase-sensitive linker, dimethyl linker or disulfide-containing linker (e.g., Chari et al., 1992, Cancer Research 52: 127-131, entirely incorporated by reference) may be used. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers, that is may find use to link the anti-CD30 antibodies of the present invention to a fusion or conjugate partner, or to link the anti-CD30 antibodies of the present invention to a conjugate.

Experimental Production of Anti-CD30 Antibodies

The present invention provides methods for producing and experimentally testing anti-CD30 antibodies. The described methods are not meant to constrain the present invention to any particular application or theory of operation. Rather, the provided methods are meant to illustrate generally that one or more anti-CD30 antibodies may be produced and experimentally tested to obtain variant anti-CD30 antibodies. General methods for antibody molecular biology, expression, purification, and screening are described in Antibody Engineering, edited by Duebel & Kontermann, Springer-Verlag, Heidelberg, 2001; and Hayhurst & Georgiou, 2001, *Curr Opin Chem Biol* 5:683-689; Maynard & Georgiou, 2000, *Annu Rev Biomed Eng* 2:339-76; Antibodies: A Laboratory Manual by Harlow & Lane, New York: Cold Spring Harbor Laboratory Press, 1988, each of which is incorporated by reference in its entirety.

In one embodiment of the present invention, nucleic acids are created that encode the anti-CD30 antibodies, and that may then be cloned into host cells, expressed and assayed, if desired. Thus, nucleic acids, and particularly DNA, may be made that encode each protein sequence. These practices are carried out using well-known procedures. For example, a variety of methods that may find use in the present invention are described in Molecular Cloning—A Laboratory Manual, $3^{rd}$ Ed. (Maniatis, Cold Spring Harbor Laboratory Press, New York, 2001), and Current Protocols in Molecular Biology (John Wiley & Sons), both entirely incorporated by reference. As will be appreciated by those skilled in the art, the generation of exact sequences for a library comprising a large number of sequences is potentially expensive and time consuming. Accordingly, there are a variety of techniques that may be used to efficiently generate libraries of the present invention. Such methods that may find use in the present invention are described or referenced in U.S. Pat. No. 6,403,312; U.S. Ser. Nos. 09/782,004; 09/927,790; 10/218,102; PCT WO 01/40091; and PCT WO 02/25588, each of which is incorporated by reference in its entirety. Such methods include but are not limited to gene assembly methods, PCR-based method and methods which use variations of PCR, ligase chain reaction-based methods, pooled oligo methods such as those used in synthetic shuffling, error-prone amplification methods and methods which use oligos with random mutations, classical site-directed mutagenesis methods, cassette mutagenesis, and other amplification and gene synthesis methods. As is known in the art, there are a variety of commercially available kits and methods for gene assembly, mutagenesis, vector subcloning, and the like, and such commercial products find use in the present invention for generating nucleic acids that encode anti-CD30 antibodies.

The anti-CD30 antibodies of the present invention may be produced by culturing a host cell transformed with nucleic acid, preferably an expression vector, containing nucleic acid encoding the anti-CD30 antibodies, under the appropriate conditions to induce or cause expression of the protein. The conditions appropriate for expression will vary with the choice of the expression vector and the host cell, and will be easily ascertained by one skilled in the art through routine experimentation. A wide variety of appropriate host cells may be used, including but not limited to mammalian cells, bacteria, insect cells, and yeast. For example, a variety of cell lines that may find use in the present invention are described in the ATCC® cell line catalog, available from the American Type Culture Collection.

In a preferred embodiment, the anti-CD30 antibodies are expressed in mammalian expression systems, including systems in which the expression constructs are introduced into the mammalian cells using virus such as retrovirus or adenovirus. Any mammalian cells may be used, with human, mouse, rat, hamster, and primate cells being particularly preferred. Suitable cells also include known research cells, including but not limited to Jurkat T cells, NIH3T3, CHO, BHK, COS, HEK293, PER C.6, HeLa, Sp2/0, NS0 cells and variants thereof. In an alternately preferred embodiment, library proteins are expressed in bacterial cells. Bacterial expression systems are well known in the art, and include *Escherichia coli* (*E. coil*), *Bacillus subtilis, Streptococcus cremoris,* and *Streptococcus lividans*. In alternate embodiments, anti-CD30 antibodies are produced in insect cells (e.g. Sf21/Sf9, *Trichoplusia ni* Bti-Tn5b1-4) or yeast cells (e.g. *S. cerevisiae, Pichia*, etc). In an alternate embodiment, anti-CD30 antibodies are expressed in vitro using cell free translation systems. In vitro translation systems derived from both prokaryotic (e.g. *E. coli*) and eukaryotic (e.g. wheat germ, rabbit reticulocytes) cells are available and may be chosen based on the expression levels and functional properties of the protein of interest. For example, as appreciated by those skilled in the art, in vitro translation is required for some display technologies, for example ribosome display. In addition, the anti-CD30 antibodies may be produced by chemical synthesis methods. Also transgenic expression systems both animal (e.g. cow, sheep or goat milk, embryonated hen's eggs, whole insect larvae, etc.) and plant (e.g. corn, tobacco, duckweed, etc.)

The nucleic acids that encode the anti-CD30 antibodies of the present invention may be incorporated into an expression vector in order to express the protein. A variety of expression vectors may be utilized for protein expression. Expression vectors may comprise self-replicating extra-chromosomal vectors or vectors which integrate into a host genome. Expression vectors are constructed to be compatible with the host cell type. Thus expression vectors which find use in the present invention include but are not limited to those which enable protein expression in mammalian cells, bacteria, insect cells, yeast, and in in vitro systems. As is known in the art, a variety of expression vectors are available, commercially or otherwise, that may find use in the present invention for expressing anti-CD30 antibodies.

Expression vectors typically comprise a protein operably linked with control or regulatory sequences, selectable markers, any fusion partners, and/or additional elements. By "operably linked" herein is meant that the nucleic acid is placed into a functional relationship with another nucleic acid sequence. Generally, these expression vectors include transcriptional and translational regulatory nucleic acid operably linked to the nucleic acid encoding the anti-CD30 antibody, and are typically appropriate to the host cell used to express the protein. In general, the transcriptional and translational regulatory sequences may include promoter sequences, ribosomal binding sites, transcriptional start and stop sequences, translational start and stop sequences, and enhancer or activator sequences. As is also known in the art, expression vectors typically contain a selection gene or marker to allow the selection of transformed host cells containing the expression vector. Selection genes are well known in the art and will vary with the host cell used.

CD30 targeting proteins may be operably linked to a fusion partner to enable targeting of the expressed protein, purification, screening, display, and the like. Fusion partners may be linked to the anti-CD30 antibody sequence via a linker sequences. The linker sequence will generally comprise a small number of amino acids, typically less than ten, although longer linkers may also be used. Typically, linker sequences are selected to be flexible and resistant to degradation. As will be appreciated by those skilled in the art, any of a wide variety of sequences may be used as linkers. For example, a common linker sequence comprises the amino acid sequence GGGGS. A fusion partner may be a targeting or signal sequence that directs anti-CD30 antibody and any associated fusion partners to a desired cellular location or to the extracellular media. As is known in the art, certain signaling sequences may target a protein to be either secreted into the growth media, or into the periplasmic space, located between the inner and outer membrane of the cell. A fusion partner may also be a sequence that encodes a peptide or protein that enables purification and/or screening. Such fusion partners include but are not limited to polyhistidine tags (His-tags) (for example $H_6$ and $H_{10}$ or other tags for use with Immobilized Metal Affinity Chromatography (IMAC) systems (e.g. $Ni^{+2}$ affinity columns)), GST fusions, MBP fusions, Strep-tag, the BSP biotinylation target sequence of the bacterial enzyme BirA, and epitope tags which are targeted by antibodies (for example c-myc tags, flag-tags, and the like). As will be appreciated by those skilled in the art, such tags may be useful for purification, for screening, or both. For example, an anti-CD30 antibody may be purified using a His-tag by immobilizing it to a $Ni^{+2}$ affinity column, and then after purification the same His-tag may be used to immobilize the antibody to a $Ni^{+2}$ coated plate to perform an ELISA or other binding assay (as described below). A fusion partner may enable the use of a selection method to screen anti-CD30 antibodies (see below). Fusion partners that enable a variety of selection methods are well-known in the art, and all of these find use in the present invention. For example, by fusing the members of an anti-CD30 antibody library to the gene III protein, phage display can be employed (Kay et al., Phage display of peptides and proteins: a laboratory manual, Academic Press, San Diego, Calif., 1996; Lowman et al., 1991, *Biochemistry* 30:10832-10838; Smith, 1985, *Science* 228:1315-1317, entirely incorporated by reference). Fusion partners may enable anti-CD30 antibodies to be labeled. Alternatively, a fusion partner may bind to a specific sequence on the expression vector, enabling the fusion partner and associated anti-CD30 antibody to be linked covalently or noncovalently with the nucleic acid that encodes them. For example, U.S. Ser. Nos. 09/642,574; 10/080,376; 09/792,630; 10/023,208; 09/792,626; 10/082,671; 09/953,351; 10/097,100; U.S. Ser. No. 60/366,658; PCT WO 00/22906; PCT WO 01/49058; PCT WO 02/04852; PCT WO 02/04853; PCT WO 02/08023; PCT WO 01/28702; and PCT WO 02/07466, each of which is incorporated by reference in its entirety, describe such a fusion partner and technique that may find use in the present invention.

The methods of introducing exogenous nucleic acid into host cells are well known in the art, and will vary with the host cell used. Techniques include but are not limited to dextran-mediated transfection, calcium phosphate precipitation, calcium chloride treatment, polybrene mediated transfection, protoplast fusion, electroporation, viral or phage infection, encapsulation of the polynucleotide(s) in liposomes, and direct microinjection of the DNA into nuclei. In the case of mammalian cells, transfection may be either transient or stable.

In a preferred embodiment, anti-CD30 antibodies are purified or isolated after expression. Proteins may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. As is well known in the art, a variety of natural proteins bind Fc and antibodies, and these proteins can find use in the present invention for purification of anti-CD30 antibodies. For example, the bacterial proteins A and G bind to the Fc region. Likewise, the bacterial protein L binds to the Fab region of some antibodies, as of course does the antibody's target antigen. Purification can often be enabled by a particular fusion partner. For example, anti-CD30 antibodies may be purified using glutathione resin if a GST fusion is employed, $Ni^{+2}$ affinity chromatography if a His-tag is employed, or immobilized anti-flag antibody if a flag-tag is used. For general guidance in suitable purification techniques, see, e.g. entirely incorporated by reference Protein Purification: Principles and Practice, $3^{rd}$ Ed., Scopes, Springer-Verlag, NY, 1994, entirely incorporated by reference. The degree of purification necessary will vary depending on the screen or use of the anti-CD30 antibodies. In some instances no purification is necessary. For example in one embodiment, if the anti-CD30 antibodies are secreted, screening may take place directly from the media. As is well known in the art, some methods of selection do not involve purification of proteins. Thus, for example, if a library of anti-CD30 antibodies is made into a phage display library, protein purification may not be performed.

Experimental Testing of Anti-CD30 Antibodies

Assays

CD30 targeting proteins may be screened using a variety of methods, including but not limited to those that use in vitro assays, in vivo and cell-based assays, and selection technologies. Automation and high-throughput screening technologies may be utilized in the screening procedures. Screening may employ the use of a fusion partner or label. The use of fusion partners has been discussed above. By "labeled" herein is meant that the anti-CD30 antibodies of the invention have one or more elements, isotopes, or chemical compounds attached to enable the detection in a screen. In general, labels fall into three classes: a) immune labels, which may be an epitope incorporated as a fusion partner that is recognized by an antibody, b) isotopic labels, which may be radioactive or heavy isotopes, and c) small molecule labels, which may include fluorescent and colorimetric dyes, or molecules such as biotin that enable other labeling methods. Labels may be incorporated into the compound at any position and may be incorporated in vitro or in vivo during protein expression.

In a preferred embodiment, the functional and/or biophysical properties of anti-CD30 antibodies are screened in an in vitro assay. In vitro assays may allow a broad dynamic range for screening properties of interest. Properties of anti-CD30 antibodies that may be screened include but are not limited to stability, solubility, and affinity for Fc ligands, for example FcγRs. Multiple properties may be screened simultaneously or individually. Proteins may be purified or unpurified, depending on the requirements of the assay. In one embodiment, the screen is a qualitative or quantitative binding assay for binding of anti-CD30 antibodies to a protein or nonprotein molecule that is known or thought to bind the anti-CD30 antibody. In a preferred embodiment, the screen is a binding assay for measuring binding to the CD30 target antigen. In an alternately preferred embodiment, the screen is an assay for binding of anti-CD30 antibodies to an Fc ligand, including but are not limited to the family of FcγRs, the neonatal receptor FcRn, the complement protein C1q, and the bacterial proteins A and G. Said Fc ligands may be from any organism, with humans, mice, rats, rabbits, and monkeys preferred. Binding assays can be carried out using a variety of methods known in the art, including but not limited to FRET (Fluorescence Resonance Energy Transfer) and BRET (Bioluminescence Resonance Energy Transfer)-based assays, AlphaScreen™ (Amplified Luminescent Proximity Homogeneous Assay), Scintillation Proximity Assay, ELISA (Enzyme-Linked Immunosorbent Assay), SPR (Surface Plasmon Resonance, also known as BIACORE®), isothermal titration calorimetry, differential scanning calorimetry, gel electrophoresis, and chromatography including gel filtration. These and other methods may take advantage of some fusion partner or label of the anti-CD30 antibody. Assays may employ a variety of detection methods including but not limited to chromogenic, fluorescent, luminescent, or isotopic labels.

The biophysical properties of anti-CD30 antibodies, for example stability and solubility, may be screened using a variety of methods known in the art. Protein stability may be determined by measuring the thermodynamic equilibrium between folded and unfolded states. For example, anti-CD30 antibodies of the present invention may be unfolded using chemical denaturant, heat, or pH, and this transition may be monitored using methods including but not limited to circular dichroism spectroscopy, fluorescence spectroscopy, absorbance spectroscopy, NMR spectroscopy, calorimetry, and proteolysis. As will be appreciated by those skilled in the art, the kinetic parameters of the folding and unfolding transitions may also be monitored using these and other techniques. The solubility and overall structural integrity of an anti-CD30 antibody may be quantitatively or qualitatively determined using a wide range of methods that are known in the art. Methods which may find use in the present invention for characterizing the biophysical properties of anti-CD30 antibodies include gel electrophoresis, isoelectric focusing, capillary electrophoresis, chromatography such as size exclusion chromatography, ion-exchange chromatography, and reversed-phase high performance liquid chromatography, peptide mapping, oligosaccharide mapping, mass spectrometry, ultraviolet absorbance spectroscopy, fluorescence spectroscopy, circular dichroism spectroscopy, isothermal titration calorimetry, differential scanning calorimetry, analytical ultra-centrifugation, dynamic light scattering, proteolysis, and cross-linking, turbidity measurement, filter retardation assays, immunological assays, fluorescent dye binding assays, protein-staining assays, microscopy, and detection of aggregates via ELISA or other binding assay. Structural analysis employing X-ray crystallographic techniques and NMR spectroscopy may also find use. In one embodiment, stability and/or solubility may be measured by determining the amount of protein solution after some defined period of time. In this assay, the protein may or may not be exposed to some extreme condition, for example elevated temperature, low pH, or the presence of denaturant. Because function typically requires a stable, soluble, and/or well-folded/structured protein, the aforementioned functional and binding assays also provide ways to perform such a measurement. For example, a solution comprising an anti-CD30 antibody could be assayed for its ability to bind target antigen, then exposed to elevated temperature for one or more defined periods of time, then assayed for antigen binding again. Because unfolded and aggregated protein is not expected to be capable of binding antigen, the amount of activity remaining provides a measure of the anti-CD30 antibody's stability and solubility.

In a preferred embodiment, the library is screened using one or more cell-based or in vitro assays. For such assays, anti-CD30 antibodies, purified or unpurified, are typically added exogenously such that cells are exposed to individual variants or groups of variants belonging to a library. These assays are typically, but not always, based on the biology of the ability of the anti-CD30 antibody to bind to CD30 and mediate some biochemical event, for example effector functions like cellular lysis, phagocytosis, ligand/receptor binding inhibition, inhibition of growth and/or proliferation, apoptosis and the like. Such assays often involve monitoring the response of cells to anti-CD30 antibody, for example cell survival, cell death, cellular phagocytosis, cell lysis, change in cellular morphology, or transcriptional activation such as cellular expression of a natural gene or reporter gene. For example, such assays may measure the ability of anti-CD30 antibodies to elicit ADCC, ADCP, or CDC. For some assays additional cells or components, that is in addition to the target cells, may need to be added, for example serum complement, or effector cells such as peripheral blood monocytes (PBMCs), NK cells, macrophages, and the like. Such additional cells may be from any organism, preferably humans, mice, rat, rabbit, and monkey. Crosslinked or monomeric antibodies may cause apoptosis of certain cell lines expressing the antibody's target antigen, or they may mediate attack on target cells by immune cells which have been added to the assay. Methods for monitoring cell death or viability are known in the art, and include the use of dyes, fluorophores, immunochemical, cytochemical, and radioactive reagents. For example, caspase assays or annexin-flourconjugates may enable apoptosis to be measured, and uptake or release of radioactive substrates (e.g. Chromium-51 release assays) or the metabolic reduction of fluorescent dyes such as alamar blue may enable cell growth, proliferation or activation to be monitored. In a preferred embodiment, the DELFIA® EuTDA-based cytotoxicity assay (Perkin Elmer, Mass.) is used. Alternatively, dead or damaged target cells may be monitored by measuring the release of one or more natural intracellular proteins, for example lactate dehydrogenase. Transcriptional activation may also serve as a method for assaying function in cell-based assays. In this case, response may be monitored by assaying for natural genes or proteins which may be upregulated or down-regulated, for example the release of certain interleukins may be measured, or alternatively readout may be via a luciferase or GFP-reporter construct. Cell-based assays may also involve the measure of morphological changes of cells as a response to the presence of an anti-CD30 antibody. Cell types for such assays may be prokaryotic or eukaryotic, and a variety of cell lines that are known in the art may be employed. Alternatively, cell-based screens are performed using cells that have been transformed or transfected with nucleic acids encoding the anti-CD30 antibodies.

In vitro assays include but are not limited to binding assays, ADCC, CDC, cytotoxicity, proliferation, peroxide/ozone release, chemotaxis of effector cells, inhibition of such assays by reduced effector function antibodies; ranges of activities such as >100× improvement or >100× reduction, blends of receptor activation and the assay outcomes that are expected from such receptor profiles.

Animal Models

The biological properties of the anti-CD30 antibodies of the present invention may be characterized in cell, tissue, and whole organism experiments. As is know in the art, drugs are often tested in animals, including but not limited to mice, rats, rabbits, dogs, cats, pigs, and monkeys, in order to measure a drug's efficacy for treatment against a disease or disease model, or to measure a drug's pharmacokinetics, toxicity, and other properties. Said animals may be referred to as disease models. With respect to the anti-CD30 antibodies of the present invention, a particular challenge arises when using animal models to evaluate the potential for in-human efficacy of candidate polypeptides—this is due, at least in part, to the fact that anti-CD30 antibodies that have a specific effect on the affinity for a human Fc receptor may not have a similar affinity effect with the orthologous animal receptor. These problems can be further exacerbated by the inevitable ambiguities associated with correct assignment of true orthologues (Mechetina et al., *Immunogenetics*, 2002 54:463-468, entirely incorporated by reference), and the fact that some orthologues simply do not exist in the animal (e.g. humans possess an FcγRIIa whereas mice do not). Therapeutics are often tested in mice, including but not limited to nude mice, SCID mice, xenograft mice, and transgenic mice (including knockins and knockouts). For example, an anti-CD30 antibody of the present invention that is intended as an anti-cancer therapeutic may be tested in a mouse cancer model, for example a xenograft mouse. In this method, a tumor or tumor cell line is grafted onto or injected into a mouse, and subsequently the mouse is treated with the therapeutic to determine the ability of the anti-CD30 antibody to reduce or inhibit cancer growth and metastasis. An alternative approach is the use of a SCID murine model in which immune-deficient mice are injected with human PBLs, conferring a semi-functional and human immune system—with an appropriate array of human FcRs— to the mice that have subsequently been injected with antibodies or Fc-polypeptides that target injected human tumor cells. In such a model, the Fc-polypeptides that target the desired antigen (such as her2/neu on SkOV3 ovarian cancer cells) interact with human PBLs within the mice to engage tumoricidal effector functions. Such experimentation may provide meaningful data for determination of the potential of said anti-CD30 antibody to be used as a therapeutic. Any organism, preferably mammals, may be used for testing. For example because of their genetic similarity to humans, monkeys can be suitable therapeutic models, and thus may be used to test the efficacy, toxicity, pharmacokinetics, or other property of the anti-CD30 antibodies of the present invention. Tests of the anti-CD30 antibodies of the present invention in humans are ultimately required for approval as drugs, and thus of course these experiments are contemplated. Thus the anti-CD30 antibodies of the present invention may be tested in humans to determine their therapeutic efficacy, toxicity, pharmacokinetics, and/or other clinical properties.

The anti-CD30 antibodies of the present invention may confer superior performance on Fc-containing therapeutics in animal models or in humans. The receptor binding profiles of such anti-CD30 antibodies, as described in this specification, may, for example, be selected to increase the potency of cytotoxic drugs or to target specific effector functions or effector cells to improve the selectivity of the drug's action. Further, receptor binding profiles can be selected that may reduce some or all effector functions thereby reducing the side-effects or toxicity of such Fc-containing drug. For example, an anti-CD30 antibody with reduced binding to FcγRIIIa, FcγRI and FcγRIIa can be selected to eliminate most cell-mediated effector function, or an anti-CD30 antibody with reduced binding to C1q may be selected to limit complement-mediated effector functions. In some contexts, such effector functions are known to have potential toxic effects, therefore eliminating them may increase the safety of the Fc-bearing drug and such improved safety may be characterized in animal models. In some contexts, such effector functions are known to mediate the desirable therapeutic activity, therefore enhancing them may increase the activity or potency of the Fc-bearing drug and such improved activity or potency may be characterized in animal models.

Optimized anti-CD30 antibodies can be tested in a variety of orthotopic tumor models. These clinically relevant animal models are important in the study of pathophysiology and therapy of aggressive cancers like pancreatic, prostate and breast cancer. Immune deprived mice including, but not limited to athymic nude or SCID mice are frequently used in scoring of local and systemic tumor spread from the site of intraorgan (e.g. pancreas, prostate or mammary gland) injection of human tumor cells or fragments of donor patients.

In preferred embodiments, anti-CD30 antibodies of the present invention may be assessed for efficacy in clinically relevant animal models of various human diseases. In many cases, relevant models include various transgenic animals for specific tumor antigens.

Relevant transgenic models such as those that express human Fc receptors (e.g., CD16 including the gamma chain, FcγR1, RIIa/b, and others) could be used to evaluate and test anti-CD30 antibody antibodies and Fc-fusions in their efficacy. The evaluation of anti-CD30 antibodies by the introduction of human genes that directly or indirectly mediate effector function in mice or other rodents that may enable physiological studies of efficacy in tumor toxicity or other diseases such as autoimmune disorders and RA. Human Fc receptors such as FcγRIIIa may possess polymorphisms such as that in position 158 V or F which would further enable the introduction of specific and combinations of human polymorphisms into rodents. The various studies involving polymorphism-specific FcRs is not limited to this section, however encompasses all discussions and applications of FcRs in general as specified in throughout this application. anti-CD30 antibodies of the present invention may confer superior activity on Fc-containing drugs in such transgenic models, in particular variants with binding profiles optimized for human FcγRIIIa mediated activity may show superior activity in transgenic CD16 mice. Similar improvements in efficacy in mice transgenic for the other human Fc receptors, e.g. FcγRIIa, FcγRI, etc., may be observed for anti-CD30 antibodies with binding profiles optimized for the respective receptors. Mice transgenic for multiple human receptors would show improved activity for anti-CD30 antibodies with binding profiles optimized for the corresponding multiple receptors, for example as outlined in Table 1.

Because of the difficulties and ambiguities associated with using animal models to characterize the potential efficacy of candidate therapeutic antibodies in a human patient, some variant polypeptides of the present invention may find utility as proxies for assessing potential in-human efficacy. Such proxy molecules would preferably mimic—in the animal system—the FcR and/or complement biology of a corresponding candidate human anti-CD30 antibody. This mimicry is most likely to be manifested by relative association affinities between specific anti-CD30 antibodies and animal vs. human receptors. For example, if one were using a mouse model to assess the potential in-human efficacy of an anti-CD30 antibody that has enhanced affinity for human FcγRIIIa, an appropriate proxy variant would have enhanced affinity for mouse FcγRIII-2 (mouse CD16-2). Alternatively if one were using a mouse model to assess the potential in-human efficacy of an anti-CD30 antibody that has reduced affinity for the inhibitory human FcγRIIb, an appropriate proxy variant would have reduced affinity for mouse FcγRII. It should also be noted that the proxy anti-CD30 antibodies could be created in the context of a human anti-CD30 antibody, an animal anti-CD30 antibody, or both.

In a preferred embodiment, the testing of anti-CD30 antibodies may include study of efficacy in primates (e.g. cynomolgus monkey model) to facilitate the evaluation of depletion of specific target cells harboring CD30 antigen. Additional primate models include but not limited to that of the rhesus monkey and Fc polypeptides in therapeutic studies of autoimmune, transplantation and cancer.

Toxicity studies are performed to determine the antibody or Fc-fusion related-effects that cannot be evaluated in standard pharmacology profile or occur only after repeated administration of the agent. Most toxicity tests are performed in two species—a rodent and a non-rodent—to ensure that any unexpected adverse effects are not overlooked before new therapeutic entities are introduced into man. In general, these models may measure a variety of toxicities including genotoxicity, chronic toxicity, immunogenicity, reproductive/developmental toxicity and carcinogenicity. Included within the aforementioned parameters are standard measurement of food consumption, bodyweight, antibody formation, clinical chemistry, and macro- and microscopic examination of standard organs/tissues (e.g. cardiotoxicity). Additional parameters of measurement are injection site trauma and the measurement of neutralizing antibodies, if any. Traditionally, monoclonal antibody therapeutics, naked or conjugated are evaluated for cross-reactivity with normal tissues, immunogenicity/antibody production, conjugate or linker toxicity and "bystander" toxicity of radiolabeled species. Nonetheless, such studies may have to be individualized to address specific concerns and following the guidance set by ICH S6 (Safety studies for biotechnological products also noted above). As such, the general principles are that the products are sufficiently well characterized and for which impurities/contaminants have been removed, that the test material is comparable throughout development, and GLP compliance.

The pharmacokinetics (PK) of the anti-CD30 antibodies of the invention can be studied in a variety of animal systems, with the most relevant being non-human primates such as the cynomolgus, rhesus monkeys. Single or repeated i.v./s.c. administrations over a dose range of 6000-fold (0.05-300 mg/kg) can be evaluated for the half-life (days to weeks) using plasma concentration and clearance as well as volume of distribution at a steady state and level of systemic absorbance can be measured. Examples of such parameters of measurement generally include maximum observed plasma concentration ($C_{max}$), the time to reach $C_{max}$($T_{max}$), the area under the plasma concentration-time curve from time 0 to infinity [AUC(0-inf] and apparent elimination half-life (T1/2). Additional measured parameters could include compartmental analysis of concentration-time data obtained following i.v. administration and bioavailability. Examples of pharmacological/toxicological studies using cynomolgus have been established for Rituxan and Zevalin in which monoclonal antibodies to CD20 are cross-reactive. Biodistribution, dosimetry (for radiolabled antibodies), and PK studies can also be done in rodent models. Such studies would evaluate tolerance at all doses administered, toxicity to local tissues, preferential localization to rodent xenograft animal models, depletion of target cells (e.g. CD20 positive cells).

The anti-CD30 antibodies of the present invention may confer superior pharmacokinetics on Fc-containing therapeutics in animal systems or in humans. For example, increased binding to FcRn may increase the half-life and exposure of the Fc-containing drug. Alternatively, decreased binding to FcRn may decrease the half-life and exposure of the Fc-containing drug in cases where reduced exposure is favorable such as when such drug has side-effects.

It is known in the art that the array of Fc receptors is differentially expressed on various immune cell types, as well as in different tissues. Differential tissue distribution of Fc receptors may ultimately have an impact on the pharmacodynamic (PD) and pharmacokinetic (PK) properties of anti-CD30 antibodies of the present invention. Because anti-CD30 antibodies of the presentation have varying affinities for the array of Fc receptors, further screening of the polypeptides for PD and/or PK properties may be extremely useful for defining the optimal balance of PD, PK, and therapeutic efficacy conferred by each candidate polypeptide.

Pharmacodynamic studies may include, but are not limited to, targeting specific tumor cells or blocking signaling mechanisms, measuring depletion of target antigen expressing cells or signals, etc. The anti-CD30 antibodies of the present invention may target particular effector cell populations and thereby direct Fc-containing drugs to recruit certain activities to improve potency or to increase penetration into a particularly favorable physiological compartment. For example, neutrophil activity and localization can be targeted by an anti-CD30 antibody that preferentially targets FcγRIIIb. Such pharmacodynamic effects may be demonstrated in animal models or in humans.

Clinical Use of Anti-CD30 Antibodies

The anti-CD30 antibodies of the present invention may be used for various therapeutic purposes. As will be appreciated by those in the art, the anti-CD30 antibodies of the present invention may be used for any therapeutic purpose that antibodies, and the like may be used for. In a preferred embodiment, the anti-CD30 antibodies are administered to a patient to treat disorders including but not limited to autoimmune and inflammatory diseases, infectious diseases, and cancer.

A "patient" for the purposes of the present invention includes both humans and other animals, preferably mammals and most preferably humans. Thus the anti-CD30 antibodies of the present invention have both human therapy and veterinary applications. The term "treatment" or "treating" in the present invention is meant to include therapeutic treatment, as well as prophylactic, or suppressive measures for a disease or disorder. Thus, for example, successful administration of an anti-CD30 antibody prior to onset of the disease results in treatment of the disease. As another example, successful administration of an optimized anti-CD30 antibody after clinical manifestation of the disease to combat the symptoms of the disease comprises treatment of the disease. "Treatment" and "treating" also encompasses administration of an optimized anti-CD30 antibody after the appearance of the disease in order to eradicate the disease. Successful administration of an agent after onset and after clinical symptoms have developed, with possible abatement of clinical symptoms and perhaps amelioration of the disease, comprises treatment of the disease. Those "in need of treatment" include mammals already having the disease or disorder, as well as those prone to having the disease or disorder, including those in which the disease or disorder is to be prevented.

Indications

In one embodiment, an anti-CD30 antibody of the present invention is administered to a patient having a disease involving inappropriate expression of a protein or other molecule. Within the scope of the present invention this is meant to include diseases and disorders characterized by aberrant proteins, due for example to alterations in the amount of a protein present, protein localization, posttranslational modification, conformational state, the presence of a mutant or pathogen protein, etc. Similarly, the disease or disorder may be characterized by alterations molecules including but not limited to polysaccharides and gangliosides. An overabundance may be due to any cause, including but not limited to overexpression at the molecular level, prolonged or accumulated appearance at the site of action, or increased activity of a protein relative to normal. Included within this definition are diseases and disorders characterized by a reduction of a protein. This reduction may be due to any cause, including but not limited to reduced expression at the molecular level, shortened or reduced appearance at the site of action, mutant forms of a protein, or decreased activity of a protein relative to normal. Such an overabundance or reduction of a protein can be measured relative to normal expression, appearance, or activity of a protein, and said measurement may play an important role in the development and/or clinical testing of the anti-CD30 antibodies of the present invention.

By "cancer" and "cancerous" herein refer to or describe the physiological condition in mammals that is typically characterized by unregulated cell growth. Examples of cancer include but are not limited to carcinoma, lymphoma, blastoma, sarcoma (including liposarcoma), neuroendocrine tumors, mesothelioma, schwanoma, meningioma, adenocarcinoma, melanoma, and leukemia or lymphoid malignancies.

More particular examples of such cancers include hematologic malignancies, such as Hodgkin's lymphoma; non-Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplasmacytic leukemia), tumors of lymphocyte precursor cells, including B-cell acute lymphoblastic leukemia/lymphoma, and T-cell acute lymphoblastic leukemia/lymphoma, thymoma, tumors of the mature T and NK cells, including peripheral T-cell leukemias, adult T-cell leukemia/T-cell lymphomas and large granular lymphocytic leukemia, Langerhans cell histocytosis, myeloid neoplasias such as acute myelogenous leukemias, including AML with maturation, AML without differentiation, acute promyelocytic leukemia, acute myelomonocytic leukemia, and acute monocytic leukemias, myelodysplastic syndromes, and chronic myeloproliferative disorders, including chronic myelogenous leukemia; tumors of the central nervous system such as glioma, glioblastoma, neuroblastoma, astrocytoma, medulloblastoma, ependymoma, and retinoblastoma; solid tumors of the head and neck (eg. nasopharyngeal cancer, salivary gland carcinoma, and esophagael cancer), lung (eg. small-cell lung cancer, non-small cell lung cancer, adenocarcinoma of the lung and squamous carcinoma of the lung), digestive system (eg. gastric or stomach cancer including gastrointestinal cancer, cancer of the bile duct or biliary tract, colon cancer, rectal cancer, colorectal cancer, and anal carcinoma), reproductive system (eg. testicular, penile, or prostate cancer, uterine, vaginal, vulval, cervical, ovarian, and endometrial cancer), skin (eg. melanoma, basal cell carcinoma, squamous cell cancer, actinic keratosis), liver (eg. liver cancer, hepatic carcinoma, hepatocellular cancer, and hepatoma), bone (eg. osteoclastoma, and osteolytic bone cancers) additional tissues and organs (eg. pancreatic cancer, bladder cancer, kidney or renal cancer, thyroid cancer, breast cancer, cancer of the peritoneum, and Kaposi's sarcoma), and tumors of the vascular system (eg. angiosarcoma and hemagiopericytoma).

By "autoimmune diseases" herein include allogenic islet graft rejection, alopecia greata, ankylosing spondylitis, antiphospholipid syndrome, autoimmune Addison's disease, antineutrophil cytoplasmic autoantibodies (ANCA), autoimmune diseases of the adrenal gland, autoimmune hemolytic anemia, autoimmune hepatitis, autoimmune myocarditis, autoimmune neutropenia, autoimmune oophoritis and orchitis, autoimmune thrombocytopenia, autoimmune urticaria, Behcet's disease, bullous pemphigoid, cardiomyopathy, Castleman's syndrome, celiac spruce-dermatitis, chronic fatigue immune disf unction syndrome, chronic inflammatory demyelinating polyneuropathy, Churg-Strauss syndrome, cicatrical pemphigoid, CREST syndrome, cold agglutinin disease, Crohn's disease, dermatomyositis, discoid lupus, essential mixed cryoglobulinemia, factor VIII deficiency, fibromyalgia-fibromyositis, glomerulonephritis, Grave's disease, Guillain-Barre, Goodpasture's syndrome, graft-versus-host disease (GVHD), Hashimoto's thyroiditis, hemophilia A, idiopathic pulmonary fibrosis, idiopathic thrombocytopenia purpura (ITP), IgA neuropathy, IgM polyneuropathies, immune mediated thrombocytopenia, juvenile arthritis, Kawasaki's disease, lichen plantus, lupus erthematosis, Meniere's disease, mixed connective tissue disease, multiple sclerosis, type 1 diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobinulinemia, primary biliary cirrhosis, psoriasis, psoriatic arthritis, Reynauld's phenomenon, Reiter's syndrome, rheumatoid arthritis, sarcoidosis, scleroderma, Sjorgen's syndrome, solid organ transplant rejection, stiff-man syndrome, systemic lupus erythematosus, takayasu arteritis, temporal arteristis/giant cell arteritis, thrombotic thrombocytopenia purpura, ulcerative colitis, uveitis, vasculitides such as dermatitis herpetiformis vasculitis, vitiligo, and Wegner's granulomatosis.

By "inflammatory disorders" herein include acute respiratory distress syndrome (ARDS), acute septic arthritis, adjuvant arthritis (Prakken et al., Springer Semin Immunopathol., 2003 August; 25(1):47-63, entirely incorporated by reference), juvenile idiopathic arthritis (de Kleer et al., Arthritis Rheum. 2003 July; 47(7):2001-10, entirely incorporated by reference), allergic encephalomyelitis, allergic rhinitis, allergic vasculitis, allergy, asthma, atherosclerosis, chronic inflammation due to chronic bacterial or viral infectionis, chronic obstructive pulmonary disease (COPD), coronary artery disease, encephalitis, inflammatory bowel disease, inflammatory osteolysis, inflammation associated with acute and delayed hypersensitivity reactions, inflammation associated with tumors, peripheral nerve injury or demyelinating diseases, inflammation associated with tissue trauma such as burns and ischemia, inflammation due to meningitis, multiple organ injury syndrome, pulmonary fibrosis, sepsis and septic shock, Stevens-Johnson syndrome, undifferentiated arthropy, and undifferentiated spondyloarthropathy.

By "infectious diseases" herein include diseases caused by pathogens such as viruses, bacteria, fungi, protozoa, and parasites. Infectious diseases may be caused by viruses including adenovirus, cytomegalovirus, dengue, Epstein-Barr, hanta, hepatitis A, hepatitis B, hepatitis C, herpes simplex type I, herpes simplex type II, human immunodeficiency virus, (HIV), human papilloma virus (HPV), influenza, measles, mumps, papova virus, polio, respiratory syncytial virus, rinderpest, rhinovirus, rotavirus, rubella, SARS virus, smallpox, viral meningitis, and the like. Infections diseases may also be caused by bacteria including *Bacillus antracis, Borrelia burgdorferi, Campylobacter jejuni, Chlamydia trachomatis, Clostridium botulinum, Clostridium tetani, Diptheria, E. coli, Legionella, Helicobacter pylori, Mycobacterium rickettsia, Mycoplasma nesisseria, Pertussis, Pseudomonas aeruginosa, S. pneumonia, Streptococcus, Staphylococcus, Vibria cholerae, Yersinia pestis*, and the like. Infectious diseases may also be caused by fungi such as *Aspergillus fumigatus, Blastomyces dermatitidis, Candida albicans, Coccidioides immitis, Cryptococcus neoformans, Histoplasma capsulatum, Penicillium marneffei*, and the like. Infectious diseases may also be caused by protozoa and parasites such as chlamydia, kokzidioa, leishmania, malaria, rickettsia, trypanosoma, and the like.

Furthermore, antibodies of the present invention may be used to prevent or treat additional conditions including but not limited to heart conditions such as congestive heart failure (CHF), myocarditis and other conditions of the myocardium; skin conditions such as rosecea, acne, and eczema; bone and tooth conditions such as bone loss, osteoporosis, Paget's disease, Langerhans' cell histiocytosis, periodontal disease, disuse osteopenia, osteomalacia, monostotic fibrous dysplasia, polyostotic fibrous dysplasia, bone metastasis, bone pain management, humoral malignant hypercalcemia, periodontal reconstruction, spinal cord injury, and bone fractures; metabolic conditions such as Gaucher's disease; endocrine conditions such as Cushing's syndrome; and neurological conditions.

Formulation

Pharmaceutical compositions are contemplated wherein an anti-CD30 antibody of the present invention and one or more therapeutically active agents are formulated. Formulations of the anti-CD30 antibodies of the present invention are prepared for storage by mixing said anti-CD30 antibody having the desired degree of purity with optional pharmaceutically acceptable carriers, excipients or stabilizers (Remington's Pharmaceutical Sciences 16th edition, Osol, A. Ed., 1980), in the form of lyophilized formulations or aqueous solutions. Acceptable carriers, excipients, or stabilizers are nontoxic to recipients at the dosages and concentrations employed, and include buffers such as phosphate, citrate, acetate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl orbenzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; sweeteners and other flavoring agents; fillers such as microcrystalline cellulose, lactose, corn and other starches; binding agents; additives; coloring agents; salt-forming counter-ions such as sodium; metal complexes (e.g. Zn-protein complexes); and/or non-ionic surfactants such as TWEEN™, PLURONICS™ or polyethylene glycol (PEG). In a preferred embodiment, the pharmaceutical composition that comprises the anti-CD30 antibody of the present invention may be in a water-soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethane-sulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The formulations to be used for in vivo administration are preferably sterile. This is readily accomplished by filtration through sterile filtration membranes or other methods.

The anti-CD30 antibodies disclosed herein may also be formulated as immunoliposomes. A liposome is a small vesicle comprising various types of lipids, phospholipids and/or surfactant that is useful for delivery of a therapeutic agent to a mammal. Liposomes containing the anti-CD30 antibody are prepared by methods known in the art, such as described in Epstein et al., 1985, *Proc Natl Acad Sci USA*, 82:3688; Hwang et al., 1980, *Proc Natl Acad Sci USA*, 77:4030; U.S. Pat. Nos. 4,485,045; 4,544,545; and PCT WO 97/38731, each of which is incorporated by reference in its entirety. Liposomes with enhanced circulation time are disclosed in U.S. Pat. No. 5,013,556. The components of the liposome are commonly arranged in a bilayer formation, similar to the lipid arrangement of biological membranes. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. A chemotherapeutic agent or other therapeutically active agent is optionally contained within the liposome (Gabizon et al., 1989, *J National Cancer Inst* 81:1484, entirely incorporated by reference).

The anti-CD30 antibody and other therapeutically active agents may also be entrapped in microcapsules prepared by methods including but not limited to coacervation techniques, interfacial polymerization (for example using hydroxymethylcellulose or gelatin-microcapsules, or poly-(methylmethacylate) microcapsules), colloidal drug delivery systems (for example, liposomes, albumin microspheres, microemulsions, nano-particles and nanocapsules), and macroemulsions. Such techniques are disclosed in Remington's Pharmaceutical Sciences 16th edition, Osol, A. Ed., 1980, entirely incorporated by reference. Sustained-release preparations may be prepared. Suitable examples of sustained-release preparations include semipermeable matrices of solid hydrophobic polymer, which matrices are in the form of shaped articles, e.g. films, or microcapsules. Examples of sustained-release matrices include polyesters, hydrogels (for example poly(2-hydroxyethyl-methacrylate), or poly(vinylalcohol)), polylactides (U.S. Pat. No. 3,773, 919, entirely incorporated by reference), copolymers of L-glutamic acid and gamma ethyl-L-glutamate, non-degradable ethylene-vinyl acetate, degradable lactic acid-glycolic acid copolymers such as the Lupron Depot® (which are injectable microspheres composed of lactic acid-glycolic acid copolymer and leuprolide acetate), poly-D-(–)-3-hydroxybutyric acid, and ProLease® (commercially available from Alkermes), which is a microsphere-based delivery system composed of the desired bioactive molecule incorporated into a matrix of poly-DL-lactide-co-glycolide (PLG).

Administration

Administration of the pharmaceutical composition comprising an anti-CD30 antibody of the present invention, preferably in the form of a sterile aqueous solution, may be done in a variety of ways, including, but not limited to orally, subcutaneously, intravenously, intranasally, intraotically, transdermally, topically (e.g., gels, salves, lotions, creams, etc.), intraperitoneally, intramuscularly, intrapulmonary, vaginally, parenterally, rectally, or intraocularly. In some instances, for example for the treatment of wounds, inflammation, etc., the anti-CD30 antibody may be directly applied as a solution or spray. As is known in the art, the pharmaceutical composition may be formulated accordingly depending upon the manner of introduction.

Subcutaneous administration may be preferable in some circumstances because the patient may self-administer the pharmaceutical composition. Many protein therapeutics are not sufficiently potent to allow for formulation of a therapeutically effective dose in the maximum acceptable volume for subcutaneous administration. This problem may be addressed in part by the use of protein formulations comprising arginine-HCl, histidine, and polysorbate (see WO 04091658, entirely incorporated by reference). Anti-CD30 antibodies of the present invention may be more amenable to subcutaneous administration due to, for example, increased potency, improved serum half-life, or enhanced solubility.

As is known in the art, protein therapeutics are often delivered by IV infusion or bolus. The anti-CD30 antibodies of the present invention may also be delivered using such methods. For example, administration may venious be by intravenous infusion with 0.9% sodium chloride as an infusion vehicle.

Pulmonary delivery may be accomplished using an inhaler or nebulizer and a formulation comprising an aerosolizing agent. For example, AERx® inhalable technology commercially available from Aradigm, or Inhance™ pulmonary delivery system commercially available from Nektar Therapeutics may be used. anti-CD30 antibodies of the present invention may be more amenable to intrapulmonary delivery. FcRn is present in the lung, and may promote transport from the lung to the bloodstream (e.g. Syntonix WO 04004798, Bitonti et. al. (2004) Proc. Nat. Acad. Sci. 101:9763-8, both entirely incorporated by reference). Accordingly, anti-CD30 antibodies that bind FcRn more effectively in the lung or that are released more efficiently in the bloodstream may have improved bioavailability following intrapulmonary administration. Anti-CD30 antibodies of the present invention may also be more amenable to intrapulmonary administration due to, for example, improved solubility or altered isoelectric point.

Furthermore, anti-CD30 antibodies of the present invention may be more amenable to oral delivery due to, for example, improved stability at gastric pH and increased resistance to proteolysis. Furthermore, FcRn appears to be expressed in the intestinal epithelia of adults (Dickinson et. al. (1999) J. Clin. Invest. 104:903-11, entirely incorporated by reference), so anti-CD30 antibodies of the present invention with improved FcRn interaction profiles may show enhanced bioavailability following oral administration. FcRn mediated transport of anti-CD30 antibodies may also occur at other mucus membranes such as those in the gastrointestinal, respiratory, and genital tracts (Yoshida et. al. (2004) Immunity 20:769-83, entirely incorporated by reference).

In addition, any of a number of delivery systems are known in the art and may be used to administer the anti-CD30 antibodies of the present invention. Examples include, but are not limited to, encapsulation in liposomes, microparticles, microspheres (eg. PLA/PGA microspheres), and the like. Alternatively, an implant of a porous, non-porous, or gelatinous material, including membranes or fibers, may be used. Sustained release systems may comprise a polymeric material or matrix such as polyesters, hydrogels, poly(vinylalcohol), polylactides, copolymers of L-glutamic acid and ethyl-L-gutamate, ethylene-vinyl acetate, lactic acid-glycolic acid copolymers such as the LUPRON DEPOT®, and poly-D-(−)-3-hydroxyburyric acid. It is also possible to administer a nucleic acid encoding the anti-CD30 antibody of the current invention, for example by retroviral infection, direct injection, or coating with lipids, cell surface receptors, or other transfection agents. In all cases, controlled release systems may be used to release the anti-CD30 antibody at or close to the desired location of action.

Dosing

The dosing amounts and frequencies of administration are, in a preferred embodiment, selected to be therapeutically or prophylactically effective. As is known in the art, adjustments for protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

The concentration of the therapeutically active anti-CD30 antibody in the formulation may vary from about 0.1 to 100 weight %. In a preferred embodiment, the concentration of the anti-CD30 antibody is in the range of 0.003 to 1.0 molar. In order to treat a patient, a therapeutically effective dose of the anti-CD30 antibody of the present invention may be administered. By "therapeutically effective dose" herein is meant a dose that produces the effects for which it is administered. The exact dose will depend on the purpose of the treatment, and will be ascertainable by one skilled in the art using known techniques. Dosages may range from 0.0001 to 100 mg/kg of body weight or greater, for example 0.1, 1, 10, or 50 mg/kg of body weight, with 1 to 10 mg/kg being preferred.

In some embodiments, only a single dose of the anti-CD30 antibody is used. In other embodiments, multiple doses of the anti-CD30 antibody are administered. The elapsed time between administrations may be less than 1 hour, about 1 hour, about 1-2 hours, about 2-3 hours, about 3-4 hours, about 6 hours, about 12 hours, about 24 hours, about 48 hours, about 2-4 days, about 4-6 days, about 1 week, about 2 weeks, or more than 2 weeks.

In other embodiments the anti-CD30 antibodies of the present invention are administered in metronomic dosing regimes, either by continuous infusion or frequent administration without extended rest periods. Such metronomic administration may involve dosing at constant intervals without rest periods. Typically such regimens encompass chronic low-dose or continuous infusion for an extended period of time, for example 1-2 days, 1-2 weeks, 1-2 months, or up to 6 months or more. The use of lower doses may minimize side effects and the need for rest periods.

In certain embodiments the anti-CD30 antibody of the present invention and one or more other prophylactic or therapeutic agents are cyclically administered to the patient. Cycling therapy involves administration of a first agent at one time, a second agent at a second time, optionally additional agents at additional times, optionally a rest period, and then repeating this sequence of administration one or more times. The number of cycles is typically from 2-10. Cycling therapy may reduce the development of resistance to one or more agents, may minimize side effects, or may improve treatment efficacy.

Combination Therapies

The anti-CD30 antibodies of the present invention may be administered concomitantly with one or more other therapeutic regimens or agents. The additional therapeutic regimes or agents may be used to improve the efficacy or safety of the anti-CD30 antibody. Also, the additional therapeutic regimes or agents may be used to treat the same disease or a comorbidity rather than to alter the action of the anti-CD30 antibody. For example, an anti-CD30 antibody of the present invention may be administered to the patient along with chemotherapy, radiation therapy, or both chemotherapy and radiation therapy. The anti-CD30 antibody of the present invention may be administered in combination with one or more other prophylactic or therapeutic agents, including but not limited to cytotoxic agents, chemotherapeutic agents, cytokines, growth inhibitory agents, anti-hormonal agents, kinase inhibitors, anti-angiogenic agents, cardioprotectants, immunostimulatory agents, immunosuppressive agents, agents that promote proliferation of hematological cells, angiogenesis inhibitors, protein tyrosine kinase (PTK) inhibitors, additional anti-CD30 antibodies, FcγRIIb or other Fc receptor inhibitors, or other therapeutic agents.

The terms "in combination with" and "co-administration" are not limited to the administration of said prophylactic or therapeutic agents at exactly the same time. Instead, it is meant that the anti-CD30 antibody of the present invention and the other agent or agents are administered in a sequence and within a time interval such that they may act together to provide a benefit that is increased versus treatment with only either the anti-CD30 antibody of the present invention or the other agent or agents. It is preferred that the anti-CD30 antibody and the other agent or agents act additively, and especially preferred that they act synergistically. Such molecules are suitably present in combination in amounts that are effective for the purpose intended. The skilled medical practitioner can determine empirically, or by considering the pharmacokinetics and modes of action of the agents, the appropriate dose or doses of each therapeutic agent, as well as the appropriate timings and methods of administration.

In one embodiment, the anti-CD30 antibodies of the present invention are administered with one or more additional molecules comprising antibodies or Fc. The anti-CD30 antibodies of the present invention may be co-administered with one or more other antibodies that have efficacy in treating the same disease or an additional comorbidity; for example two antibodies may be administered that recognize two antigens that are overexpressed in a given type of cancer, or two antigens that mediate pathogenesis of an autoimmune or infectious disease.

Examples of anti-cancer antibodies that may be co-administered include, but are not limited to, anti 17-IA cell surface antigen antibodies such as Panorex™ (edrecolomab); anti-4-1 BB antibodies; anti-4Dc antibodies; anti-A33 antibodies such as A33 and CDP-833; anti-α4β1 integrin antibodies such as natalizumab; anti-α4β7 integrin antibodies such as LDP-02; anti-αVβ1 integrin antibodies such as F-200, M-200, and SJ-749; anti-αVβ3 integrin antibodies such as abciximab, CNTO-95, Mab-17E6, and Vitaxin™, anti-complement factor 5 (C5) antibodies such as 5G1.1; anti-CA125 antibodies such as OvaRex® (oregovomab); anti-CD3 antibodies such as Nuvion® (visilizumab) and Rexomab; anti-CD4 antibodies such as IDEC-151, MDX-CD4, OKT4A; anti-CD6 antibodies such as Oncolysin B and Oncolysin CD6; anti-CD7 antibodies such as HB2; anti-CD19 antibodies such as B43, MT-103, and Oncolysin B; anti-CD20 antibodies such as 2H7, 2H7.v16, 2H7.v114, 2H7.v115, Bexxar® (tositumomab), Rituxan® (rituximab), and Zevalin® (Ibritumomab tiuxetan); anti-CD22 antibodies such as Lymphocide™ (epratuzumab); anti-CD23 antibodies such as IDEC-152; anti-CD25 antibodies such as basiliximab and Zenapax® (daclizumab); anti-CD30 antibodies such as AC10, MDX-060, and SGN-30; anti-CD33 antibodies such as Mylotarg® (gemtuzumab ozogamicin), Oncolysin M, and Smart M195; anti-CD38 antibodies; anti-CD40 antibodies such as SGN-40 and toralizumab; anti-CD40L antibodies such as 5c8, Antova™, and IDEC-131; anti-CD44 antibodies such as bivatuzumab; anti-CD46 antibodies; anti-CD52 antibodies such as Campath® (alemtuzumab); anti-CD55 antibodies such as SC-1; anti-CD56 antibodies such as huN901-DM1; anti-CD64 antibodies such as MDX-33; anti-CD66e antibodies such as XR-303; anti-CD74 antibodies such as IMMU-110; anti-CD80 antibodies such as galiximab and IDEC-114; anti-CD89 antibodies such as MDX-214; anti-CD123 antibodies; anti-CD138 antibodies such as B-B4-DM1; anti-CD146 antibodies such as AA-98; anti-CD148 antibodies; anti-CEA antibodies such as cT84.66, labetuzumab, and Pentacea™; anti-CTLA-4 antibodies such as MDX-101; anti-CXCR4 antibodies; anti-EGFR antibodies such as ABX-EGF, Erbitux® (cetuximab), IMC-C225, and Merck Mab 425; anti-EpCAM antibodies such as Crucell's anti-EpCAM, ING-1, and IS-IL-2; anti-ephrin B2/EphB4 antibodies; anti-Her2 antibodies such as Herceptin®, MDX-210; anti-FAP (fibroblast activation protein) antibodies such as sibrotuzumab; anti-ferritin antibodies such as NXT-211; anti-FGF-1 antibodies; anti-FGF-3 antibodies; anti-FGF-8 antibodies; anti-FGFR antibodies, anti-fibrin antibodies; anti-G250 antibodies such as WX-G250 and Rencarex®; anti-GD2 ganglioside antibodies such as EMD-273063 and GD2 ganglioside antibodies such as BEC2, KW-2871, and mitumomab; anti-gpIIb/IIIa antibodies such as ReoPro; anti-heparinase antibodies; anti-Her2/ErbB2 antibodies such as Herceptin® (trastuzumab), MDX-210, and pertuzumab; anti-HLA antibodies such as Oncolym®, Smart 1D10; anti-HM1.24 antibodies; anti-ICAM antibodies such as ICM3; anti-IgA receptor antibodies; anti-IGF-1 antibodies such as CP-751871 and EM-164; anti-IGF-1R antibodies such as IMC-A12; anti-IL-6 antibodies such as CNTO-328 and elsilimomab; anti-IL-15 antibodies such as HuMax™-IL15; anti-KDR antibodies; anti-laminin 5 antibodies; anti-Lewis Y antigen antibodies such as Hu3S193 and IGN-311; anti-MCAM antibodies; anti-Muc1 antibodies such as BravaRex and TriAb; anti-NCAM antibodies such as ERIC-1 and ICRT; anti-PEM antigen antibodies such as Theragyn and Therex; anti-PSA antibodies; anti-PSCA antibodies such as IG8; anti-Ptk antbodies; anti-PTN antibodies; anti-RANKL antibodies such as AMG-162; anti-RLIP76 antibodies; anti-SK-1 antigen antibodies such as Monopharm C; anti-STEAP antibodies; anti-TAG72 antibodies such as CC49-SCA and MDX-220; anti-TGFβ antibodies such as CAT-152; anti-TNF-α antibodies such as CDP571, CDP870, D2E7, Humira® (adalimumab), and Remicade® (infliximab); anti-TRAIL-R1 and TRAIL-R2 antibodies; anti-VE-cadherin-2 antibodies; and anti-VLA-4 antibodies such as Antegren™. Furthermore, anti-idiotype antibodies including but not limited to the GD3 epitope antibody BEC2 and the gp72 epitope antibody 105AD7, may be used. In addition, bispecific antibodies including but not limited to the anti-CD3/CD20 antibody Bi20 may be used.

Examples of antibodies that may be co-administered to treat autoimmune or inflammatory disease, transplant rejection, GVHD, and the like include, but are not limited to, anti-α4β7 integrin antibodies such as LDP-02, anti-beta2 integrin antibodies such as LDP-01, anti-complement (C5) antibodies such as 5G1.1, anti-CD2 antibodies such as BTI-322, MEDI-507, anti-CD3 antibodies such as OKT3, SMART anti-CD3, anti-CD4 antibodies such as IDEC-151, MDX-CD4, OKT4A, anti-CD11a antibodies, anti-CD14 antibodies such as IC14, anti-CD18 antibodies, anti-CD23 antibodies such as IDEC 152, anti-CD25 antibodies such as Zenapax, anti-CD40L antibodies such as 5c8, Antova, IDEC-131, anti-CD64 antibodies such as MDX-33, anti-CD80 antibodies such as IDEC-114, anti-CD147 antibodies such as ABX-CBL, anti-E-selectin antibodies such as CDP850, anti-gpIIb/IIIa antibodies such as ReoPro/Abcixima, anti-ICAM-3 antibodies such as ICM3, anti-ICE antibodies such as VX-740, anti-FcγR1 antibodies such as MDX-33, anti-IgE antibodies such as rhuMab-E25, anti-IL-4 antibodies such as SB-240683, anti-IL-5 antibodies such as SB-240563, SCH55700, anti-IL-8 antibodies such as ABX-IL8, anti-interferon gamma antibodies, and anti-TNFa antibodies such as CDP571, CDP870, D2E7, Infliximab, MAK-195F, anti-VLA-4 antibodies such as Antegren. Examples of other Fc-containing molecules that may be co-administered to treat autoimmune or inflammatory disease, transplant rejection, GVHD, and the like include, but are not limited to, the p75 TNF receptor/Fc fusion Enbrel® (etanercept) and Regeneron's IL-1 trap.

Examples of antibodies that may be co-administered to treat infectious diseases include, but are not limited to, anti-anthrax antibodies such as ABthrax, anti-CMV antibodies such as CytoGam and sevirumab, anti-cryptosporidium antibodies such as CryptoGAM, Sporidin-G, anti-helicobacter antibodies such as Pyloran, anti-hepatitis B antibodies such as HepeX-B, Nabi-HB, anti-HIV antibodies such as HRG-214, anti-RSV antibodies such as felvizumab, HNK-20, palivizumab, RespiGam, and anti-staphylococcus antibodies such as Aurexis, Aurograb, BSYX-A110, and SE-Mab.

Alternatively, the anti-CD30 antibodies of the present invention may be co-administered or with one or more other molecules that compete for binding to one or more Fc receptors. For example, co-administering inhibitors of the inhibitory receptor FcγRIIb may result in increased effector function. Similarly, co-administering inhibitors of the activating receptors such as FcγRIIIa may minimize unwanted effector function. Fc receptor inhibitors include, but are not limited to, Fc molecules that are engineered to act as competitive inhibitors for binding to FcγRIIb FcγRIIIa, or other Fc receptors, as well as other immunoglobulins and specifically the treatment called IVIg (intravenous immunoglobulin). In one embodiment, the inhibitor is administered and allowed to act before the anti-CD30 antibody is administered. An alternative way of achieving the effect of sequential dosing would be to provide an immediate release dosage form of the Fc receptor inhibitor and then a sustained release formulation of the anti-CD30 antibody of the invention. The immediate release and controlled release formulations could be administered separately or be combined into one unit dosage form. Administration of an FcγRIIb inhibitor may also be used to limit unwanted immune responses, for example anti-Factor VIII antibody response following Factor VIII administration to hemophiliacs.

In one embodiment, the anti-CD30 antibodies of the present invention are administered with a chemotherapeutic agent. By "chemotherapeutic agent" as used herein is meant a chemical compound useful in the treatment of cancer. Examples of chemotherapeutic agents include but are not limited to alkylating agents such as thiotepa and cyclosphosphamide (CYTOXAN™); alkyl sulfonates such as busulfan, improsulfan and piposulfan; androgens such as calusterone, dromostanolone propionate, epitiostanol, mepitiostane, testolactone; anti-adrenals such as aminoglutethimide, mitotane, trilostane; anti-androgens such as flutamide, nilutamide, bicalutamide, leuprolide, and goserelin; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti estrogens including for example tamoxifen, raloxifene, aromatase inhibiting 4(5)-imidazoles, 4-hydroxytamoxifen, trioxifene, keoxifene, LY 117018, onapristone, and toremifene (Fareston); antimetabolites such as methotrexate and 5-fluorouracil (5-FU); folic acid analogues such as denopterin, methotrexate, pteropterin, trimetrexate; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; folic acid replenisher such as frolinic acid; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; platinum analogs such as cisplatin and carboplatin; vinblastine; platinum; proteins such as arginine deiminase and asparaginase; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; taxanes, e.g. paclitaxel (TAXOL®, Bristol-Myers Squibb Oncology, Princeton, N.J.) and docetaxel (TAXOTERE®, Rhne-Poulenc Rorer, Antony, France); topoisomerase inhibitor RFS 2000; thymidylate synthase inhibitor (such as Tomudex); additional chemotherapeutics including aceglatone; aldophosphamide glycoside; aminolevulinic acid; amsacrine; bestrabucil; bisantrene; edatraxate; defofamine; demecolcine; diaziquone; difluoromethylornithine (DMFO); elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; chlorambucil; gemcitabine; 6-thioguanine; mercaptopurine; methotrexate; etoposide (VP-16); ifosfamide; mitomycin C; mitoxantrone; vincristine; vinorelbine; navelbine; novantrone; teniposide; daunomycin; aminopterin; xeloda; ibandronate; CPT-11; retinoic acid; esperamicins; capecitabine. Pharmaceutically acceptable salts, acids or derivatives of any of the above may also be used.

A chemotherapeutic or other cytotoxic agent may be administered as a prodrug. By "prodrug" as used herein is meant a precursor or derivative form of a pharmaceutically active substance that is less cytotoxic to tumor cells compared to the parent drug and is capable of being enzymatically activated or converted into the more active parent form. See, for example Wilman, 1986, Biochemical Society Transactions, 615th Meeting Belfast, 14:375-382; Stella et al., "Prodrugs: A Chemical Approach to Targeted Drug Delivery," Directed Drug Delivery; and Borchardt et al., (ed.): 247-267, Humana Press, 1985, each of which is incorporated by reference in its entirety. The prodrugs that may find use with the present invention include but are not limited to phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use with the anti-CD30 antibodies of the present invention include but are not limited to any of the aforementioned chemotherapeutic agents.

A variety of other therapeutic agents may find use for administration with the anti-CD30 antibodies of the present invention. In one embodiment, the anti-CD30 antibody is administered with an anti-angiogenic agent. By "anti-angiogenic agent" as used herein is meant a compound that blocks, or interferes to some degree, the development of blood vessels. The anti-angiogenic factor may, for instance, be a small molecule or a protein, for example an antibody, Fc fusion, or cytokine, that binds to a growth factor or growth factor receptor involved in promoting angiogenesis. The preferred anti-angiogenic factor herein is an antibody that binds to Vascular Endothelial Growth Factor (VEGF). Other agents that inhibit signaling through VEGF may also be used, for example RNA-based therapeutics that reduce levels of VEGF or VEGF-R expression, VEGF-toxin fusions, Regeneron's VEGF-trap, and antibodies that bind VEGF-R. In an alternate embodiment, the anti-CD30 antibody is administered with a therapeutic agent that induces or enhances adaptive immune response, for example an antibody that targets CTLA-4. Additional anti-angiogenesis agents include, but are not limited to, angiostatin (plasminogen fragment), antithrombin III, angiozyme, ABT-627, Bay 12-9566, benefin, bevacizumab, bisphosphonates, BMS-275291, cartilage-derived inhibitor (CDI), CAI, CD59 complement fragment, CEP-7055, Col 3, combretastatin A-4, endostatin (collagen XVIII fragment), farnesyl transferase inhibitors, fibronectin fragment, gro-beta, halofuginone, heparinases, heparin hexasaccharide fragment, HMV833, human chorionic gonadotropin (hCG), IM-862, interferon alpha, interferon beta, interferon gamma, interferon inducible protein 10 (IP-10), interleukin-12, kringle 5 (plasminogen fragment), marimastat, metalloproteinase inhibitors (eg. TIMPs), 2-methodyestradiol, MMI 270 (CGS 27023A), plasminogen activiator inhibitor (PAI), platelet factor-4 (PF4), prinomastat, prolactin 16 kDa fragment, proliferin-related protein (PRP), PTK 787/ZK 222594, retinoids, solimastat, squalamine, SS3304, SU5416, SU6668, SU11248, tetrahydrocortisol-S, tetrathiomolybdate, thalidomide, thrombospondin-1 (TSP-1), TNP-470, transforming growth factor beta (TGF-β), vasculostatin, vasostatin (calreticulin fragment), ZS6126, and ZD6474.

In a preferred embodiment, the anti-CD30 antibody is administered with a tyrosine kinase inhibitor. By "tyrosine kinase inhibitor" as used herein is meant a molecule that inhibits to some extent tyrosine kinase activity of a tyrosine kinase. Examples of such inhibitors include but are not limited to quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis(4-fluoroanilino)phthalimide); tyrphostines containing nitrothiophene moieties; PD-0183805 (Warner-Lambert); antisense molecules (e.g. those that bind to ErbB-encoding nucleic acid); quinoxalines (U.S. Pat. No. 5,804,396); tryphostins (U.S. Pat. No. 5,804,396); ZD6474 (Astra Zeneca); PTK-787 (Novartis/Schering A G); pan-ErbB inhibitors such as C1-1033 (Pfizer); Affinitac (ISIS 3521; Isis/Lilly); Imatinib mesylate (STI571, Gleevec®; Novartis); PKI 166 (Novartis); GW2016 (Glaxo SmithKline); C1-1033 (Pfizer); EKB-569 (Wyeth); Semaxinib (Sugen); ZD6474 (AstraZeneca); PTK-787 (Novartis/Schering AG); INC-1C11 (Imclone); or as described in any of the following patent publications: U.S. Pat. No. 5,804,396; PCT WO 99/09016 (American Cyanimid); PCT WO 98/43960 (American Cyanamid); PCT WO 97/38983 (Warner-Lambert); PCT WO 99/06378 (Warner-Lambert); PCT WO 99/06396 (Warner-Lambert); PCT WO 96/30347 (Pfizer, Inc); PCT WO 96/33978 (AstraZeneca); PCT WO96/3397 (AstraZeneca); PCT WO 96/33980 (AstraZeneca), gefitinib (IRESSA™, ZD1839, AstraZeneca), and OSI-774 (Tarceva™, OSI Pharmaceuticals/Genentech).

In another embodiment, the anti-CD30 antibody is administered with one or more immunomodulatory agents. Such agents may increase or decrease production of one or more cytokines, up- or down-regulate self-antigen presentation, mask MHC antigens, or promote the proliferation, differentiation, migration, or activation state of one or more types of immune cells. Immunomodulatory agents include but are not limited to: non-steroidal anti-inflammatory drugs (NSAIDs) such as asprin, ibuprofed, celecoxib, diclofenac, etodolac, fenoprofen, indomethacin, ketoralac, oxaprozin, nabumentone, sulindac, tolmentin, rofecoxib, naproxen, ketoprofen, and nabumetone; steroids (eg. glucocorticoids, dexamethasone, cortisone, hydroxycortisone, methylprednisolone, prednisone, prednisolone, trimcinolone, azulfidineicosanoids such as prostaglandins, thromboxanes, and leukotrienes; as well as topical steroids such as anthralin, calcipotriene, clobetasol, and tazarotene); cytokines such as TGFb, IFNa, IFNb, IFNg, IL-2, IL-4, IL-10; cytokine, chemokine, or receptor antagonists including antibodies, soluble receptors, and receptor-Fc fusions against BAFF, B7, CCR2, CCR5, CD2, CD3, CD4, CD6, CD7, CD8, CD11, CD14, CD15, CD17, CD18, CD20, CD23, CD28, CD40, CD40L, CD44, CD45, CD52, CD64, CD80, CD86, CD147, CD152, complement factors (C5, D) CTLA4, eotaxin, Fas, ICAM, ICOS, IFNα, IFNβ, IFNγ, IFNAR, IgE, IL-1, IL-2, IL-2R, IL-4, IL-5R, IL-6, IL-8, IL-9 IL-12, IL-13, IL-13R1, IL-15, IL-18R, IL-23, integrins, LFA-1, LFA-3, MHC, selectins, TGFβ, TNFα, TNFβ, TNF-R1, T-cell receptor, including Enbrel® (etanercept), Humira® (adalimumab), and Remicade® (infliximab); heterologous anti-lymphocyte globulin; other immunomodulatory molecules such as 2-amino-6-aryl-5 substituted pyrimidines, anti-idiotypic antibodies for MHC binding peptides and MHC fragments, azathioprine, brequinar, bromocriptine, cyclophosphamide, cyclosporine A, D-penicillamine, deoxyspergualin, FK506, glutaraldehyde, gold, hydroxychloroquine, leflunomide, malononitriloamides (eg. leflunomide), methotrexate, minocycline, mizoribine, mycophenolate mofetil, rapamycin, and sulfasasazine.

In an alternate embodiment, anti-CD30 antibody of the present invention are administered with a cytokine. By "cytokine" as used herein is meant a generic term for proteins released by one cell population that act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

In a preferred embodiment, cytokines or other agents that stimulate cells of the immune system are co-administered with the anti-CD30 antibody of the present invention. Such a mode of treatment may enhance desired effector function. For example, agents that stimulate NK cells, including but not limited to IL-2 may be co-administered. In another embodiment, agents that stimulate macrophages, including but not limited to C5a, formyl peptides such as N-formyl-methionyl-leucyl-phenylalanine (Beigier-Bompadre et. al. (2003) Scand. J. Immunol. 57: 221-8, entirely incorporated by reference), may be co-administered. Also, agents that stimulate neutrophils, including but not limited to G-CSF, GM-CSF, and the like may be administered. Furthermore, agents that promote migration of such immunostimulatory cytokines may be used. Also additional agents including but not limited to interferon gamma, IL-3 and IL-7 may promote one or more effector functions.

In an alternate embodiment, cytokines or other agents that inhibit effector cell function are co-administered with the anti-CD30 antibody of the present invention. Such a mode of treatment may limit unwanted effector function.

In an additional embodiment, the anti-CD30 antibody is administered with one or more antibiotics, including but not limited to: aminoglycoside antibiotics (eg. apramycin, arbekacin, bambermycins, butirosin, dibekacin, gentamicin, kanamycin, neomycin, netilmicin, paromomycin, ribostamycin, sisomycin, spectrinomycin), aminocyclitols (eg. sprctinomycin), amphenicol antibiotics (eg. azidamfenicol, chloramphenicol, florfrnicol, and thiamphemicol), ansamycin antibiotics (eg. rifamide and rifampin), carbapenems (eg. imipenem, meropenem, panipenem); cephalosporins (eg. cefaclor, cefadroxil, cefamandole, cefatrizine, cefazedone, cefozopran, cefpimizole, cefpiramide, cefpirome, cefprozil, cefuroxine, cefixime, cephalexin, cephradine), cephamycins (cefbuperazone, cefoxitin, cefminox, cefmetazole, and cefotetan); lincosamides (eg. clindamycin, lincomycin); macrolide (eg. azithromycin, brefeldin A, clarithromycin, erythromycin, roxithromycin, tobramycin), monobactams (eg. aztreonam, carumonam, and tigernonam); mupirocin; oxacephems (eg. flomoxef, latamoxef, and moxalactam); penicillins (eg. amdinocillin, amdinocillin pivoxil, amoxicillin, bacampicillin, bexzylpenicillinic acid, benzylpenicillin sodium, epicillin, fenbenicillin, floxacillin, penamecillin, penethamate hydriodide, penicillin o-benethamine, penicillin O, penicillin V, penicillin V benzoate, penicillin V hydrabamine, penimepicycline, and phencihicillin potassium); polypeptides (eg. bacitracin, colistin, polymixin B, teicoplanin, vancomycin); quinolones (amifloxacin, cinoxacin, ciprofloxacin, enoxacin, enrofloxacin, feroxacin, flumequine, gatifloxacin, gemifloxacin, grepafloxacin, lomefloxacin, moxifloxacin, nalidixic acid, norfloxacin, ofloxacin, oxolinic acid, pefloxacin, pipemidic acid, rosoxacin, rufloxacin, sparfloxacin, temafloxacin, tosufloxacin, trovafloxacin); rifampin; streptogramins (eg. quinupristin, dalfopristin); sulfonamides (sulfanilamide, sulfamethoxazole); tetracyclenes (chlortetracycline, demeclocycline hydrochloride, demethylchlortetracycline, doxycycline, duramycin, minocycline, neomycin, oxytetracycline, streptomycin, tetracycline, vancomycin).

Anti-fungal agents such as amphotericin B, ciclopirox, clotrimazole, econazole, fluconazole, flucytosine, itraconazole, ketoconazole, niconazole, nystatin, terbinafine, terconazole, and tioconazole may also be used.

Antiviral agents including protease inhibitors, reverse transcriptase inhibitors, and others, including type I interferons, viral fusion inhibitors, and neuramidase inhibitors, may also be used. Examples of antiviral agents include, but are not limited to, acyclovir, adefovir, amantadine, amprenavir, clevadine, enfuvirtide, entecavir, foscarnet, gangcyclovir, idoxuridine, indinavir, lopinavir, pleconaril, ribavirin, rimantadine, ritonavir, saquinavir, trifluridine, vidarabine, and zidovudine, may be used.

The anti-CD30 antibodies of the present invention may be combined with other therapeutic regimens. For example, in one embodiment, the patient to be treated with an anti-CD30 antibody of the present invention may also receive radiation therapy. Radiation therapy can be administered according to protocols commonly employed in the art and known to the skilled artisan. Such therapy includes but is not limited to cesium, iridium, iodine, or cobalt radiation. The radiation therapy may be whole body irradiation, or may be directed locally to a specific site or tissue in or on the body, such as the lung, bladder, or prostate. Typically, radiation therapy is administered in pulses over a period of time from about 1 to 2 weeks. The radiation therapy may, however, be administered over longer periods of time. For instance, radiation therapy may be administered to patients having head and neck cancer for about 6 to about 7 weeks. Optionally, the radiation therapy may be administered as a single dose or as multiple, sequential doses. The skilled medical practitioner can determine empirically the appropriate dose or doses of radiation therapy useful herein. In accordance with another embodiment of the invention, the anti-CD30 antibody of the present invention and one or more other anti-cancer therapies are employed to treat cancer cells ex vivo. It is contemplated that such ex vivo treatment may be useful in bone marrow transplantation and particularly, autologous bone marrow transplantation. For instance, treatment of cells or tissue(s) containing cancer cells with anti-CD30 antibody and one or more other anti-cancer therapies, such as described above, can be employed to deplete or substantially deplete the cancer cells prior to transplantation in a recipient patient.

Radiation therapy may also comprise treatment with an isotopically labeled molecule, such as an antibody. Examples of radioimmunotherapeutics include but Zevalin™ (Y-90 labeled anti-CD20), LymphoCide™ (Y-90 labeled anti-CD22) and Bexxar™ (I-131 labeled anti-CD20)

It is of course contemplated that the anti-CD30 antibodies of the invention may employ in combination with still other therapeutic techniques such as surgery or phototherapy.

A number of the receptors that may interact with the anti-CD30 antibodies of the present invention are polymorphic in the human population. For a given patient or population of patients, the efficacy of the anti-CD30 antibodies of the present invention may be affected by the presence or absence of specific polymorphisms in proteins. For example, FcγRIIIA is polymorphic at position 158, which is commonly either V (high affinity) or F (low affinity). Patients with the V/V homozygous genotype are observed to have a better clinical response to treatment with the anti-CD20 antibody Rituxan® (rituximab), likely because these patients mount a stronger NK response (Dall'Ozzo et. al. (2004) Cancer Res. 64:4664-9, entirely incorporated by reference). Additional polymorphisms include but are not limited to FcγRIIA R131 or H131, and such polymorphisms are known to either increase or decrease Fc binding and subsequent biological activity, depending on the polymorphism. anti-CD30 antibodies of the present invention may bind preferentially to a particular polymorphic form of a receptor, for example FcγRIIIA 158 V, or to bind with equivalent affinity to all of the polymorphisms at a particular position in the receptor, for example both the 158V and 158F polymorphisms of FcγRIIIA. In a preferred embodiment, anti-CD30 antibodies of the present invention may have equivalent binding to polymorphisms may be used in an antibody to eliminate the differential efficacy seen in patients with different polymorphisms. Such a property may give greater consistency in therapeutic response and reduce non-responding patient populations. Such variant Fc with identical binding to receptor polymorphisms may have increased biological activity, such as ADCC, CDC or circulating half-life, or alternatively decreased activity, via modulation of the binding to the relevant Fc receptors. In a preferred embodiment, anti-CD30 antibodies of the present invention may bind with higher or lower affinity to one of the polymorphisms of a receptor, either accentuating the existing difference in binding or reversing the difference. Such a property may allow creation of therapeutics particularly tailored for efficacy with a patient population possessing such polymorphism. For example, a patient population possessing a polymorphism with a higher affinity for an inhibitory receptor such as FcγRIIB could receive a drug containing an anti-CD30 antibody with reduced binding to such polymorphic form of the receptor, creating a more efficacious drug.

In a preferred embodiment, patients are screened for one or more polymorphisms in order to predict the efficacy of the anti-CD30 antibodies of the present invention. This information may be used, for example, to select patients to include or exclude from clinical trials or, post-approval, to provide guidance to physicians and patients regarding appropriate dosages and treatment options. For example, in patients that are homozygous or heterozygous for FcγRIIIA 158F antibody drugs such as the anti-CD20 mAb, Rituximab are minimally effective (Carton 2002 Blood 99: 754-758; Weng 2003 J. Clin. Oncol. 21:3940-3947, both entirely incorporated by reference); such patients may show a much better clinical response to the antibodies of the present invention. In one embodiment, patients are selected for inclusion in clinical trials for an antibody of the present invention if their genotype indicates that they are likely to respond significantly better to an antibody of the present invention as compared to one or more currently used antibody therapeutics. In another embodiment, appropriate dosages and treatment regimens are determined using such genotype information. In another embodiment, patients are selected for inclusion in a clinical trial or for receipt of therapy post-approval based on their polymorphism genotype, where such therapy contains an anti-CD30 antibody engineered to be specifically efficacious for such population, or alternatively where such therapy contains an anti-CD30 antibody that does not show differential activity to the different forms of the polymorphism.

Included in the present invention are diagnostic tests to identify patients who are likely to show a favorable clinical response to an anti-CD30 antibody of the present invention, or who are likely to exhibit a significantly better response when treated with an anti-CD30 antibody of the present invention versus one or more currently used antibody therapeutics. Any of a number of methods for determining FcγR polymorphisms in humans known in the art may be used.

Furthermore, the present invention comprises prognostic tests performed on clinical samples such as blood and tissue samples. Such tests may assay for effector function activity, including but not limited to ADCC, CDC, phagocytosis, and opsonization, or for killing, regardless of mechanism, of cancerous or otherwise pathogenic cells. In a preferred embodiment, ADCC assays, such as those described previously, are used to predict, for a specific patient, the efficacy of a given anti-CD30 antibody of the present invention. Such information may be used to identify patients for inclusion or exclusion in clinical trials, or to inform decisions regarding appropriate dosages and treatment regemins. Such information may also be used to select a drug that contains a particular anti-CD30 antibody that shows superior activity in such assay.

EXAMPLES

Examples are provided below to illustrate the present invention. These examples are not meant to constrain the present invention to any particular application or theory of operation.

For reference to immunoglobulin variable regions, positions are numbered according to the Kabat numbering scheme. For reference to immunoglobulin constant regions, positions are numbered according to the EU index as in Kabat (Kabat et al., 1991, *Sequences of Proteins of Immunological Interest*, 5th Ed., United States Public Health Service, National Institutes of Health, Bethesda).

Example 1

Antibody Fv Regions that Target CD30

Variants of the anti-CD30 antibody AC10 (Bowen et al. Journal of Immunology, 1993, 151: 5896) (sequences provided in FIG. 1) were generated to reduce immunogenicity in humans by applying a string optimization algorithm, as described in U.S. Ser. No. 11/004,590 (herein entirely incorporated by reference). This algorithm heuristically samples multiple amino acid mutations that exist in the diversity of the human VLK and VH germline sequences, and calculates the host string content (HSC). Variant sequences were also evaluated for structural and functional integrity using a nearest neighbor structure-based scoring method (U.S. Ser. No. 60/528,229, filed Dec. 8, 2003, entitled Protein Engineering with Analogous Contact Environments). A series of variant heavy chain (referred to as H1, H2, and H3) and light chain (L1, L2, and L3) AC10 sequences were chosen to characterize experimentally.

The genes for the variable regions of AC10 WT (L0 and H0) and variants (L1, L2, L3, H1, H2, and H3) were constructed using recursive PCR, and subcloned into a the mammalian expression vector pcDNA3.1Zeo (Invitrogen) comprising the full length light kappa (CLK) and heavy chain IgG1 constant regions. All sequences were sequenced to confirm the fidelity of the sequence. Plasmids containing heavy chain gene (VH-CH1-CH2-CH3) (wild-type or variants) were co-transfected with plasmid containing light chain gene (VL-CLK) in all combinations (L0/H0, L0/H1, L0/H2, L0/H3, L1/H0, L1/H1, L1/H2, L1/H3, L2/H0, L2/H1, L2/H2, L2/H3, L3/H0, L3/H1, L3/H2, L3/H3) into 293T cells. Here, for example, L2/H3 refers to the L2 AC10 VL paired with H3 AC10 VH. Media were harvested 5 days after transfection, and antibodies were purified from the supernatant using protein A affinity chromatography (Pierce, Catalog #20334).

Figure 2B:
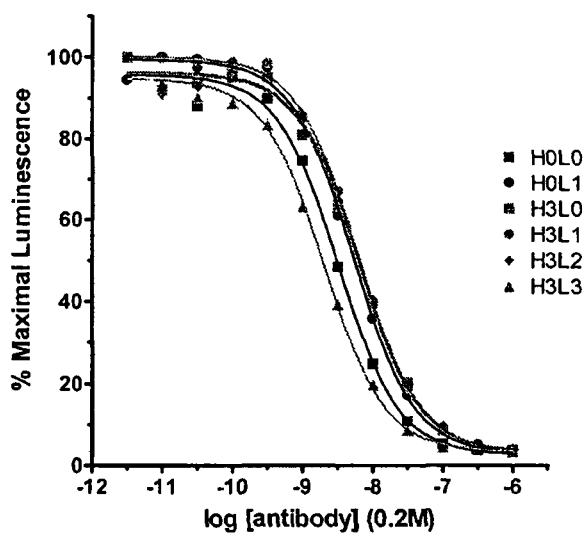

WT and variant antibodies were experimentally tested for their capacity to bind CD30 antigen. Binding affinity to human CD30 by the AC10 WT and variant antibodies was measured using a quantitative and extremely sensitive method, AlphaScreen™ assay. The AlphaScreen™ assay is a bead-based non-radioactive luminescent proximity assay. Laser excitation of a donor bead excites oxygen, which if sufficiently close to the acceptor bead will generate a cascade of chemiluminescent events, ultimately leading to fluorescence emission at 520-620 nm. The AlphaScreen™ assay was applied as a competition assay for screening the antibodies. WT AC10 antibody was biotinylated by standard methods for attachment to streptavidin donor beads (Perkin Elmer). Commericial CD30 was conjugated to digoxigenin (DIG) (Roche Diagnostics) for attachment to anti-DIG acceptor beads (Perkin Elmer). In the absence of competing AC10 variants, WT antibody and CD30 interact and produce a signal at 520-620 nm. Addition of untagged AC10 variant competes with the WT AC10/CD30 interaction, reducing fluorescence quantitatively to enable determination of relative binding affinities. FIGS. 2a and 2b show binding of WT (H0L0) and AC10 variant antibodies to CD30 using the AlphaScreen™ assay. The data were fit to a one site competition model using nonlinear regression, and these fits are represented by the curves in the figure. These fits provide the inhibitory concentration 50% (IC50) (i.e. the concentration required for 50% inhibition) for each antibody, thus enabling the relative binding affinities relative to WT to be determined. FIG. 3 provides the IC50's and Fold IC50's relative to WT for fits to these binding curves. The AC10 variants display an array of CD30 binding affinities, with a number of variants binding CD30 with affinity comparable to or better affinity than WT AC10.

Figure 4:
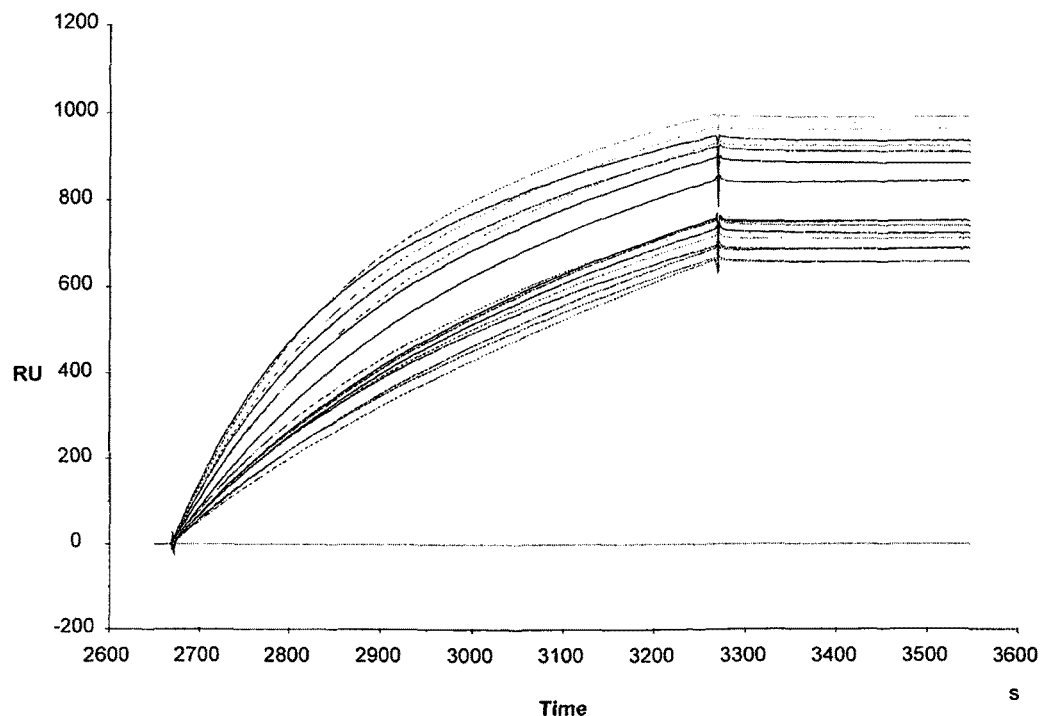
FIG. 4. SPR sensorgrams showing binding of AC10 WT and variant full length antibodies to the CD30 target antigen. The curves consist of an association phase and dissociation phase, the separation being marked by a little spike on each curve.

Antigen affinities of the AC10 variants were also measured using Surface Plasmon Resonance (SPR) (Biacore, Uppsala, Sweden). SPR allows for the measurement of direct binding rates and affinities of protein-protein interactions, and thus provides an excellent complementary binding assay to the AlphaScreen™ assay. CD30 fused to the Fc region of IgG1 (R&D Systems) was immobilized on a Protein A SPR chip, the surface was blocked with Fc, and WT and variant AC10 antibodies were flowed over the chip at a range of concentrations. The resulting sensorgrams are shown in FIG. 4. Global Langmuir fits were carried out for the concentrations series using the BiaEvaluation curve fitting software, providing the on-rate constant (ka), off-rate constant (kd), and equilibrium binding constant (KD=kd/ka) for the curves. FIG. 3 provides the KDs and Fold KDs relative to WT for the SPR data.

Based on these data, as well as sequence and structure scores, the H3L3 AC10 variant was chosen as a candidate for further study. The amino acid sequences of H3 and L3 are provided in FIG. 5.

Because the H3L3 AC10 variant sequences are derived from a HSC-increasing procedure in which substitution of structurally important positions is disallowed (or discouraged), it is likely that additional optimization of HSC is possible if those positions are allowed to vary in a secondary analysis. It is noted that, due to residue masking, mutations in the variants occur distal to the CDRs and VLNH interface. One or more subsequent substitutions may be explored to increase antigen affinity or further improve HSC, for example by mutating residues that were masked in the calculations and/or residues in or close to the CDRs or VL/VH interface. Thus the H3/L3 variant can be thought of as a primary variant or template for further optimization, and variants of H3/L3 can be thought of as secondary variants. In contrast to backmutating as with CDR grafted antibodies, secondary substitutions in the variants of the present invention will comprise forward or neutral mutations with respect to the host germ line, and thus are expected to only improve or unaffected HSC. An additional benefit of generating secondary variants is that, by exploring quality structural and string diversity, it is also possible that other properties can be optimized, for example affinity, activity, specificity, solubility, expression level, and effector function.

String analysis was carried out on the H3/L3 sequence to design a set of secondary substitutions that have neutral, positive, or minimal impact on HSC, and/or that have significant potential for optimization of antigen affinity and/or effector function. FIG. 6 provides this set of 70 VL (FIG. 6a) and 64 VH (FIG. 6b) single mutations. The H3 column provides the WT H3 amino acid, and the Sub column provides the designed substitution. Positions are numbered according to the Kabat numbering format, with Kabat CDR positions bolded. The provided string impact, defined in reference String app, describes the difference in HSC between the primary variant sequence, here H3/L3, and the secondary variant sequence.

Figure 7:
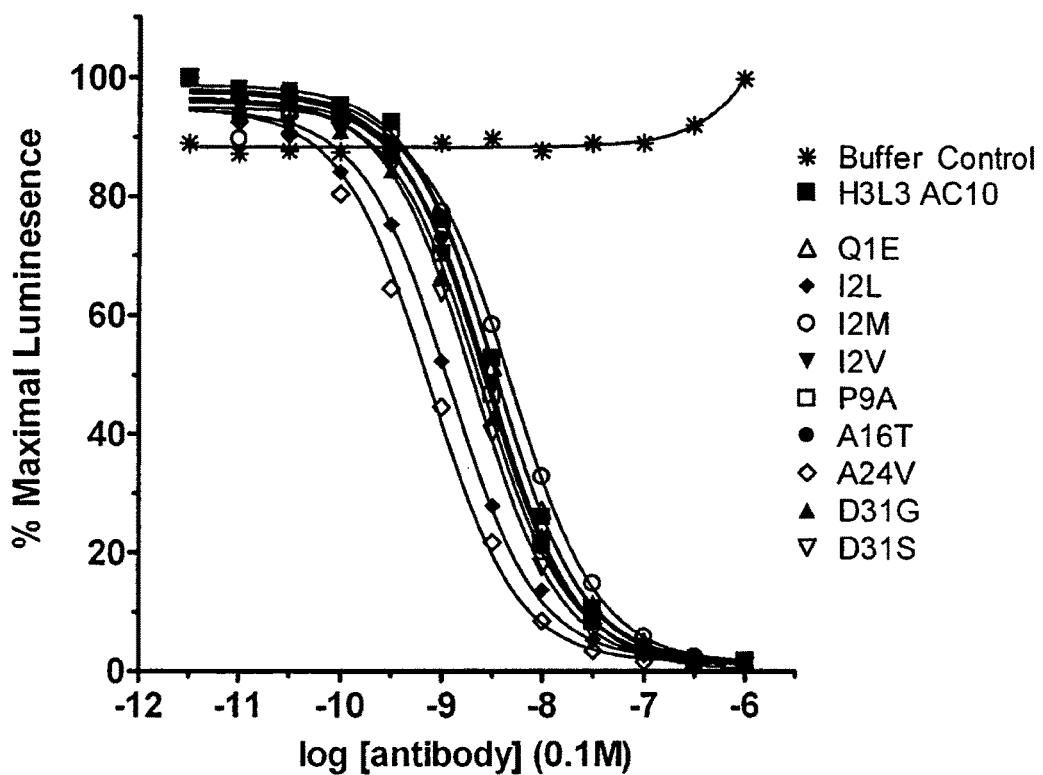
FIG. 7. AlphaScreen™ assay measuring binding between select H3L3 AC10 secondary variants and the target antigen CD30.

The secondary H3/L3 variants were constructed using quick change mutagenesis, and the full length antibodies were expressed and purified as described above. H3 variants comprised H3 variant VH chains (H3.1-H3.64) in combination with L3 VL, and L3 variants comprised L3 variant VL chains (L3.1-L3.70) in combination with H3 VH. The AlphaScreen™ assay was used to measure binding of the H3/L3 secondary variants to CD30 and FcγRIIIa (as described earlier), as well as to protein A using biotinylated AC10 bound directly to protein A acceptor beads and streptavidin donor beads. FIG. 7 provides AlphaScreen™ binding curves for binding of select AC10 variants to CD30. The Fold IC50's relative to WT H3/L3 for binding to CD30, FcγRIIIa, and protein A are provided in FIG. 6. A number of H3/L3 secondary variants provide comparable or improved binding to CD30 antigen relative to the H3/L3 parent, enabling the engineering of additional variants that comprise combinations of these substitutions, which may provide further enhancements in HSC and/or antigen affinity.

Secondary substitutions that show favorable properties with respect to antigen affinity, effector function, stability, solubility, expression, and the like, may be combined in subsequent variants to generate a more optimized therapeutic candidate. Two new VL and three new VH variants were designed that comprise combinations of the described secondary substitutions, referred to as L3.71, L3.72, H3.68, H3.69, and H3.70. FIG. 8 presents the sequences for each of these new AC10 VL and VH variants. These variants differ from WT (H0/L0) AC10 by the following number of mutations: L3.71-15, L3.72-15, H3.68-23, H3.69-27, and H3.70-30 mutations.

Figure 9:
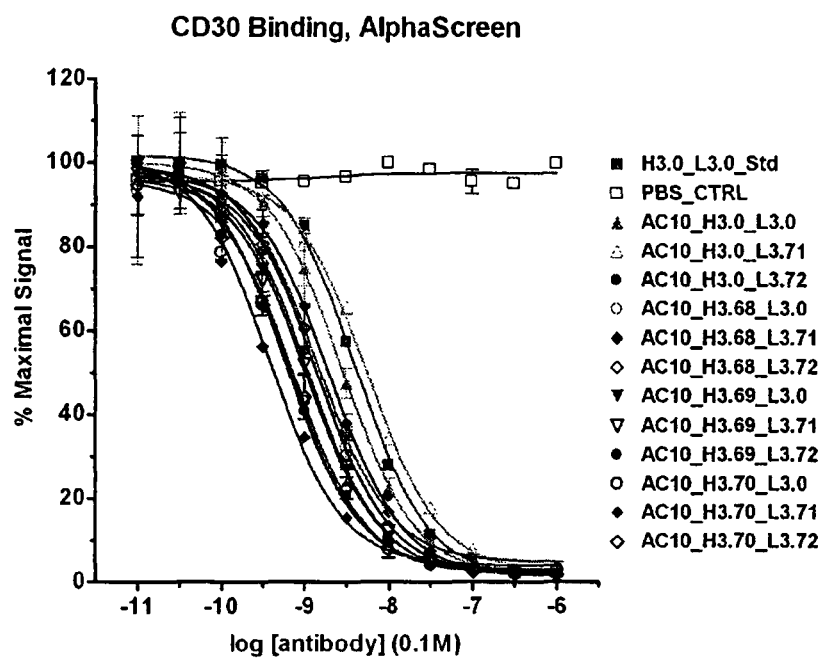
FIG. 9. AlphaScreen™ assay measuring binding between H3.68, H3.69, H3.70, L3.71, and L3.72 AC10 variants and the target antigen CD30.

These variants were constructed, expressed, and purified. AlphaScreen data measuring binding to human CD30 are provided in FIG. 9, and the IC50s and Fold affinities for these data are presented in FIG. 10.

Figure 12A:
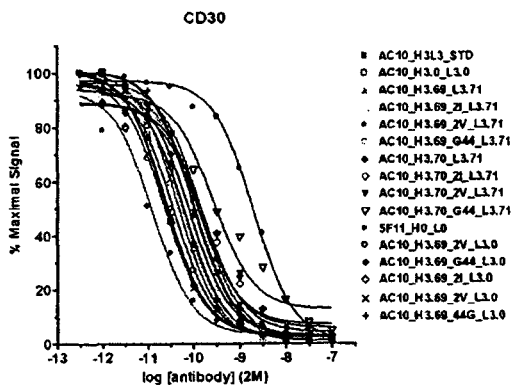
FIG. 12. AlphaScreen™ assay measuring binding of H3.69/L3.71 AC10 variants to CD30, protein A, and V158 FcγRIIIa.
Figure 12B:
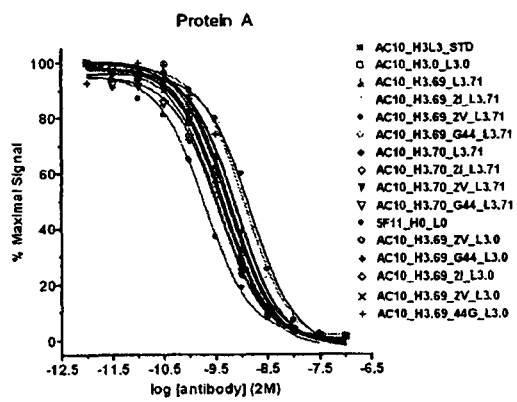
Figure 12C:
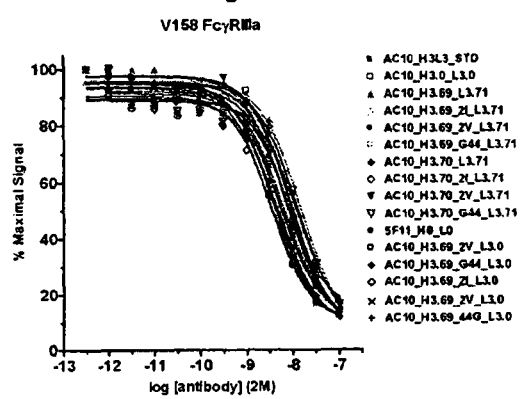

The H3.69/L3.71 variant was chosen for further characterization. Based on the data in FIG. 6, a set of variants was made in the H3.69/L3.71 AC10 variant. These are provided in FIG. 11. Data are in FIG. 12, with IC50's and Fold affinities in FIG. 11. The sequences of the H3.69_V2/L3.71 AC10 variant are provided in FIG. 13.

Example 2

Anti-CD30 Antibodies with Amino Acid Modifications that Enhance Effector Function Because the provided AC10 variants antibodies are clinical candidates for anti-cancer therapeutics, it may be advantageous to optimize their effector function. As previously described, substitutions can be engineered in the constant region of an antibody to provide favorable clinical properties. Combinations of the variants of the present invention with Fc modifications that alter effector function are anticipated. In a most preferred embodiment, one or more amino acid modifications that provide optimized binding to FcγRs and/or enhanced effector function described in U.S. Ser. No. 10/672,280, PCT US03/30249, and U.S. Ser. No. 10/822, 231, and U.S. Ser. No. 60/627,774, filed Nov. 12, 2004 and entitled "Optimized Fc Variants," each of which is incorporated by reference in its entirety, are combined with the AC10 variants of the present invention. The optimal anti-CD30 clinical candidate may comprise amino acid modifications that reduce immunogenicity and enhance effector function relative to a parent anti-CD30 antibody.

A number of optimized Fc variants, including I332E, S239D, V264I/I332E, S239D/I332E, and S239D/A330L/I332E, were constructed in the H0/L0 and H3/L0 AC10 IgG1 antibodies using quick change mutagenesis (Stratagene). Antibodies were expressed and purified as described above.

Figure 14A:
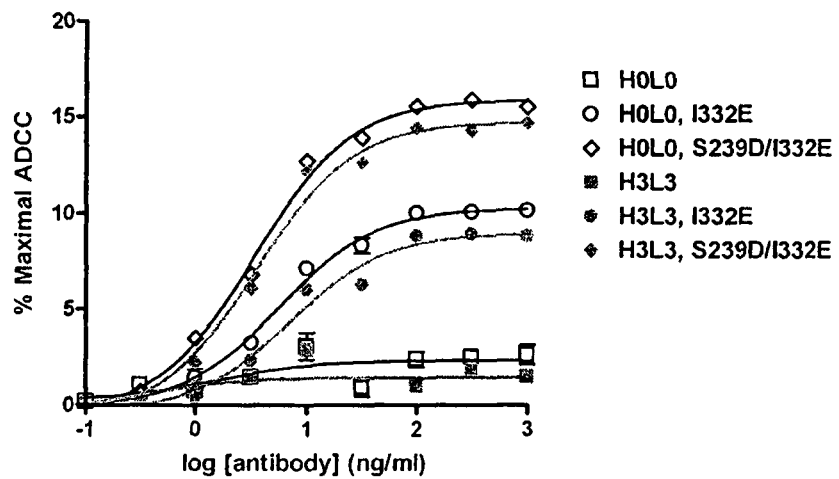
FIG. 14. Cell-based assay measuring ADCC capacity of WT (H0/L0) and H3/L3 AC10 antibodies comprising Fc variants that provide enhanced effector function. Raw data were normalized to a percentage scale of maximal cytotoxicity determined by Triton-X100 lysis of target cells.
Figure 14B:
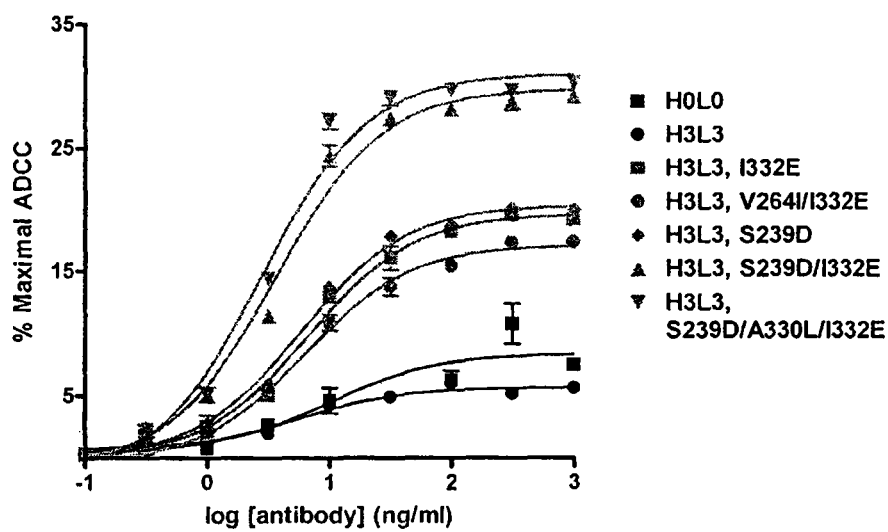

To assess the capacity of the AC10 variants to mediate effector function against CD30 expressing cells, the AC10 variants were tested in a cell-based ADCC assay. Human peripheral blood monocytes (PBMCs) were isolated from buffy-coat and used as effector cells, and CD30 positive L540 Hodgkin's lymphoma cells were used as target cells. L540 target cells were seeded at 20,000 per well in 96-well plates and treated with designated antibodies in triplicates starting at 1 µg/ml and in reduced concentrations in ½ log steps. PBMCs isolated using a Ficoll gradient and allotyped as FcγRIIIa 158 V/F were added at 25-fold excess of L540 cells and co-cultured for 4 hrs before processing for LDH activity using the Cytotoxicity Detection Kit (LDH, Roche Diagnostic Corporation, Indianapolis, Ind.) according to the manufacturer's instructions. The plates were read using a Wallac 1420 Victor²™. FIGS. 14a and 14b show the results of the ADCC assay comparing WT (H0/L0) and H3/L3 AC10 in combination with the optimized Fc variants. The graphs show that the antibodies differ not only in their EC50, reflecting their relative potency, but also in the maximal level of ADCC attainable by the antibodies at saturating concentrations, reflecting their relative efficacy. These two terms, potency and efficacy, are sometimes used loosely to refer to desired clinical properties. In the current experimental context, however, they are denoted as specific quantities, and therefore are here explicitly defined. By "potency" as used in the current experimental context is meant the EC50 of an anti-CD30 antibody. By "efficacy" as used in the current experimental context is meant the maximal possible effector function of an antibody at saturating levels. Considerable enhancements in potency and efficacy are observed for the Fc variant antibodies as compared to H0/L0 and H3/L3 AC10.

Although human IgG1 is the most commonly used constant region for therapeutic antibodies, other embodiments may utilize constant regions or variants thereof of other IgG immunoglobulin chains. Effector functions such as ADCC, ADCP, CDC, and serum half-life differ significantly between the different classes of antibodies, including for example human IgG1, IgG2, IgG3, IgG4, IgA1, IgA2, IgD, IgE, IgG, and IgM (Michaelsen et al., 1992, Molecular Immunology, 29(3): 319-326, entirely incorporated by reference). A number of studies have explored IgG1, IgG2, IgG3, and IgG4 variants in order to investigate the determinants of the effector function differences between them. See for example Canfield & Morrison, 1991, J. Exp. Med. 173: 1483-1491; Chappel et al., 1991, Proc. Natl. Acad. Sci. USA 88(20): 9036-9040; Chappel et al., 1993, Journal of Biological Chemistry 268:25124-25131; Tao et al., 1991, J . Exp. Med. 173: 1025-1028; Tao et al., 1993, J. Exp. Med. 178: 661-667; Redpath et al., 1998, Human Immunology, 59, 720-727, each of which is incorporated by reference in its entirety. Using methods known in the art, it is possible to determine corresponding or equivalent residues in proteins that have significant sequence or structural homology with each other. By the same token, it is possible to use such methods to engineer amino acid modifications in an antibody that comprise constant regions from other immunoglobulin classes, for example as described in U.S. Ser. Nos. 60/621,387 and 60/629,068, both entirely incorporated by reference, to provide optimal properties. As an example, the relatively poor effector function of IgG2 may be improved by replacing key FcγR binding residues with the corresponding amino acids in an IgG with better effector function, for example IgG1. For example, key residue differences between IgG2 and IgG1 with respect to FcγR binding may include P233, V234, A235, -236 (referring to a deletion in IgG2 relative to IgG1), and G327. Thus one or more amino acid modifications in the parent IgG2 wherein one or more of these residues is replaced with the corresponding IgG1 amino acids, P233E, V234L, A235L, -236G (referring to an insertion of a glycine at position 236), and G327A, may provide enhanced effector function. Furthermore, one or more additional amino acid modifications, for example the S239D, V264I, A330L, I332E, or combinations thereof as described above, may provide enhanced FcγR binding and effector function relative to the parent IgG2.

FIG. 15 provides constant region amino acid sequences that may be used in anti-CD30 antibodies of the present invention. These include the constant light chain kappa region, the four IgG isotypes IgG1, IgG2, IgG3, and IgG4, the IgG2 ELLGG constant region, and the IgG(1/2) ELLGG constant region. These sequences are not meant to constrain the present invention to these constant regions. For example, although the kappa constant chain (Cκ) was used in the present study, the lambda constant chain (Cλ) may be employed. As described, these sequences may serve as parent molecules for further modification. FIG. 16 provides the amino acid sequences of the full length light and heavy chains of one of the anti-CD30 antibodies of the present invention, specifically the H3.69_V2/L3.71 AC10 IgG(1/2) ELLGG antibody.

Figure 18A:
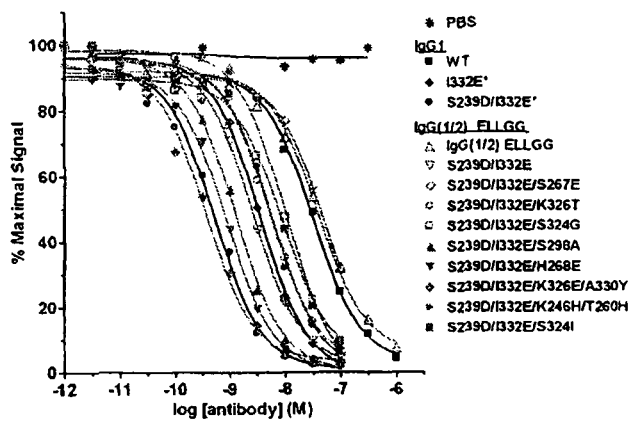
FIGS. 18a-18c. Competition AlphaScreen assay showing binding of WT and variant IgG antibodies to human V158 FcγRIIIa. IgG variants comprise the constant region of either IgG1 or IgG(1/2) ELLGG plus the indicated modifications. With the exception of 1332E and S239D/1332E IgG1, all IgG variants comprise the variable region of the anti-CD30 antibody H3.69_V2_L3.71 AC10. Variants 1332E IgG1 and S239D/1332E IgG1 comprise the variable region of the anti-CD30 antibody H3.69_L3.71 AC10.
Figure 18B:
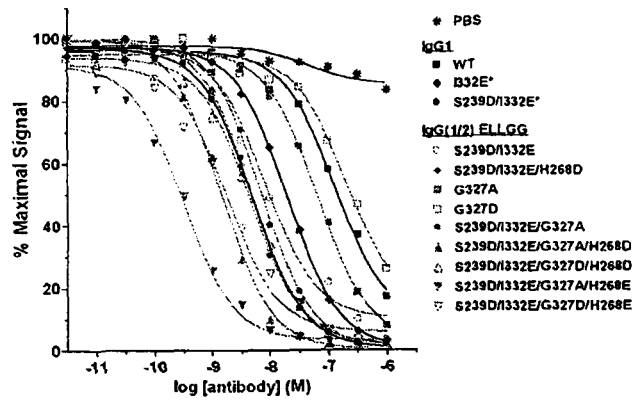
Figure 18C:
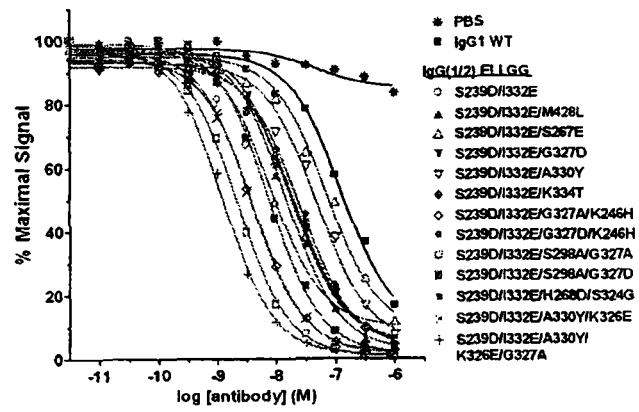
Figure 20A:
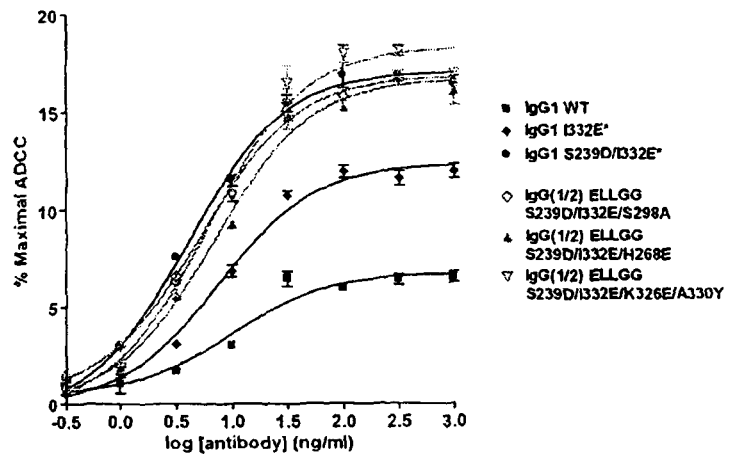
FIGS. 20a-20d. Cell-based ADCC assay of WT and variant IgGs with the variable region of the anti-CD30 antibody H3.69_V2_L3.71 AC10 or H3.69_L3.71 AC10 (133E and S239D/1332E IgG1). ADCC was measured by LDH activity using the Cytotoxicity Detection Kit (LDH, Roche Diagnostic Corporation, Indianapolis, Ind.) or the DELFIA® EuTDA-based cytotoxicity assay (Perkin Elmer, Mass.). For all assays, target cells were L540 Hodgkin's lymphoma cells and effector cells were human PBMCs. The figures show the dose-dependence of ADCC on antibody concentration for the indicated antibodies, normalized to the minimum and maximum fluorescence signal for each particular curve, provided by the baselines at low and high antibody concentrations respectively. The curves represent the fits of the data to a sigmoidal dose-response model using nonlinear regression.
Figure 20B:
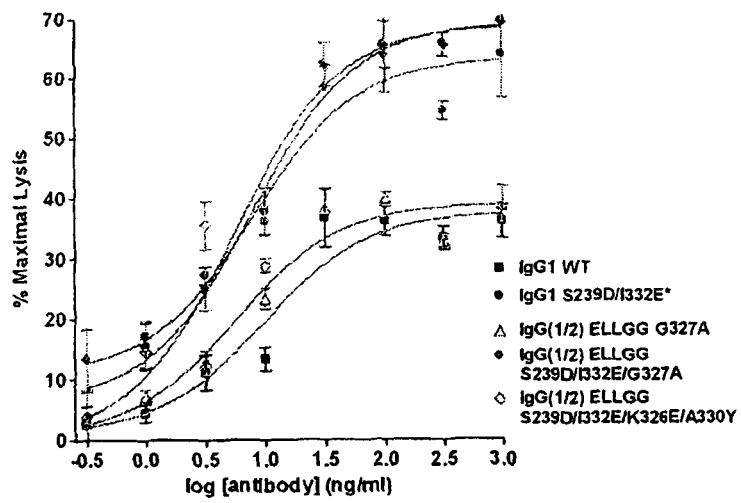
Figure 20C:
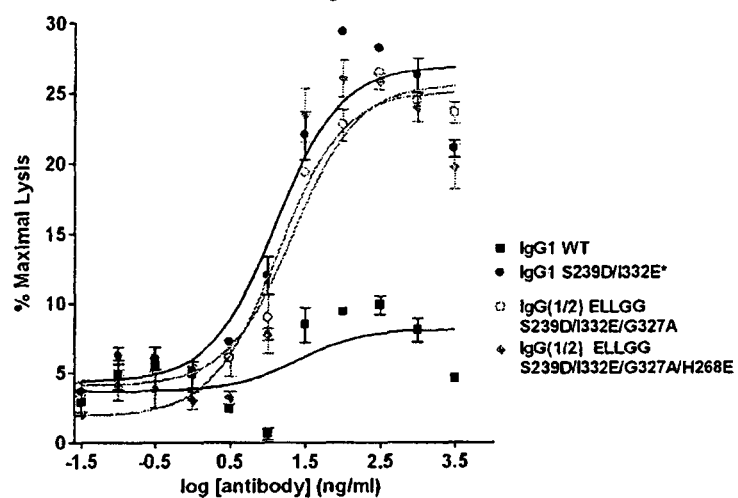
Figure 20D:
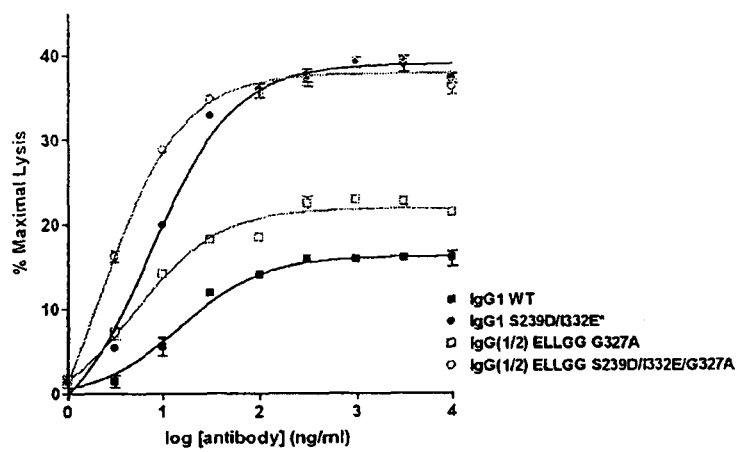
Figure 21A:
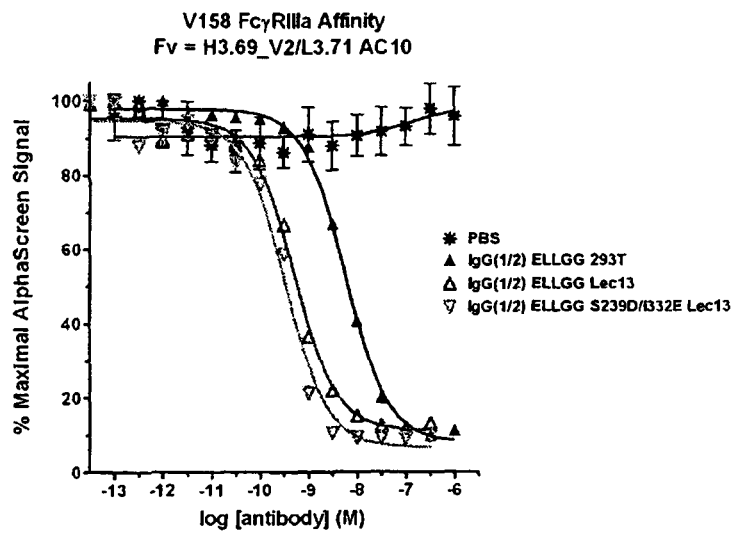
FIG. 21a. FcγR affinity of H3.69_V2/L3.71 AC10 IgG(1/2) ELLGG and S239D/1332E IgG(1/2) ELLGG antibodies expressed in 293T cells and the glycoengineering cell line Lec13.
Figure 21B:
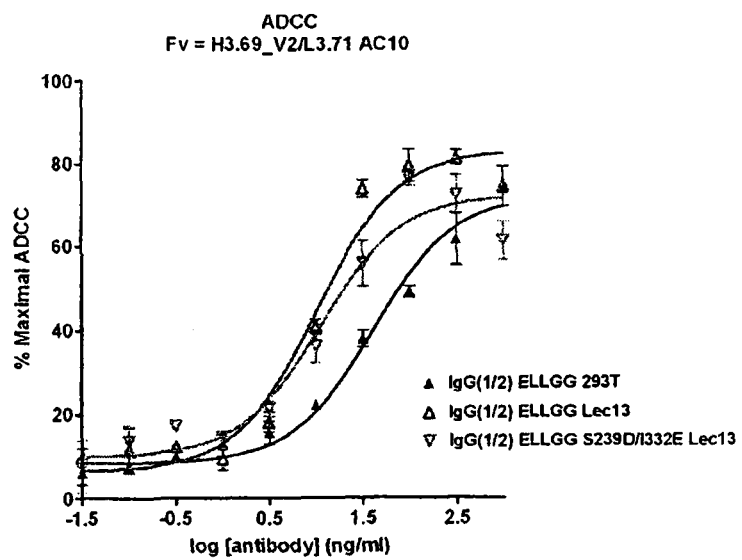
FIG. 21b. Cell-based ADCC assay of these antibodies.

A series of amino acid modifications were made in the Fc region of the H3.69_V2/L3.71 IgG1 and IgG(1/2) ELLGG antibodies to investigate the impact of enhanced FcγR affinity on the effector function of antibodies that target CD30. These variants are provided in FIG. 17. These variants were constructed, expressed, and purified as described previously. In order to explore any differences in capacity to mediate effector function, the affinities of the AC10 variants for FcγRIIIa were measured using the AlphaScreen™ assay. The extracellular region of human V158 FcγRIIIa was obtained by PCR from a clone obtained from the Mammalian Gene Collection (MGC:22630), and the receptor was fused with glutathione S-Transferase (GST) to enable screening. Tagged FcγRIIIa was transfected in 293T cells, and media containing secreted FcγRIIIa were harvested and purified. The AlphaScreen™ assay was applied as a competition assay for screening AC10 variants for binding to FcγRIIIa. Biotinylated WT AC10 antibody was bound to streptavidin donor beads (Perkin Elmer), and GST-fused human V158 FcγRIIIa was bound to anti-GST acceptor beads (Perkin Elmer). The binding data are shown in FIG. 18, and the resulting IC50's and Fold IC50's relative to WT are provided in FIG. 19.

Cell-based ADCC assays were carried out on the anti-CD30 antibody variants to investigate their effector function properties. ADCC was measured using either the DELFIA® EuTDA-based cytotoxicity assay (Perkin Elmer) or LDH Cytotoxicity Detection Kit (Roche Diagnostic Corporation, Indianapolis, Ind.). Human PBMCs were purified from leukopacks using a ficoll gradient. For europium-based detection, target cells were first loaded with BATDA at $1 \times 10^6$ cells/ml and washed 4 times. For both europium- and LDH-based detection, CD30+L540 Hodgkin's lymphoma target cells were seeded into 96-well plates at 10,000 cells/well, and opsonized using Fc variant or WT antibodies at the indicated final concentration. Triton X100 and PBMCs alone were typically run as controls. Effector cells were added at 25:1 PBMCs:target cells, and the plate was incubated at 37° C. for 4 hrs. Cells were incubated with either Eu3+ solution or LDH reaction mixture, and relative fluorescence units were measured. Data were normalized to maximal (triton) and minimal (PBMCs alone) lysis, and fit to a sigmoidal dose-response model using nonlinear regression. FIG. 20 provides these data. The results show that the optimized FcγR binding properties of the IgG variants result in improved effector function.

Example 3

Anti-CD30 Antibodies with Modified Carbohydrates that Enhance Effector Function

Carbohydrates attached to the antibodies described herein may be modified. For example, the antibodies may be modified as described by Chowdhury & Wu, 2005, Methods 36:11-24, incorporated herein by reference in its entirety.

Glycoengineering. An IgG molecule contains two N-linked glycan chains attached to Asn297 in each of its heavy chains and is part of the Fc portion. It is well known that IgG is produced as a heterogeneous populationof gylcoforms in mammalian cells. Fc glycosylation is important for the interaction with Fc receptors. This interaction is known to be sensitive to changes in the oligosaccharide structures of the Fc region (Wright & Morrison, 1998, J. Immunol. 160:3393-3402; Lund et al., 1996, J. Immunol. 157:4963-4969. The oligosaccharide core normally found attached to the human IgG Fc is of the bi-antennary type and consists of Asn297-linked GlcNAc(Fuc)-GlcNAc-Man-(Man-GlcNAc)$_2$. Individual IgG molecules vary with respect to terminal galactose or galactose-sialic acids at one or both of the terminal GlcNAc and/or attachment of a third GlcNAc (bisecting GlcNAc). They also differ with respect to the presence or absence of a fucose residue attached to the GlcNAc that is linked to Asn297. Glycoengineering for improving ADCC has been focused on the bisecting GlcNAc and the core fucose.

Bisecting GlcNAc engineering. Studies by Umana et al. (Umana et al., 1999, Nat. Biotechnol. 17:176-180, entirely incorporated by reference) showed that CHO cells when engineered to produce β(1,4)-N-acetylglucosaminyltransferase III from an inducible plasmid, modified the glycan chain of IgG into a bisected bi-antennary type, and the resulting IgGs showed increased ADCC activity. It was, however, found in this study that there was an optimal level of β(1,4)-N-acetylglucosaminyltransferase III expression that leads to increase in ADCC. Expression of enzymes below or over this optimal level decreases ADCC activity of the IgGs produced. The addition of bisecting Glc-NAc might result in a decrease in core fucosylation of the N-linked glycan chain, which might be the reason for the increase in ADCC activity.

Core fucosylation. Shields et al. (Shields et al., 2002, J. Biol. Chem. 277:26733-26740, entirely incorporated by reference) addressed the effec of fucosylation in two different antibodies, anti-HER2 antibody, Hu4D5, and anti-IgE antibody, HuE27, and found that eliminating the fucose moiety from the core of the Fc N-linked glycan profoundly improved binding to FcγRs and the ADCC activity. In this study, about 98% of the IgGs produced from a normal CHO cells were found to be fucosylated while only 10% of the IgGs produced from a variant of CHO line called Lec13 had fucose residue. Presence or absence of fucose greatly influences ADCC activity. However, fucosylation (or de-fucosylation) did not appear to influence binding of IgG1 to FcγRI, C1q, or FcRn. The dimeric forms of hypo-fucosylated IgG obtained from the Lec13 cells did exhibit a slight increase in binding to FcγRIIa(R131) and FcγRIIb. The difference between the hyper- and hypo-fucosylated IgG was more striking with respect to binding to FcγRIIIa. In this case, there was at least 42-fold increased binding to the FcγRIIIa (F158) allotype and about 19-fold increased binding to the FcγRIIIa(V158) allotype by the hypofucosylated IgG dimers compared to the hyper-fucosylated IgG dimers. In terms of ADCC activity, the hypofucosylated IgG showed enhanced activity compared to the parental hyper-fucosylated IgG when PBMCs from individuals with FcγRIIIa(V158/F158) and FcγRIIIa(F158/F158) were used. Therefore, the data suggest that improved binding to FcγRIIIa by the hypo-fucosylated IgG translated into improved ADCC activity. Reduced fucosylation has also been investigated using a rat hybridoma cell line YB2/0 (Shinkawa et al., 2003, *J Biol Chem* 278:3466-3473; Niwa et al., 2004, Cancer Research 64:2127-2133; Okazaki et al., 2004, J Mol Biol 336:1239-1249, each of which is incorporated by reference in its entirety.

By "engineered glycoform" as used herein is meant a carbohydrate composition that is covalently attached to an anti-CD30 antibody, wherein said carbohydrate composition differs chemically from that of a parent anti-CD30 antibody. Said antibody is said to be "glycoengineered". Engineered glycoforms may be useful for a variety of purposes, including but not limited to enhancing or reducing effector function. Engineered glycoforms may be generated by a variety of methods known in the art (Umana et al., 1999, *Nat Biotechnol* 17:176-180; Davies et al., 2001, *Biotechnol Bioeng* 74:288-294; Shields et al., 2002, *J Biol Chem*

277:26733-26740; Shinkawa et al., 2003, *J Biol Chem* 278:3466-3473); (U.S. Pat. No. 6,602,684; U.S. Ser. Nos. 10/277,370; 10/113,929; PCT WO 00/61739A1; PCT WO 01/29246A1; PCT WO 02/31140A1; PCT WO 02/30954A1); (Potelligent™ technology [Biowa, Inc., Princeton, N.J.]; GlycoMAb™ glycosylation engineering technology [GLYCART biotechnology AG, Zurich, Switzerland]), all incorporated herein by reference in their entirety.

Many of these techniques are based on controlling the level of fucosylated and/or bisecting oligosaccharides that are covalently attached to the Fc region, for example by expressing an anti-CD30 antibody in various organisms or cell lines, engineered or otherwise (for example Lec-13 CHO cells or rat hybridoma YB2/0 cells), by regulating enzymes involved in the glycosylation pathway (for example FUT8 [α1,6-fucosyltransferase] and/or β1-4-N-acetylglucosaminyltransferase III [GnTIII]), or by modifying carbohydrate(s) after the anti-CD30 antibody has been expressed. Engineered glycoform typically refers to the different carbohydrate or oligosaccharide; thus an anti-CD30 antibody, for example an anti-CD30 antibody, may comprise an engineered glycoform. Alternatively, engineered glycoform may refer to the anti-CD30 antibody that comprises the different carbohydrate or oligosaccharide.

The Lec13 cell line (Ripka et al. Arch. Biochem. Biophys. 49:533-545 (1986)) was utilized to express human antibodies with reduced fucose content. Lec13 refers to the lectin-resistant Chinese Hamster Ovary (CHO) mutant cell line which displays a defective fucose metabolism and therefore has a diminished ability to add fucose to complex carbohydrates. That cell line is described in Ripka & Stanley, 1986, Somatic Cell & Molec. Gen. 12(1):51-62; and Ripka et al., 1986, Arch. Biochem. Biophys. 249(2):533-545. Lec13 cells are believed lack the transcript for GDP-D-mannose-4,6-dehydratase, a key enzyme for fucose metabolism. Ohyama et al., 1988, J. Biol. Chem. 273(23):14582-14587. GDP-D-mannose-4,6-dehydratase generates GDP-mannose-4-keto-6-D-deoxymannose from GDP-mannose, which is then converted by the FX protein to GDP-L-fucose. Expression of fucosylated oligosaccharides is dependent on the GDP-L-fucose donor substrates and fucosyltransferase(s). The Lec13 CHO cell line is deficient in its ability to add fucose, but provides IgG with oligosaccharide which is otherwise similar to that found in normal CHO cell lines and from human serum (Jefferis, R. et al., 1990, Biochem. J. 268, 529-537; Raju, S. et al., 2000, Glycobiology 10, 477-486; Routier, F. H., et al., 1997, Glycoconj. J. 14, 201-207). Normal CHO and HEK293 cells add fucose to IgG oligosaccharide to a high degree, typically from 80-98%, and IgGs from sera are also highly fucosylated (Jefferis, R. et al., 1990, Biochem. J. 268, 529-537; Raju, S. et al., 2000, Glycobiology 10, 477-486; Routier, F. H., et al., 1997, Glycoconj. J. 14, 201-207; Shields et al., 2002, J Biol Chem 277(90):26733-26740). It is well established that antibodies expressed in transfected Lec13 cells consistently produce about 10% fucosylated carbohydrate (Shields et al., 2002, J Biol Chem 277(90):26733-26740).

WT, G236A, and S239D/I332E variant anti-EpCAM antibodies were each transiently expressed in 293T and Lec13 cells and purified as described above. Binding affinity to human FcγR1, H131 FcγRIIa, R131FcγRIIa, FcγRIIb, and V158 FcγRIIIa by Fc variant anti-EpCAM antibodies was measured using the SPR experiment described above. FIG. 19 provides the equilibrium constants obtained from the fits of the SPR data for all of the receptors, as well as the calculated fold KD relative to WT and the negative log of the KD (−log(KD). FIG. 20 provides a plot of the negative log of the KD for binding of the antibodies to the set of human FcγRs. The data confirm that reduced fucosylation provides an increase in affinity only for FcγRIIIa, and does not alter affinity for any of the other FcγRs. However combination of glycoengineering with a substitution that selectively improves the FcγR affinity for FcγRIIa relative to FcγRIIb, in this case G236A, provides the optimal FcγR affinity profile of selectively improved affinity for FcγRIIa and FcγRIIIa relative to the inhibitory receptor FcγRIIb. Given the macrophage phagocytosis and DC activation data provided above, this novel combination of glycoengineering and amino acid substitutions with selective FcγR affinity profiles has the potential for producing more efficacious therapeutic antibodies than glycoengineering alone. The use of the Lec13 cell line is not meant to limit the present invention to that particular mode of reducing fucose content. A variety of other methods are known in the art for controlling the level of fucosylated and/or bisecting oligosaccharides that are covalently attached to the Fc region, including but not limited to expression in various organisms or cell lines, engineered or otherwise (for example Lec13 CHO cells or rat hybridoma YB2/0 cells), regulation of enzymes involved in the glycosylation pathway (for example FUT8 [α1,6-fucosyltransferase] and/or p1-4-N-acetylglucosaminyltransferase III [GnTIII]), and modification of modifying carbohydrate(s) after the IgG has been expressed (Umaña et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473); (U.S. Pat. No. 6,602,684; U.S. Ser. Nos. 10/277,370; 10/113,929; PCT WO 00/61739A1; PCT WO 01/29246A1; PCT WO 02/31140A1; PCT WO 02/30954A1).

Example 4

In Vitro Biological Activity of Anti-Cd30 Antibodies

Figure 23:
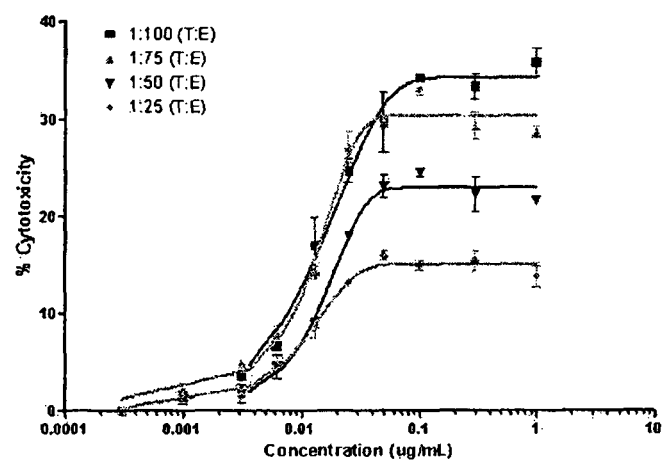
FIG. 23. Cytotoxicity of XmAb2513 Target to Effector cell ratio titration.
Figure 24:
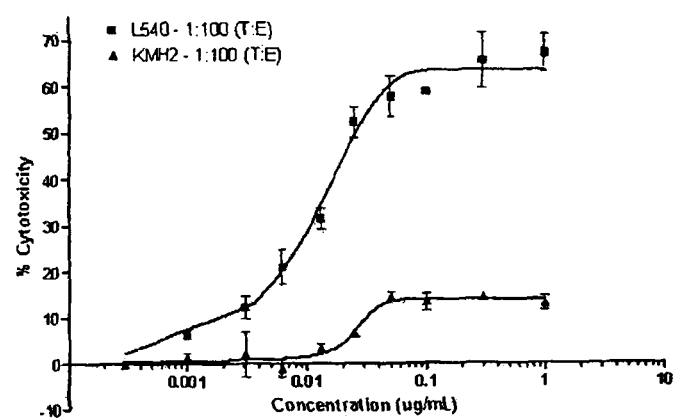
FIG. 24. Cytotoxicity against cell lines expressing low and high levels of CD30 target antigen.
Figure 25:
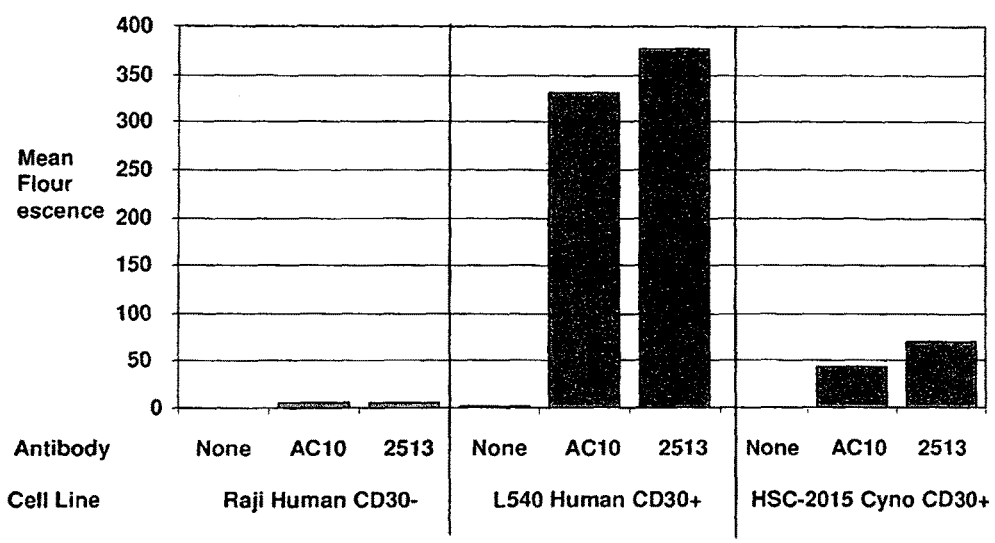
FIG. 25. Binding of 2513 to human and macaque CD30+ cell lines.

The H3.69_V2/L3.71 AC10 IgG(1/2) ELLGG antibody was chosen for further study, and is designated XmAb2513 or just 2513. FIG. 22 is a table of cell lines and relative expression of the anti-CD30 antibody of the present invention. FIG. 23 shows cytotoxicity of XmAb2513 against CD30+ cells at varying target to effector cell ratios. FIG. 24 shows cytotoxicity against the CD30+ cell lines L540 and KMH2. FIG. 25 shows binding of H0L0 AC10 and XmAb2513 to human and cynomolgus monkey cell lines.

Figure 26:
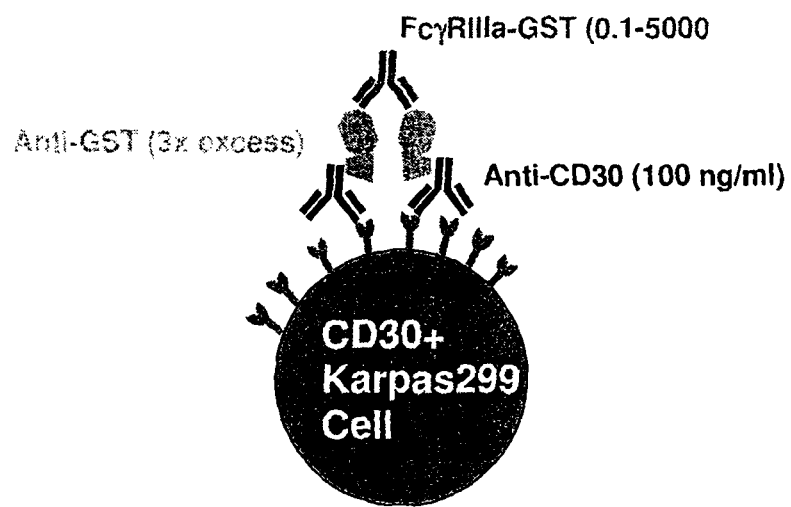
FIG. 26. Illustration of assay to measure FcγR-mediated anti-proliferation.
Figure 27:
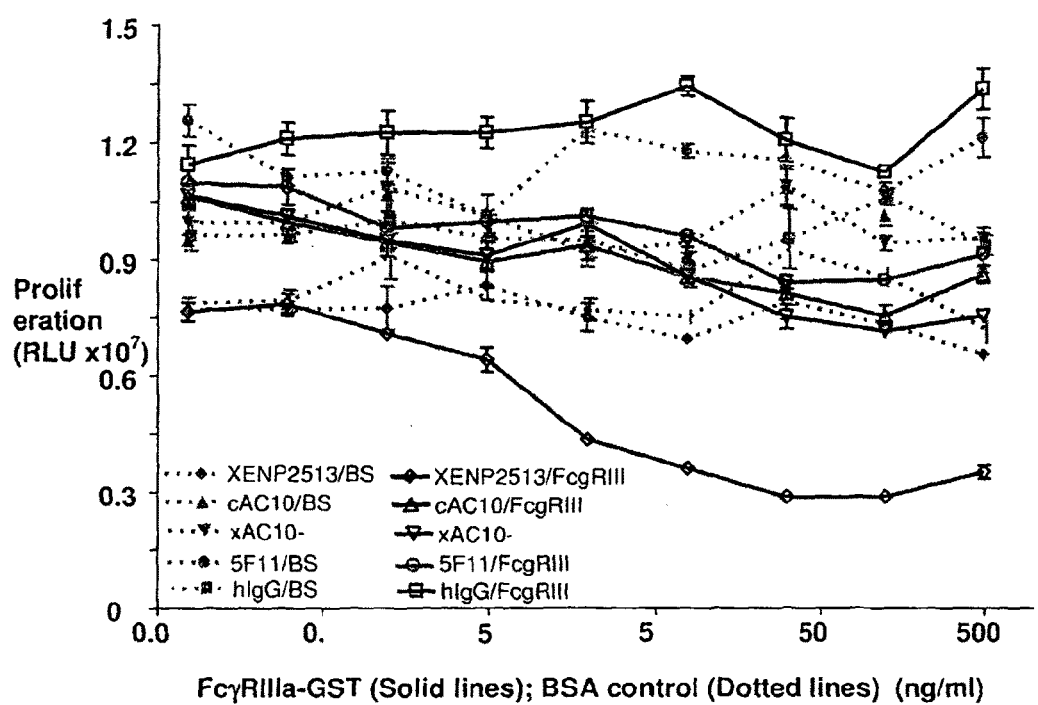
FIG. 27. Enhanced anti-proliferative effect in vitro of 2513 relative to the parent antibody.

To observe an anti-proliferative effect in vitro, many antibodies require crosslinking, usually accomplished by a secondary antibody. It has been proposed that corresponding in vivo effects for these antibodies may be dependent on Fc receptor mediated crosslinking. Due to its higher affinity for Fc receptors, XmAb2513 may have correspondingly higher anti-proliferative effects in vivo. To measure FcγRIIIa mediated antibody crosslinking: Karpas299 cells were grown with 100 ng/ml of anti-CD30 and varying concentrations of higher BSA or FcγRIIIa-GST with goat anti-GST antibody to cross link. This assay is illustrated in FIG. 26. FIG. 27 shows the anti-proliferative effect in vitro of the antibody of the present invention. As can be seen, the enhanced FcγR affinity of the effector function enhanced anti-CD30 antibody provides enhanced anti-proliferative effects.

Example 5

Formulations

The stability of exemplary anti-CD30 antibody comprising SEQ ID Nos: 19 and 20 was examined in 12 different formulations during a Stage I of the Preformulation Characterization Study. The objective was to study formulation parameters to identify conditions that best stabilize the antibody.

SEC-HPLC and SDS-PAGE and the were used to monitor the stability of the antibody.

Summary stability plots of recovery under temperature storage supported the better stability of sodium chloride formulations at pH's 6.0-7.0 at all incubation temperatures, while the purity plots indicated better stability of sorbitol formulations at pH 6.0 at higher incubation temperatures of 29-37° C. The discrepancy between leading formulations in the recovery and purity plots can be attributed to underestimation of aggregates that are insoluble in sorbitol formulations.

Results up to Eight Weeks showed higher purity on SEC-HPLC for antibody formulations containing sorbitol in the pH range of 4.0-6.0, which was subsequently found to be due to the insolubility of aggregates as evidenced by corresponding decreases in recovery. Generally, sodium chloride appears to be a better tonicity modifier due to better recovery even though sodium chloride formulations contained more aggregates. Formulations at pH 6-7 with either sorbitol or sodium chloride showed no significant change during storage at 4° C. for 8 weeks, the duration of this study.

The presence of surfactant, such as polysorbate 20 and polysorbate 80, did not appear to exert any effect on the temperature stability of the formulations tested. However, under the stress conditions of agitation and freeze-thaw, formulations without surfactant formed precipitates.

Tonicity modifier did not appear to have an effect in the agitation study, while sorbitol formulations fared better in the freeze-thaw study. The antibody was found to be subject to minor degree of UV light-induced aggregation in all tested formulations, regardless of tonicity modifier.

The main objective of this study was to investigate formulation parameters to determine optimal conditions for the stabilization of XENP2513, which included the identification of key stresses and degradation products, and the development of reliable stability-indicating assays.

Formulation Parameters:
(1) pH: 4.0, 5.0, 6.0, 7.0, 8.0;
(2) Buffers: Sodium acetate buffer (pH 4.0-5.0) and sodium phosphate buffer (pH 6.0-8.0) at 10 mM concentration;
(3) Tonicity modifiers: sodium chloride (NaCl) at 150 mM concentration or 5% sorbitol;
(4) Surfactant: none, polysorbate 20 or polysorbate 80;
(5) XENP2513 reference standard at 6.3 mg/mL to be stored at 4° C. and diluted to 1 mg/mL for analyses for the duration of the study;
(6) The concentration of XENP2513 will be 1 mg/mL for initial screening study.

Visual Observation

When the antibody was formulated in citrate buffer, pH 5.5 or lower, the solution became cloudy. This may be attributable to the citrate buffer, pH or tonicity modifier.

To minimize the antibody material requirements, a quick visual observation study was performed to monitor the presence and cause of cloudiness in low pH samples. Integrity Biosolution dialyzed 0.25 ml of 6.3 mg/ml antibody into the following buffers:
(1) 10 mM Sodium acetate, 150 mM sodium chloride, pH 4.0
(2) 10 mM Sodium acetate, 150 mM sodium chloride, pH 5.0
(3) 10 mM Sodium acetate, 5% sorbitol, pH 4.0
(4) 10 mM Sodium acetate, 5% sorbitol, pH 5.0

After dialysis, visual inspection of the sample vials was performed and antibody concentration was diluted to 1 mg/mL with corresponding buffers and visually inspected. The samples were stored at 29° C. for 24 hours and visually inspected again.

If pH is responsible for the cloudiness of formulations, then pH 4.0-5.0 will be excluded from the stability matrix. If citrate buffer is responsible, then the stability matrix will remain as is. If tonicity modifier is responsible for the cloudiness, then the specific tonicity modifier for those pH('s) will be removed from the stability matrix.

SEC-HPLC Method:
SEC-HPLC: Protein aggregation
Column: TSK-GEL Super SW3000, 0.46×30 cm (no guard column)
Mobile Phase A: 1×PBS, no Ca or Mg
Flow Rate: 0.35 mL/min
Gradient: Isocratic
Run Time: 15 minutes
Column Temperature Ambient
cIEX-HPLC Method
CEX-HPLC: Protein deamidation and others
Column: Dionex ProPac WCX-10 (4 mm×250 mm)
Mobile Phase A: 10 mM sodium acetate, pH 5.0
Mobile Phase B: 10 mM sodium acetate, 1 M sodium chloride, pH 5.0
Flow Rate: 1.0 mL/min
Gradient:

| Time (min) | % B |
| --- | --- |
| 0 | 0 |
| 30 | 45 |
| 31 | 100 |
| 34 | 100 |
| 35 | 0 |
| 40 | 0 |

SDS-PAGE Method:
SDS-PAGE: Protein aggregation
Gel Type NuPAGE Novex 4-12% Bis Tris Gel, 15 well
Running Buffer: 1×MES SDS Running Buffer
Staining Reagent Simply Blue SafeStain, Invitrogen
Load volume: 15 µL
Sample load: 2.5 µg
Sample Prep: 10 µL diluted sample, 12.5 water, and 7.5 4×LDS Sample Buffer were added to each well of a 15 well gel. The samples were heated to 70° C. for 5 minutes. The samples were then cooled to room temperature and vortex briefly. 10 µL of Mark 12 MW Standard, 15 µL of Reference Standard, and 15 µL of Samples into 4-12% Bis Tris Gel, were loaded into a 15 well. A Mini-Cell electrophoresis apparatus containing gel was run for 70 minutes at 150V. The gel cassette was removed from Mini-Cell apparatus and rinse 3 times with Milli-Q water for 5 minutes each. SimplyBlue Safestain was added to the gel for 1 hour. Safestain was decanted and add Milli-Q water was added to destain for 3 hours. The gel was dried.

After dialysis, antibody formulations containing sodium chloride were cloudy, while antibody formulations containing sorbitol remained clear.

The cloudy antibody sodium chloride formulations were then incubated at 4° C., while the clear antibody sorbitol formulations were incubated at 29° C.

Antibody sorbitol formulations remained clear after 24 hours of incubation at 29° C., as were the antibody sodium chloride formulations incubated for 24 hours at 4° C. However, lower concentration readings in the sodium chloride formulations gave indication that the aggregates had settled to the bottom of the glass vials rather than re-solubilized after 24 hours' incubation.

The antibody concentration was measured at Time Zero (immediately after dialysis) and 24 hours. After 24 hours, the protein concentration was about 1.5 times lower for the antibody sodium chloride formulations, whereas sorbitol formulations/higher pH formulations showed a less dramatic loss.

The sorbitol formulation at pH 5.0 and control at pH 7.0 did not exhibit a loss of protein.

Antibody sodium chloride formulations at pH 4.0-5.0 both showed approximately 1.5 times lower concentration after 24 hours' incubation; they were subsequently excluded from the stability matrix. The sorbitol formulations at pH 4.0-5.0 did not show a significant loss of protein and will be included in the study matrix.

Stability During Temperature Storage

SEC-HPLC Results

Results were relatively comparable across all formulations at Time Zero and Week One. Generally, sorbitol formulations appeared to perform better at pH's 4.0-6.0 in terms of main peak purity, with the exception of sorbitol, pH 5.0 sample incubated for One Week at 37° C. Also, no significant difference was observed among formulations with and without the presence of surfactant.

At Week Two, sorbitol formulations at pH 5.0-6.0 continued to maintain the highest main peak purity of ~97% at −20-29° C. However, at 37° C., sorbitol formulation at pH 5.0 had the worst main peak purity at 83.71%, while sorbitol formulation at pH 6.0 had the best main peak purity at 97.24%. However, the latter exhibited a slight recovery loss compared to previous time points and to its sodium chloride counterpart.

At Week Four, sorbitol formulations at pH 5.0-6.0 appeared to be the most stable at −20° C. and 4° C., while the sorbitol, pH 5.0 sample performed the worst and the sorbitol, pH 6.0 sample emerged as the optimal formulation at 29-37° C. However, the sorbitol, pH 6.0 sample had a decreased recovery at 37° C. when compared to Week One data and to its sodium chloride counterpart.

At Week Eight, sorbitol formulations at pH 5.0-6.0 maintained the best stability at −20° C. and 4° C., while sorbitol, pH 5.0 performed the worst and sorbitol, pH 6.0 was the optimal formulation at 29-37° C. Again, sorbitol pH 6.0 sample showed a lower recovery than its sodium chloride counterpart at 37° C., which became more significant with time at 37° C.

A short insolubility study on the antibody was performed which determined that the amount of aggregates was underestimated in sorbitol formulations. Thus, despite the better purity data seen for sorbitol formulations, sodium chloride is actually the preferred tonicity modifier.

run on two different machines and divided into two graphs.

IEX-HPLC Results

IEX-HPLC method was implemented starting at Week One. The data was difficult to interpret due to merging of degradation peak with the main peak, which resulted in less than clear-cut peak integrations.

Also, a subtle retention time shift was noted at all time points, a phenomenon commonly experienced with Dionex columns. Therefore, IEX-HPLC results should, at best, be used as a qualitative and not quantitative analysis of protein stability.

For Week One, data is not available for 4° C. samples; they were run at Week Two.

At Week One, starting main peak purity was ~68% at −20° C. and 29° C. All formulations at the lower incubation temperatures of −20° C. and 29° C. were relatively comparable and stable. The most significant (~36%) degradation was seen in the pH 8.0 sodium chloride and sorbitol formulations at 37° C.

At Week Two, no significant difference was seen in −20° C. and 4° C. samples compared to corresponding Week One samples. At 29° C., main peak purity decreased to an average of ~36% for pH 8.0 formulations, while most formulations except pH 4.0-5.0 sorbitol samples showed a drastic increase of ~50% in pre-peak degradation at 37° C.

At Week Four, results followed the trend from Week Two. Overall main peak purity was ~67% and changes in degradation were minimal at −20° C. and 4° C. At 29° C., main peak purity averaged ~40% for pH 8.0 formulations. At 37° C., degradation increased across either one or both pre-peaks for most formulations except the pH 4.0 sorbitol sample, which retained ~58% main peak purity.

At Eight Weeks, formulations maintained ~68-69% main peak purity at −20° C. and 4° C. At 29° C., a marked increase in pre-peak degradation was observed in most formulations except for pH 4.0 sorbitol sample, which retained ~68% main peak purity. Data integration for samples incubated at 37° C. was not performed as peaks had become too degraded to integrate accurately.

SDS-PAGE Results

In line with SEC-HPLC results from Week One, faint higher molecular weight bands were noted in pH 8.0 formulations incubated at 37° C. in the reduced gel. No significant differences among the samples were observed at −20-29° C.

At Week Two, faint higher molecular weight bands were observed in pH 7.0-8.0 formulations incubated at 37° C. in the reduced gel, with pH 8.0 samples being more intense. No significant differences among the samples were observed at −20-29° C.

At Week Four, higher molecular weight bands were observed in pH 8.0 formulations at −20° C. in the reduced gel. A degradation band was seen for the pH 8.0 sorbitol formulation at 4° C. in the reduced gel, which may be an outlier. Also, faint higher molecular weight bands were observed in pH 7.0-8.0 for both formulations at 37° C. in the reduced gel, with pH 8.0 samples being more intense.

At Week Eight, higher and lower molecular weight bands were observed in all formulations at 37° C. in the reduced gel, with pH 8.0 samples being most severe. At 37° C., formulations pH 6.0 and above contained a double band just below the first main band, which was more obvious in sodium chloride formulations. Sorbitol formulation at pH 6.0 showed the least bands followed by sodium chloride formulation, pH 6.0.

Stability During Agitation, Freeze-Thaw, and UV

The stability of XENP2513 was tested under the following conditions:

Samples were agitated for 4 hours on VWR Mini Vortexer at ambient temperature at low setting;
Samples were frozen at −20° C. and thawed at 25° C. for 5 consecutive cycles;
Samples were exposed to UV light for 24 hours at ambient temperature;
Reference Standard was stored at 4° C. and not subjected to agitation, freeze-thaw or UV light.

After agitation and freeze-thaw, formulations without polysorbate showed particles which were filtered prior to sample analyses.

SEC-HPLC Results

Samples after agitation performed comparably with the exception of formulations without polysorbate, which were run after filtration and subsequently showed less aggregates.

Freeze-thaw samples containing sodium chloride showed an increase in pre-peak 2; no significant changes were seen in the filtered samples compared to the non-filtered samples.

UV-exposed samples showed a predominant increase in pre-peak 2, which increased with pH, while the post-peak increased in all formulations.

IEX-HPLC Results

No significant changes were seen in the agitation and freeze-thaw samples, including samples that were filtered. However, UV samples showed a significant pre-peak for all samples, which increased with pH.

SDS-PAGE Results

In both non-reduced and reduced gels, fainter bands were observed in agitated samples without polysorbate. A higher molecular weight band for freeze-thaw samples was observed in the reduced gel. For UV-exposed samples on both non-reduced and reduced gels, higher molecular weight bands were observed, which increased in intensity at higher pH's.

Summary Stability Plots

Stability plots of all 12 formulations based on their SEC-HPLC purity and recovery under temperature storage (−20° C., 4° C., 29° C., 37° C.) are presented below.

SEC-HPLC Purity

Sorbitol formulations at pH's 5.0-6.0 fared the best after Eight Weeks' incubation up to 4° C. However, at 37° C., the sorbitol sample at pH 5.0 performed the worst whereas the sorbitol sample at pH 6.0 was the optimal formulation. Please note that insolubility of aggregates was later found to be the cause for underestimation of aggregates in sorbitol formulations.

SEC-HPLC Recovery

Sodium chloride formulations at pH's 6.0-7.0 maintained the best recoveries after Eight Weeks' incubation at all temperatures.

Based on findings from this preformulation study, lower pH formulations containing sorbitol as tonicity modifier showed higher purity by SEC-HPLC, which was found to be due to insolubility of aggregates as evidenced by decrease in recovery over a period of Eight Weeks. Therefore, in one embodiment, the formulation containing sodium chloride at pH 6.0-7.0 is a preferred formulation condition despite the presence of more aggregates.

Surfactant did not significantly affect the stability of XENP2513 formulations during temperature storage, but was found to be helpful in the agitation and freeze-thaw studies.

The invention claimed is:

1. A method of treating a CD30-expressing cancer comprising administering to a subject in need thereof an anti-CD30 antibody, said antibody comprising:
    at least one amino acid substitution in the Fc region at a position selected from the group consisting of 239D and 332E relative to a parent Fc region; and
    a heavy chain and a light chain, wherein said heavy chain comprises a heavy chain variable region comprising an amino acid sequence of SEQ ID NO 11, and wherein said light chain comprises a light chain variable region comprising an amino acid sequence of SEQ ID NO 10, and
    said antibody binds with enhanced affinity to FcyRIIIa as compared to a parent antibody, wherein numbering is according to the EU index as in Kabat.

2. The method of claim 1, wherein a first substitution is 239D.

3. The method of claim 2, wherein a second substitution is 332E.

4. The method of claim 3, wherein said indication is a the CD30-expressing cancer selected from carcinoma, B cell tumor, lymphoma, blastoma, sarcoma (Including liposarcoma), neuroendocrine tumors, mesothelioma, schwanoma, meningioma, adenocarcinoma, melanoma, and leukemia or lymphoid malignancies.

5. The method of claim 4, wherein said indication the CD30-expressing cancer is selected from Hodgkin's lymphoma, anaplastic large-cell lymphoma, (ALCL), immunoblastic lymphoma, multiple myeloma, adult T-cell lymphoma leukemia, mycosis fungoides, germ-cell malignancies, chronic lymphocytic leukemia (CLL), follicular B-cell lymphoma, hairy cell leukemia, T-cell lymphoblastic lymphoma, and adult T-cell leukemia lymphoma.

6. The method of claim 5, wherein the CD30-expressing cancer is Hodgkin's lymphoma.

7. The method of claim 1, wherein the CD30-expressing cancer is selected from carcinoma, B cell tumor, lymphoma, blastoma, sarcoma (including liposarcoma), neuroendocrine tumors, mesothelioma, schwanoma, meningioma, adenocarcinoma, melanoma, and leukemia or lymphoid malignancies.

8. The method of claim 7, wherein the CD30-expressing cancer is selected from Hodgkin's lymphoma, anaplastic large-cell lymphoma, (ALCL), immunoblastic lymphoma, multiple myeloma, adult T-cell lymphoma leukemia, mycosis fungoides, germ-cell malignancies, chronic lymphocytic leukemia (CLL), follicular B-cell lymphoma, hairy cell leukemia, T-cell lymphoblastic lymphoma, and adult T-cell leukemia lymphoma.

9. The method of claim 8, wherein the CD30-expressing cancer is Hodgkin's lymphoma.

* * * * *

UNITED STATES PATENT AND TRADEMARK OFFICE
CERTIFICATE OF CORRECTION

PATENT NO. : 9,574,006 B2
APPLICATION NO. : 13/163465
DATED : February 21, 2017
INVENTOR(S) : Lazar et al.

It is certified that error appears in the above-identified patent and that said Letters Patent is hereby corrected as shown below:

In the Claims

| Column | Line | Reads | Should Read |
|---|---|---|---|
| 107 | 35 | "4. The method of claim 3, wherein said indication is a the" | -- 4. The method of claim 3, wherein the -- |
| 108 | 14 | "5. The method of claim 4, wherein said indication the" | -- 5. The method of claim 4, wherein the -- |

Signed and Sealed this
Twenty-third Day of May, 2017

Michelle K. Lee
*Director of the United States Patent and Trademark Office*